US006576243B1

(12) United States Patent
Audonnet et al.

(10) Patent No.: US 6,576,243 B1
(45) Date of Patent: *Jun. 10, 2003

(54) POLYNUCLEOTIDE VACCINE FORMULA AGAINST PORCINE REPRODUCTIVE AND RESPIRATORY PATHOLOGIES

(75) Inventors: Jean-Christophe Audonnet, Lyons (FR); Annabelle Bouchardon, Lyons (FR); Philippe Baudu, Craponne (FR); Michel Riviere, Ecully (FR)

(73) Assignee: Merial, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/784,984

(22) Filed: Feb. 16, 2001

Related U.S. Application Data

(60) Division of application No. 09/232,468, filed on Jan. 15, 1999, now Pat. No. 6,207,165, which is a continuation-in-part of application No. PCT/FR97/01313, filed on Jul. 15, 1997.

(30) Foreign Application Priority Data

Jul. 19, 1996 (FR) .............................. 96 09338

(51) Int. Cl.[7] ....................... A61K 39/12; A61K 39/295
(52) U.S. Cl. ............... 424/199.1; 424/201.1; 424/220.1; 424/204.1; 424/815; 435/320.1; 435/69.1; 536/23.72
(58) Field of Search ............ 424/199.1, 201.1, 424/220.1, 204.1, 815; 435/320.1, 69.1; 536/23.72

(56) References Cited

FOREIGN PATENT DOCUMENTS

| WO | WO 95/20660 | 8/1995 |
| WO | WO 96/06619 | 3/1996 |
| WO | WO 97/23502 | 7/1997 |

OTHER PUBLICATIONS

Cox et al., Journal of Virology, 1993, vol. 67(9), pp. 5664–5667.
Haynes et al. Journal of Biotechnology, 1996, vol. 44, pp. 37–42.
Xiang et al. Immunity, 1995, vol. 2, pp. 129–135.
Xiang et al. Virology, 1995, vol. 209, pp. 569–579.
Andrew et al., Vaccine 18:1932–1938 (2000).
Yu et al., Vaccine 19: 1520–1525 (2001).
Somasundaram et al., Vet Immunology and Immunopathology 70 :277–87 (1999).
Haagmans et al., Vaccine 17 :1264–71 (1999).
van Rooji et al., Vet Immunology and Immunopathology 66 :113–126 (1998).
van Rooij et al., Vet Immunology and Immunopathology 74 :121–136 (2000).
Kwang et al., Res Vet Sci 67 :199–201 (1999).
Le Potier, M–F., et al. "Study of the delivery of the GD gene of PRV to one–day–old piglets by adenovirus or plasmid DNA as ways to by–pass the inhibition of immune response by colostral antibodies" Second Internation Symposiu m in the Eradication of Aujeszky's Disease (pseudorabies) Virus, Aug. 6–8, 1995, Sopenhagen, Denmark.
Pirzadeh, B. and Dea, S. "Immune response in pigs vaccinated with plasmid DNA encoding ORF5 of reproductive and respiratory syndrome virus." Journal of General Virology, 1998, 79:989–999.

*Primary Examiner*—Ali R. Salimi
(74) *Attorney, Agent, or Firm*—Frommer Lawrence & Haug LLP; William S. Frommer; Thomas J. Kowalski

(57) ABSTRACT

Disclosed and claimed is: an immunogenic or vaccine composition for inducing in an avian host an immunological response against avian pathologies containing at least one plasmid that contains and expresses in vivo in an avian host cell nucleic acid molecule(s) having sequence(s) encoding antigen(s) of the avian pathogen(s); and, methods for using and kits employing such compositions.

30 Claims, 31 Drawing Sheets

```
   1 ATGCCCGCTGGTGGCGGTCTTTGGCGCGGGCCCCGGGGGCATCGGCCCGGGCACCACGGCGGT
   1▶MetProAlaGlyGlyGlyLeuTrpArgGlyProArgGlyHisArgProGlyHisHisGlyGly
                                                           PstI
  64 GCTGGCCTCGGACGTCTTTGGCCTGCTCCACACCACGCTGCAGCTGCGCGGGGCGCCGTCGCG
  22▶AlaGlyLeuGlyArgLeuTrpProAlaProHisHisAlaAlaAlaAlaArgGlyAlaValAla
 127 CTAGCGCTGCTGCTGCTGGCGCTCGCCGCGGCCCCGCCGTGCGGCGCGGCGGCCGTGACGCGG
  43▶LeuAlaLeuLeuLeuLeuAlaLeuAlaAlaAlaProProCysGlyAlaAlaAlaValThrArg
 190 GCCGCCTCGGCCTCGCCGACGCCCGGGACGGGCGCCACCCCCAACGACGTCTCCGCCGAGGCG
  64▶AlaAlaSerAlaSerProThrProGlyThrGlyAlaThrProAsnAspValSerAlaGluAla
      XhoI
 253 TCCCTCGAGGAGATCGAGGCGTTCTCCCCCGGCCCCTCGGAGGCCCCCGACGGCGAGTACGGC
  85▶SerLeuGluGluIleGluAlaPheSerProGlyProSerGluAlaProAspGlyGluTyrGly
 316 GACCTGGACGCGCGGACGGCCGTGCGCGCGGCCGCGACCGAGCGGGACCGCTTCTACGTCTGC
 106▶AspLeuAspAlaArgThrAlaValArgAlaAlaAlaThrGluArgAspArgPheTyrValCys
 379 CCGCCGCCGTCCGGCTCCACGGTGGTGCGGCTGGAGCCCGAGCAGGCCTGCCCCGAGTACTCG
 127▶ProProProSerGlySerThrValValArgLeuGluProGluGlnAlaCysProGluTyrSer
 442 CAGGGGCGCAACTTCACGGAGGGGATCGCCCTGCTCTTCAAGGAGAACATCGCCCCGCACAAG
 148▶GlnGlyArgAsnPheThrGluGlyIleAlaLeuLeuPheLysGluAsnIleAlaProHisLys
 505 TTCAAGGCCCACATCTACTACAAGAACGTCATCGTCACGACCGTGTGGTCCGGGAGCACGTAC
 169▶PheLysAlaHisIleTyrTyrLysAsnValIleValThrThrValTrpSerGlySerThrTyr
 568 GCGGCCATCACGAACCGCTTCACAGACCGCGTGCCCGTCCCCGTGCAGGAGATCACGGACGTG
 190▶AlaAlaIleThrAsnArgPheThrAspArgValProValProValGlnGluIleThrAspVal
 631 ATCGACCGCCGCGGCAAGTGCGTCTCCAAGGCCGAGTACGTGCGCAACAACCACAAGGTGACC
 211▶IleAspArgArgGlyLysCysValSerLysAlaGluTyrValArgAsnAsnHisLysValThr
 694 GCCTTCGACCGCGACGAGAACCCCGTCGAGGTGGACCTGCGCCCCTCGCGCCTGAACGCGCTC
 232▶AlaPheAspArgAspGluAsnProValGluValAspLeuArgProSerArgLeuAsnAlaLeu
 757 GGCACCCGCGCCTGGCACACCACCAACGACACCTACACCAAGATCGGCGCCGCGGGCTTCTAC
 253▶GlyThrArgAlaTrpHisThrThrAsnAspThrTyrThrLysIleGlyAlaAlaGlyPheTyr
 820 CAGACGGGCACCTCCGTCAACTGCATCGTCGAGGAGGTGGAGGCGCGCTCCGTGTACCCCTAC
 274▶GlnThrGlyThrSerValAsnCysIleValGluGluValGluAlaArgSerValTyrProTyr
 883 GACTCCTTCGCCCTGTCCACGGGGGACATTGTGTACATGTCCCCCTTCTACGGCCTGCGCGAG
 295▶AspSerPheAlaLeuSerThrGlyAspIleValTyrMetSerProPheTyrGlyLeuArgGlu
 946 GGGGCCCACGGGGAGCAGATCGGCTACGCGCCCGGGCGCTTCCAGCAGGTGGAGCACTACTAC
 316▶GlyAlaHisGlyGluGlnIleGlyTyrAlaProGlyArgPheGlnGlnValGluHisTyrTyr
1009 CCCATCGACCTGGACTCGCGCCTCCGCGCCTCCGAGAGCGTGACGCGCAACTTTCTACGCACG
 337▶ProIleAspLeuAspSerArgLeuArgAlaSerGluSerValThrArgAsnPheLeuArgThr
1072 CCGCACTTCACGGTGGCCTGGGACTGGGCCCCCAAGACGCGGCGCGTGTGCAGCCTGGCCAAG
 358▶ProHisPheThrValAlaTrpAspTrpAlaProLysThrArgArgValCysSerLeuAlaLys
1135 TGGCGCGAGGCCGAGGAGATGACCCGCGACGAGACGCGCGACGGCTCCTTCCGCTTCACGTCG
 379▶TrpArgGluAlaGluGluMetThrArgAspGluThrArgAspGlySerPheArgPheThrSer
                                                           PstI
1198 CGGGCCCTGGGCGCCTCCTTCGTCAGCGACGTCACGCAGCTGGACCTGCAGCGCGTGCACCTG
 400▶ArgAlaLeuGlyAlaSerPheValSerAspValThrGlnLeuAspLeuGlnArgValHisLeu
1261 GGCGACTGCGTCCTCCGCGAGGCCTCGGAGGCCATCGACGCCATCTACCGGCGGCGCTACAAC
 421▶GlyAspCysValLeuArgGluAlaSerGluAlaIleAspAlaIleTyrArgArgArgTyrAsn
1324 AGCACGCACGTGCTGGCCGGCGACAGGCCCGAGGTGTACCTCGCCCGCGGGGGCTTCGTGGTG
 442▶SerThrHisValLeuAlaGlyAspArgProGluValTyrLeuAlaArgGlyGlyPheValVal
```

FIG. 2a

| FIG. 2 | FIG. 2a |
|---|---|
| | FIG. 2b |

```
                                                                    XhoI
1387  GCCTTCCGCCCGCTGATCTCGAACGAGCTGGCGCAGCTGTACGCGCGCGAGCTCGAGCGCCTC
 463▸ AlaPheArgProLeuIleSerAsnGluLeuAlaGlnLeuTyrAlaArgGluLeuGluArgLeu
1450  GGCCTCGCCGGCGTCGTGGGCCCCGCGGCCCCCGCGGCCGCCCGTCGGGCCCGGCGCTCCCCC
 484▸ GlyLeuAlaGlyValValGlyProAlaAlaProAlaAlaAlaArgArgAlaArgArgSerPro
1513  GGCCCGGCGGGGACGCCCGAGCCGCCGGCCGTCAACGGCACGGGGCACCTGCGCATCACCACG
 505▸ GlyProAlaGlyThrProGluProProAlaValAsnGlyThrGlyHisLeuArgIleThrThr
                                       PstI
1576  GGCTCGGCGGAGTTTGCGCGCCTGCAGTTCACCTACGACCACATCCAGGCGCACGTGAACGAC
 526▸ GlySerAlaGluPheAlaArgLeuGlnPheThrTyrAspHisIleGlnAlaHisValAsnAsp
                             PstI
1639  ATGCTGGGCCGCATCGCGGCCGCCTGGTGCGAGCTGCAGAACAAGGACCGCACCCTGTGGAGC
 547▸ MetLeuGlyArgIleAlaAlaAlaTrpCysGluLeuGlnAsnLysAspArgThrLeuTrpSer
1702  GAGATGTCGCGCCTGAACCCCAGCGCCGTGGCCACGGCCGCGCTCGGCCAGCGCGTCTGCGCG
 568▸ GluMetSerArgLeuAsnProSerAlaValAlaThrAlaAlaLeuGlyGlnArgValCysAla
1765  CGCATGCTCGGCGACGTGATGGCCATCTCGCGGTGCGTGGAGGTGCGCGGCGGCGTGTACGTG
 589▸ ArgMetLeuGlyAspValMetAlaIleSerArgCysValGluValArgGlyGlyValTyrVal
1828  CAGAACTCCATGCGCGTGCCCGGCGAGCGCGGCACGTGCTACAGCCGCCCGCTGGTCACCTTC
 610▸ GlnAsnSerMetArgValProGlyGluArgGlyThrCysTyrSerArgProLeuValThrPhe
1891  GAGCACAACGGCACGGGCGTGATCGAGGGCCAGCTCGGCGACGACAACGAGCTCCTCATCTCG
 631▸ GluHisAsnGlyThrGlyValIleGluGlyGlnLeuGlyAspAspAsnGluLeuLeuIleSer
1954  CGCGACCTCATCGAGCCCTGCACCGGCAACCACCGGCGCTACTTTAAGCTGGGGAGCGGGTAC
 652▸ ArgAspLeuIleGluProCysThrGlyAsnHisArgArgTyrPheLysLeuGlySerGlyTyr
2017  GTGTACTACGAGGACTACAACTACGTGCGCATGGTGGAGGTGCCCGAGACGATCAGCACGCGG
 673▸ ValTyrTyrGluAspTyrAsnTyrValArgMetValGluValProGluThrIleSerThrArg
                                                              XhoI
2080  GTTACCCTGAACCTGACGCTGCTGGAGGACCGCGAGTTCCTGCCCCTCGAGGTGTACACGCGC
 694▸ ValThrLeuAsnLeuThrLeuLeuGluAspArgGluPheLeuProLeuGluValTyrThrArg
2143  GAGGAGCTCGCCGACACGGGCCTCCTGGACTACAGCGAGATCCAGCGCCGCAACCAGCTGCAC
 715▸ GluGluLeuAlaAspThrGlyLeuLeuAspTyrSerGluIleGlnArgArgAsnGlnLeuHis
2206  GCGCTCAAGTTCTACGACATCGACCGCGTGGTCAAGGTGGACCACAACGTGGTGCTGCTGCGC
 736▸ AlaLeuLysPheTyrAspIleAspArgValValLysValAspHisAsnValValLeuLeuArg
2269  GGCATCGCCAACTTCTTCCAGGGCCTCGGCGACGTGGGCGCCGCCGTCGGCAAGGTGGTCCTG
 757▸ GlyIleAlaAsnPhePheGlnGlyLeuGlyAspValGlyAlaAlaValGlyLysValValLeu
2332  GGTGCCACGGGGGCCGTGATCTCGGCCGTCGGCGGCATGGTGTCCTTCCTGTCCAACCCCTTC
 778▸ GlyAlaThrGlyAlaValIleSerAlaValGlyGlyMetValSerPheLeuSerAsnProPhe
2395  GGGGCGCTCGCCATCGGGCTGCTGGTGCTGGCCGGCCTGGTCGCGGCCTTCCTGGCCTACCGG
 799▸ GlyAlaLeuAlaIleGlyLeuLeuValLeuAlaGlyLeuValAlaAlaPheLeuAlaTyrArg
2458  CACATCTCGCGCCTGCGCCGCAACCCCATGAAGGCCCTGTACCCCGTCACGACGAAGACGCTC
 820▸ HisIleSerArgLeuArgArgAsnProMetLysAlaLeuTyrProValThrThrLysThrLeu
               SalI
2521  AAGGAGGACGGCGTCGACAAGGCGACGTGGACGAGGCCAAGCTGGACCAGGCCCGGGACATG
 841▸ LysGluAspGlyValAspGluGlyAspValAspGluAlaLysLeuAspGlnAlaArgAspMet
                                      XhoI
2584  ATCCGGTACATGTCCATCGTGTCGGCCCTCGAGCAGCAGGAGCACAAGGCGCGCAAGAAGAAC
 862▸ IleArgTyrMetSerIleValSerAlaLeuGluGlnGlnGluHisLysAlaArgLysLysAsn
2647  AGCGGGCCCGCGCTGCTGGCCAGCCGCGTCGGGGCGATGGCCACGCGCCGCCGGCACTACCAG
 883▸ SerGlyProAlaLeuLeuAlaSerArgValGlyAlaMetAlaThrArgArgArgHisTyrGln
     XhoI
2710  CGCCTCGAGAGCGAGGACCCCGACGCCCTGTAG
 904▸ ArgLeuGluSerGluAspProAspAlaLeu***
```

| | FIG. 2a |
|---|---|
| FIG. 2 | FIG. 2b |

FIG. 2b

```
  1 ATGCTGCTCGCAGCGCTATTGGCGGCGCTGGTCGCCCGGACGACGCTCGGTGCGGACGTGGAC
  1▶ MetLeuLeuAlaAlaLeuLeuAlaAlaLeuValAlaArgThrThrLeuGlyAlaAspValAsp

64 GCCGTGCCCGCGCCGACCTTCCCCCCGCCCGCGTACCCGTACACCGAGTCGTGGCAGCTGACG
 22▶ AlaValProAlaProThrPheProProProAlaTyrProTyrThrGluSerTrpGlnLeuThr

127 CTGACGACGGTCCCCTCGCCCTTCGTCGGCCCCGCGGACGTCTACCACACGCGCCCGCTGGAG
 43▶ LeuThrThrValProSerProPheValGlyProAlaAspValTyrHisThrArgProLeuGlu

190 GACCCGTGCGGGGTGGTGGCGCTGATCTCCGACCCGCAGGTGGACCGGCTGCTGAACGAGGCG
 64▶ AspProCysGlyValValAlaLeuIleSerAspProGlnValAspArgLeuLeuAsnGluAla

253 GTGGCCCACCGGCGGCCCACGTACCGCGCCCACGTGGCCTGGTACCGCATCGCGGACGGGTGC
 85▶ ValAlaHisArgArgProThrTyrArgAlaHisValAlaTrpTyrArgIleAlaAspGlyCys

316 GCACACCTGCTGTACTTTATCGAGTACGCCGACTGCGACCCCAGGCAGGCAGATCTTTGGGCG
106▶ AlaHisLeuLeuTyrPheIleGluTyrAlaAspCysAspProArgGlnAlaAspLeuTrpAla

379 CTGCCGGCGCCGCACCACGCCGATGTGGTGGACCCCGTCCGCGGACTACATGTTCCCCACGGA
127▶ LeuProAlaProHisHisAlaAspValValAspProValArgGlyLeuHisValProHisGly

442 GGACGAGCTGGGGCTGCTCATGGTGGCCCCCGGCGGTTCAACGAGGGCCAGTACCGGCGCCT
148▶ GlyArgAlaGlyAlaAlaHisGlyGlyProArgAlaValGlnArgGlyProValProAlaPro

505 GGTGTCCGTCGACGGCGTGAACATCCTCACCGACTTCATGGTGGCGCTCCCCGAGGGGCAAGA
169▶ GlyValArgArgArgArgGluHisProHisArgLeuHisGlyGlyAlaProArgGlyAlaArg

568 GTGCCCGTTCGCCCGCGTGGACCAGCACCGCACGTACAAGTTCGGCGCGTGCTGGAGCGACGA
190▶ ValProValArgProArgGlyProAlaProHisValGlnValArgArgValLeuGluArgArg

631 CAGCTTCAAGCGGGGCGTGGACGTGATGCGATTCCTGACGCCGTTCTACCAGCAGCCCCCGCA
211▶ GlnLeuGlnAlaGlyArgGlyArgAspAlaIleProAspAlaValLeuProAlaAlaProAla

694 CCCGGGAGGTGGTGAACTACTGGTACCGCAAGAACGGCCGGACGCTCCCGCGGGCCCACGCCGC
232▶ ProGlyGlyGlyGluLeuLeuValProGlnGluArgProAspAlaProAlaGlyProArgArg

757 CGCCACGCCGTACGCCATCGACCCCGCGCGGCCCTCGGCGGGCTCGCCGAGGCCCCGGCCCCG
253▶ ArgHisAlaValArgHisArgProArgAlaAlaLeuGlyGlyLeuAlaGluAlaProAlaPro

820 GCCCCGGCCCCGGCCCCGGCCGAAGCCCGAGCCCGCCCCGGCGACGCCCGCGCCCCCGACCG
274▶ AlaProAlaProAlaProAlaGluAlaArgAlaArgProGlyAspAlaArgAlaProArgPro

883 CCTGCCCGAGCCGGCGACGCGGGACCACGCCGCCGGGGGCCGCCCCACGCCGCGACCCCCGAG
295▶ ProAlaArgAlaGlyAspAlaGlyProArgArgArgGlyProProHisAlaAlaThrProGlu

946 GCCCGAGACGCCGCACCGCCCCTTCGCCCCGCCGGCCGTCGTGCCCAGCGGGTGGCCGCAGCC
316▶ AlaArgAspAlaAlaProProLeuArgProAlaGlyArgArgAlaGlnArgValAlaAlaAla

1009 CGCGGAGCCGTTCCAGCCGCGGACCCCCGCCGCGCCGGGCGTCTCGCGCCACCGCTCGGTGAT
337▶ ArgGlyAlaValProAlaAlaAspProArgArgAlaGlyArgLeuAlaProProLeuGlyAsp
```

FIG. 4a

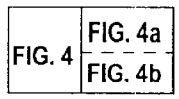

```
1072 CGTCGGCACGGGCACCGCGATGGGCGCGCTCCTGGTGGGCGTGTGCGTCTACATCTTCTTCCG
 358▶ArgArgHisGlyHisArgAspGlyArgAlaProGlyGlyArgValArgLeuHisLeuLeuPro

1135 CCTGAGGGGGCGAAGGGGTATCGCCTCCTGGGCGGTCCCGCGGACGCCGACGAGCTAAAAGC
 379▶ProGluGlyGlyGluGlyValSerProProGlyArgSerArgGlyArgArgArgAlaLysSer

1198 GCAGCCCGGTCCGTAG
 400▶AlaAlaArgSerVal
```

```
  1 ATGGAAGCAAAACTATTCGTATTATTCTGTACATTCACTGCGCTGAAAGCTGACACCATCTGT
  1▸MetGluAlaLysLeuPheValLeuPheCysThrPheThrAlaLeuLysAlaAspThrIleCys

64 GTAGGATACCATGCTAACAATTCCACAGATACTGTCGACACAATACTGGAGAAGAATGTGACT
 22▸ValGlyTyrHisAlaAsnAsnSerThrAspThrValAspThrIleLeuGluLysAsnValThr

127 GTGACTCATTCAGTTAATTTACTAGAAAACAGTCATAATGGAAAACTCTGCAGCCTGAATGGA
 43▸ValThrHisSerValAsnLeuLeuGluAsnSerHisAsnGlyLysLeuCysSerLeuAsnGly

190 GTAGCCCCCTTGCAACTAGGGAAGTGCAACGTAGCAGGGTGGATCCTTGGCAACCCAGAATGT
 64▸ValAlaProLeuGlnLeuGlyLysCysAsnValAlaGlyTrpIleLeuGlyAsnProGluCys

253 GACCTGTTGCTCACAGCGAATTCATGGTCTTACATAATAGAGACTTCAAATTCAGAAAATGGA
 85▸AspLeuLeuLeuThrAlaAsnSerTrpSerTyrIleIleGluThrSerAsnSerGluAsnGly

316 ACATGCTACCCCGGAGAATTCATTGATTATGAGGAATTAAGGGAGCAGCTGAGTTCAGTGTCT
106▸ThrCysTyrProGlyGluPheIleAspTyrGluGluLeuArgGluGlnLeuSerSerValSer

379 TCATTTGAAAGGTTTGAAATTTTCCCAAAAGCAAACTCATGGCCAAATCATGAGACAACCAAA
127▸SerPheGluArgPheGluIlePheProLysAlaAsnSerTrpProAsnHisGluThrThrLys

442 GGTATTACAGCTGCATGCTCTTACTCTGGAACCCCCAGTTTTTATCGGAATTTGCTATGGATA
148▸GlyIleThrAlaAlaCysSerTyrSerGlyThrProSerPheTyrArgAsnLeuLeuTrpIle

505 GTAGAGAGGGAAAATTCCTATCCTAAACTCAGCAAATCATACACAAACAACAAAGGGAAAGAA
169▸ValGluArgGluAsnSerTyrProLysLeuSerLysSerTyrThrAsnAsnLysGlyLysGlu

568 GTGCTTATAATCTGGGGAGTGCACCACCCTCCAACTACCAATGACCAACAAAGCCTCTATCAG
190▸ValLeuIleIleTrpGlyValHisHisProProThrThrAsnAspGlnGlnSerLeuTyrGln

631 AATGCTGATGCATATGTTTCAGTTGGGTCATCAAAATACAACCGAAGGTTCACACCAGAAATA
211▸AsnAlaAspAlaTyrValSerValGlySerSerLysTyrAsnArgArgPheThrProGluIle

694 GCAGCTAGACCTAAAGTCAAAGGACAAGCAGGCAGAATGAATTATTATTGGACATTGTTAGAT
232▸AlaAlaArgProLysValLysGlyGlnAlaGlyArgMetAsnTyrTyrTrpThrLeuLeuAsp

757 CAAGGAGACACCATAACGTTTGAAGCCACTGGGAACTTAATAGCACCATGGTACGCCTTCGCA
253▸GlnGlyAspThrIleThrPheGluAlaThrGlyAsnLeuIleAlaProTrpTyrAlaPheAla

820 TTGAATAAGGGCTCTGGTTCTGGAATTATAACGTCGGATACTCCGGTTCACAATTGTGATACA
274▸LeuAsnLysGlySerGlySerGlyIleIleThrSerAspThrProValHisAsnCysAspThr

883 AAGTGCCAAACCCCTCATGGGGCCTTGAACAGTAGTCTTCCTTTTCAGAACGTACATCCCATC
295▸LysCysGlnThrProHisGlyAlaLeuAsnSerSerLeuProPheGlnAsnValHisProIle

946 ACTATTGGAGAATGCCCCAAATATGTTAAAAGCACCAAACTGAGAATGGCAACAGGACTAAGG
316▸ThrIleGlyGluCysProLysTyrValLysSerThrLysLeuArgMetAlaThrGlyLeuArg

1009 AACGTCCCCTCTATTCAATCCAGAGGACTTTTCGGAGCAATTGCTGGATTCATTGAAGGAGGA
337▸AsnValProSerIleGlnSerArgGlyLeuPheGlyAlaIleAlaGlyPheIleGluGlyGly
```

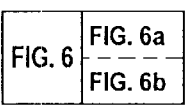

```
1072 TGGACAGGAATGATAGATGGGTGGTATGGGTATCACCATCAGAATGAGCAGGGATCTGGTTAC
 358▸ TrpThrGlyMetIleAspGlyTrpTyrGlyTyrHisHisGlnAsnGluGlnGlySerGlyTyr

1135 GCAGCTGATCAGAAAAGCACACAAATTGCAATTGACGGGATCAGCAACAAAGTGAACTCAGTA
 379▸ AlaAlaAspGlnLysSerThrGlnIleAlaIleAspGlyIleSerAsnLysValAsnSerVal

1198 ATTGAGAAAATGAACACTCAATTCACTGCAGTGGGCAAGGAATTCAATGATCTAGAAAAAAGG
 400▸ IleGluLysMetAsnThrGlnPheThrAlaValGlyLysGluPheAsnAspLeuGluLysArg

1261 ATTGAGAATTTGAATAAGAAAGTCGATGATGGGTTTTTGGATGTTTGGACATATAATGCTGAG
 421▸ IleGluAsnLeuAsnLysLysValAspAspGlyPheLeuAspValTrpThrTyrAsnAlaGlu

1324 TTGCTCGTTTTGCTCGAGAACGAAAGGACTCTAGATTTCCATGACTTTAACGTAAGAAATTTA
 442▸ LeuLeuValLeuLeuGluAsnGluArgThrLeuAspPheHisAspPheAsnValArgAsnLeu

1387 TATGAAAAGGTCAAGTCACAATTGAGAAACAATGCCAAAGAAATCGGGAATGGTTGTTTTGAG
 463▸ TyrGluLysValLysSerGlnLeuArgAsnAsnAlaLysGluIleGlyAsnGlyCysPheGlu

1450 TTCTATCACAAATGTGATGACGAATGCATGAAGAGCGTAAAGAATGGCACATATAACTACCCC
 484▸ PheTyrHisLysCysAspAspGluCysMetLysSerValLysAsnGlyThrTyrAsnTyrPro

1513 AAATATTCAGAAGAATCCAAATTGAATAGAGAGGAAATAGACGGTGTGAAACTAGAATCAATG
 505▸ LysTyrSerGluGluSerLysLeuAsnArgGluGluIleAspGlyValLysLeuGluSerMet

1576 GGAGTTTACCAGATTTTGGCGATCTACTCCACAGTCGCCAGTTCCCTGGTCTTGTTAGTCTCC
 526▸ GlyValTyrGlnIleLeuAlaIleTyrSerThrValAlaSerSerLeuValLeuLeuValSer

1639 CTGGGGGCAATCAGCTTCTGGATGTGTTCTAATGGGTCATTGCAATGCAGAATATGCATTTAA
 547▸ LeuGlyAlaIleSerPheTrpMetCysSerAsnGlySerLeuGlnCysArgIleCysIle•••
```

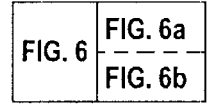

```
  1 ATGGCGTCTCAAGGCACCAAACGATCTTATGAGCAGATGGAAACCGGTGGAGAACGCCAGAAT
  1▸ MetAlaSerGlnGlyThrLysArgSerTyrGluGlnMetGluThrGlyGlyGluArgGlnAsn

64 GCTACTGAAATCAGAGCATCTGTTGGGGGAATGGTTGGTGGAATTGGAAGATTCTACATACAG
 22▸ AlaThrGluIleArgAlaSerValGlyGlyMetValGlyGlyIleGlyArgPheTyrIleGln

127 ATGTGCACTGAACTCAAACTCAGTGACTATGAAGGGAGGCTGATCCAGAACAGCATAACAATA
 43▸ MetCysThrGluLeuLysLeuSerAspTyrGluGlyArgLeuIleGlnAsnSerIleThrIle

190 GAGAGAATGGTTCTCTCTGCATTTGATGAGAGGAGGAACAAATACCTGGAAGAACATCCCAGT
 64▸ GluArgMetValLeuSerAlaPheAspGluArgArgAsnLysTyrLeuGluGluHisProSer

253 GCGGGGAAGGACCCAAAGAAAACTGGAGGTCCAATCTACAGAAAGAGAGACGGAAAATGGATG
 85▸ AlaGlyLysAspProLysLysThrGlyGlyProIleTyrArgLysArgAspGlyLysTrpMet

316 AGAGAGCTGATTCTATATGACAAAGAGGAGATCAGGAGGATTTGGCGTCAAGCAAACAATGGT
106▸ ArgGluLeuIleLeuTyrAspLysGluGluIleArgArgIleTrpArgGlnAlaAsnAsnGly

379 GAAGATGCTACTGCTGGTCTCACTCATCTGATGATTTGGCATTCCAACCTGAATGATGCCACA
127▸ GluAspAlaThrAlaGlyLeuThrHisLeuMetIleTrpHisSerAsnLeuAsnAspAlaThr

442 TATCAGAGAACAAGAGCTCTCGTGCGTACTGGGATGGACCCCAGAATGTGCTCTCTGATGCAA
148▸ TyrGlnArgThrArgAlaLeuValArgThrGlyMetAspProArgMetCysSerLeuMetGln

505 GGATCAACTCTCCCGAGGAGATCTGGAGCTGCTGGTGCGGCAGTAAAGGGAGTTGGGACGATG
169▸ GlySerThrLeuProArgArgSerGlyAlaAlaGlyAlaAlaValLysGlyValGlyThrMet

568 GTAATGGAACTGATTCGGATGATAAAAGCGGGGATCAATGATCGGAACTTCTGGAGAGGCGAA
190▸ ValMetGluLeuIleArgMetIleLysAlaGlyIleAsnAspArgAsnPheTrpArgGlyGlu

631 AATGGACGAAGAACAAGAATTGCATATGAGAGAATGTGCAACATCCTCAAAGGGAAATTTCAG
211▸ AsnGlyArgArgThrArgIleAlaTyrGluArgMetCysAsnIleLeuLysGlyLysPheGln

694 ACAGCAGCGCAACAAGCAATGATGGACCAGGTGCGAGAAATGACAAATCCTGGGAATGCTGAG
232▸ ThrAlaAlaGlnGlnAlaMetMetAspGlnValArgGluMetThrAsnProGlyAsnAlaGlu

757 ACTGAAGACCTTATCTTTCTGGCACGATCTGCACTCATTCTGAGAGGATCAGTGGCTCATAAA
253▸ ThrGluAspLeuIlePheLeuAlaArgSerAlaLeuIleLeuArgGlySerValAlaHisLys

820 TCCTGCCTGCCTGCTTGTGTATATGGACTTGTTGTGGCAAGTGGATATGACTTTGAAAGAGAA
274▸ SerCysLeuProAlaCysValTyrGlyLeuValValAlaSerGlyTyrAspPheGluArgGlu

883 GGGTACTCTCTAGTCGGAATAGATCCTTTCCGTCTGCTCCAAAACAGCCAGGTGTTCAGCCTC
295▸ GlyTyrSerLeuValGlyIleAspProPheArgLeuLeuGlnAsnSerGlnValPheSerLeu

946 ATTAGACCAAATGAGAATCCAGCACATAAGAGTCAGCTGGTATGGATGGCATGCCATTCTGCA
316▸ IleArgProAsnGluAsnProAlaHisLysSerGlnLeuValTrpMetAlaCysHisSerAla

1009 GCATTTGAAGATCTGAGAGTGTCAAGTTTCATCAGAGGGACAAGAGTGGTCCCAAGAGGACAA
337▸ AlaPheGluAspLeuArgValSerSerPheIleArgGlyThrArgValValProArgGlyGln
```

FIG. 8a

| FIG. 8 | FIG. 8a |
|---|---|
| | FIG. 8b |

1072 CTGTCCACCAGAGGAGTTCAAATTGCTTCAAATGAAAACATGGAAACAATGGAGTCCAGTACT
358▶ LeuSerThrArgGlyValGlnIleAlaSerAsnGluAsnMetGluThrMetGluSerSerThr

1135 CTTGAACTGAGAAGCAAATACTGGGCTATAAGAACCAGGAGCGGAGGAAACACCAACCAACAG
379▶ LeuGluLeuArgSerLysTyrTrpAlaIleArgThrArgSerGlyGlyAsnThrAsnGlnGln

1198 AGAGCATCTGCAGGGCAAATCAGTGTACAACTTACTTTCTCGGTACAGAGAAATCTTCCTTTC
400▶ ArgAlaSerAlaGlyGlnIleSerValGlnLeuThrPheSerValGlnArgAsnLeuProPhe

1261 GAGAGAGCGACCATCATGGCAGCATTTACAGGGAACACTGAAGGCAGAACATCTGACATGAGG
421▶ GluArgAlaThrIleMetAlaAlaPheThrGlyAsnThrGluGlyArgThrSerAspMetArg

1324 ACTGAAATTATAAGAATGATGGAAAGTGCCAGACCAGAAGATGTGTCCTTCCAGGGGCGGGGA
442▶ ThrGluIleIleArgMetMetGluSerAlaArgProGluAspValSerPheGlnGlyArgGly

1387 GTCTTCGAGCTCTCGGACGAAAAGGCAACGAACCCGATCGTGCCTTCCTTTGACATGAGTAAT
463▶ ValPheGluLeuSerAspGluLysAlaThrAsnProIleValProSerPheAspMetSerAsn

1450 GAGGGATCTTATTTCTTCGGAGACAATGCAGAGGAGTATGACAATTAA
484▶ GluGlySerTyrPhePheGlyAspAsnAlaGluGluTyrAspAsn•••

```
  1 ATGAAGACTGTCATTGCCTTGAGCTACATTTTCTGTCTGGTTCTTGGCCAAGACCTTCCAGAA
  1▶MetLysThrValIleAlaLeuSerTyrIlePheCysLeuValLeuGlyGlnAspLeuProGlu

64 AATGGCAGCAGCACAGCAAAGCCTGGTCTGGGACATCATGCGGTGCCAAACGGAACGTTAGTG
 22▶AsnGlySerSerThrAlaLysProGlyLeuGlyHisHisAlaValProAsnGlyThrLeuVal

127 AAAACAATCACGAATGATCAGATCGAAGTGACTAATGCTACTGAGCTGGTCCAGAGTTTCTCA
 43▶LysThrIleThrAsnAspGlnIleGluValThrAsnAlaThrGluLeuValGlnSerPheSer

190 ATGGGTAAAATATGCAACAATCCTCATCGAGTTCTTGATGGAGCAAACTGTACACTGATAGAT
 64▶MetGlyLysIleCysAsnAsnProHisArgValLeuAspGlyAlaAsnCysThrLeuIleAsp

253 GCTCTATTGGGGGACCCTCATTGTGATGGCTTTCAAAATGAGAAATGGGACCTTTTCGTTGAA
 85▶AlaLeuLeuGlyAspProHisCysAspGlyPheGlnAsnGluLysTrpAspLeuPheValGlu

316 CGCAGCAAATGCTTCAGCAACTGTTACCCTTATGATGTGCCAGATTATGCCTCCCTTAGGTCA
106▶ArgSerLysCysPheSerAsnCysTyrProTyrAspValProAspTyrAlaSerLeuArgSer

379 CTAATTGCCTCTTCGGGCACTTTGGAGTTTATCAATGAAGGTTTCAATTGGACTGGGGTCACT
127▶LeuIleAlaSerSerGlyThrLeuGluPheIleAsnGluGlyPheAsnTrpThrGlyValThr

442 CAGAACGGAGGAAGCAATGCTTGCAAGAGGGGGCCTGATAGCGGTTTCTTCAGTAGGCTGAAC
148▶GlnAsnGlyGlySerAsnAlaCysLysArgGlyProAspSerGlyPhePheSerArgLeuAsn

505 TGGTTGTACAAATCAGGAAACACATACCCGATGCTGAACGTGACTATGCCAAACAGTGATAAT
169▶TrpLeuTyrLysSerGlyAsnThrTyrProMetLeuAsnValThrMetProAsnSerAspAsn

568 TTTGACAAATTATACATTTGGGGGGTTCACCATCCGAGCACAGACAGGGAACAAACCAACCTA
190▶PheAspLysLeuTyrIleTrpGlyValHisHisProSerThrAspArgGluGlnThrAsnLeu

631 TATGTTCAAGTATCAGGGAAAGCAACGGTTTTCACCAAGAGAAGCCAGCAGACCATAATCCCG
211▶TyrValGlnValSerGlyLysAlaThrValPheThrLysArgSerGlnGlnThrIleIlePro

694 AACAGTCGGTCTAGACCCTGGGTAAGGGGTCTGTCTAGTAGAATAAGCATCCATTGGACAATA
232▶AsnSerArgSerArgProTrpValArgGlyLeuSerSerArgIleSerIleHisTrpThrIle

757 GTTAAACCGGGGACATTCTGATAATTAATAGTAATGGGAACCTAATTGCTCCTCGGGGTTAC
253▶ValLysProGlyAspIleLeuIleIleAsnSerAsnGlyAsnLeuIleAlaProArgGlyTyr

820 TTCAAAATGCACAATGGGAGAAGCTCAATAATGAGGTCAGATGCACCTATTGGCACCTGCAGT
274▶PheLysMetHisAsnGlyArgSerSerIleMetArgSerAspAlaProIleGlyThrCysSer

883 TCTGAATGCATCACTCCAAATGGAAGCATCCCAAATGACAAACCCTTTCAAAACGTAAACAAG
295▶SerGluCysIleThrProAsnGlySerIleProAsnAspLysProPheGlnAsnValAsnLys

946 ATCACATATGGGGCATGTCCTAAGTATGTTAAACAAAACACTCTGAAGTTGGCAACAGGGATG
316▶IleThrTyrGlyAlaCysProLysTyrValLysGlnAsnThrLeuLysLeuAlaThrGlyMet

1009 CGGAATATACCGGAAAAACAAACTAGAGGCATATTCGGCGCAATAGCAGGTTTCATAGAGAAT
337▶ArgAsnIleProGluLysGlnThrArgGlyIlePheGlyAlaIleAlaGlyPheIleGluAsn
```

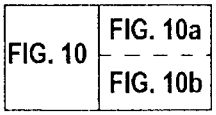

FIG. 10a

1072 GGTTGGGAAGGAATGGTAGACGGCTGGTACGGTTTCAGACATCAAAATTCTGAGGGCACAGGA
358▸ GlyTrpGluGlyMetValAspGlyTrpTyrGlyPheArgHisGlnAsnSerGluGlyThrGly

1135 CAAGCAGCAGACCTTAAAAGCACCCAAGCAGCCATCGACCAAATCAACGGGAAACTGAATAGA
379▸ GlnAlaAlaAspLeuLysSerThrGlnAlaAlaIleAspGlnIleAsnGlyLysLeuAsnArg

1198 CTAATCGAGAAGACGAACGGGAAATTCCATCAAATCGAAAAGGAATTCTCAATAGTAGAAGGG
400▸ LeuIleGluLysThrAsnGlyLysPheHisGlnIleGluLysGluPheSerIleValGluGly

1261 AGAATTCAGGACCTCGAGAAATACGTTGAAGACACTAAAATAGATCTCTGGTCTTACAATGCG
421▸ ArgIleGlnAspLeuGluLysTyrValGluAspThrLysIleAspLeuTrpSerTyrAsnAla

1324 GAACTTCTTGTCGCTCTGGAGAACCAACATACAATTGATCTGACTGACTCGGAAATGAGCAAA
442▸ GluLeuLeuValAlaLeuGluAsnGlnHisThrIleAspLeuThrAspSerGluMetSerLys

1387 CTGTTTGAAAAAACAAGGAGGCAACTGAGGGAAAATGCTGAGGACATGGGAAACGGTTGCCTT
463▸ LeuPheGluLysThrArgArgGlnLeuArgGluAsnAlaGluAspMetGlyAsnGlyCysLeu

1450 CAAATATACCACAAATGTGACAATGCTTGCATAGAGTCAATCAGAAATGGGACTTATGACCAT
484▸ GlnIleTyrHisLysCysAspAsnAlaCysIleGluSerIleArgAsnGlyThrTyrAspHis

1513 AATGAATACAGAGACGAAGCATTAAACAACCGATTTCAGATCAAAGGTGTTGAGCTGAAGTCG
505▸ AsnGluTyrArgAspGluAlaLeuAsnAsnArgPheGlnIleLysGlyValGluLeuLysSer

1576 GGATACAAAGACTGGATCCTGTGGATTTCCTCTGCCATATCATGCTTTTTGCTTTGTGTTGTT
526▸ GlyTyrLysAspTrpIleLeuTrpIleSerSerAlaIleSerCysPheLeuLeuCysValVal

1639 TTGCTAGGATTTATCATGTGGGCCTGCCAGAAAGGCAACATTAGGTGCAACATTTGCATCTGA
547▸ LeuLeuGlyPheIleMetTrpAlaCysGlnLysGlyAsnIleArgCysAsnIleCysIle•••

```
  1 ATGGCGTCTCAAGGCACTAAACGATCTTATGAGCAGATGGAAACCGGTGGAGAACGCCGGAAT
  1▸ MetAlaSerGlnGlyThrLysArgSerTyrGluGlnMetGluThrGlyGlyGluArgArgAsn

64 GCTACTGAAATCAGAGCATCTGTTGGGGGAATGGTTGGTGGAATTGGAAGATTCTACATACAG
 22▸ AlaThrGluIleArgAlaSerValGlyGlyMetValGlyGlyIleGlyArgPheTyrIleGln

127 ATGTGCACTAAACTCAAACTCAGTGACTATGAAGGGAGGCTGATCCAGAACAGCATAACAATA
 43▸ MetCysThrLysLeuLysLeuSerAspTyrGluGlyArgLeuIleGlnAsnSerIleThrIle

190 GAGAGAATGGTTCTCTCTGCATTTGATGAGAGGAGGAACAAATACCTGGAAGAACATCCCAGT
 64▸ GluArgMetValLeuSerAlaPheAspGluArgArgAsnLysTyrLeuGluGluHisProSer

253 GCGGGGAAGGACCCAAAGAAAACTGGAGGTCCAATATACAGAAAGAGAGACGGAAAATGGATG
 85▸ AlaGlyLysAspProLysLysThrGlyGlyProIleTyrArgLysArgAspGlyLysTrpMet

316 AGAGAGCTGATTATGTATGACAAAGAGGAGATCAGGAGGATTTGGCGTCAAGCAAACAATGGT
106▸ ArgGluLeuIleMetTyrAspLysGluGluIleArgArgIleTrpArgGlnAlaAsnAsnGly

379 GAAGATGCTACTGCTGGTCTCACTCATCTGATGATTTGGCATTCCAACCTGAATGATGCCACA
127▸ GluAspAlaThrAlaGlyLeuThrHisLeuMetIleTrpHisSerAsnLeuAsnAspAlaThr

442 TATCAGAGAACAAGAGCTCTCGTGCGTACTGGGATGGACCCCAGAATGTGCTCTCTGATGCAA
148▸ TyrGlnArgThrArgAlaLeuValArgThrGlyMetAspProArgMetCysSerLeuMetGln

505 GGATCAACTCTCCCGAGGAGATCTGGAGCTGCTGGTGCAGCAGTAAAGGGAGTTGGGACGATG
169▸ GlySerThrLeuProArgArgSerGlyAlaAlaGlyAlaAlaValLysGlyValGlyThrMet

568 GTAATGGAACTGATTCGGATGATAAAGCGGGGGATCAATGATCGGAACTTCTGGAGAGGCGAA
190▸ ValMetGluLeuIleArgMetIleLysArgGlyIleAsnAspArgAsnPheTrpArgGlyGlu

631 AATGGACGAAGAACAAGAATTGCATATGAGAGAATGTGCAACATCCTCAAAGGGAAATTTCAG
211▸ AsnGlyArgArgThrArgIleAlaTyrGluArgMetCysAsnIleLeuLysGlyLysPheGln

694 ACAGCAGCGCAACGAGCAACGATGGACCAGGTGCGAGAAAGCAGAAATCCTGGGAATGCTGAG
232▸ ThrAlaAlaGlnArgAlaThrMetAspGlnValArgGluSerArgAsnProGlyAsnAlaGlu

757 ATTGAAGACCTTATCTTTCTAGCACGATCTGCACTCATTCTGAGAGGATCAGTGGCTCATAAA
253▸ IleGluAspLeuIlePheLeuAlaArgSerAlaLeuIleLeuArgGlySerValAlaHisLys

820 TCCTGTCTGCCTGCTTGTGTATATGGACTTGTTGTGGCAAGTGGATATGACTTTGAAAGAGAA
274▸ SerCysLeuProAlaCysValTyrGlyLeuValValAlaSerGlyTyrAspPheGluArgGlu

883 GGGTACTCTCTAGTCGGAATAGATCCTTTCCGTCTGCTCCAGAACAGCCAGGTGTTCAGCCTC
295▸ GlyTyrSerLeuValGlyIleAspProPheArgLeuLeuGlnAsnSerGlnValPheSerLeu

946 ATTAGACCAAATGAGAATCCAGCACATAAGAGTCAGTTGGTATGGATGGCATGCCATTCTGCA
316▸ IleArgProAsnGluAsnProAlaHisLysSerGlnLeuValTrpMetAlaCysHisSerAla

1009 GCATTTGAAGATCTGAGAGTGTCAAGTTTCATCAGAGGGACAAAAGTGGTCCCAAGAGGACAA
337▸ AlaPheGluAspLeuArgValSerSerPheIleArgGlyThrLysValValProArgGlyGln
```

FIG. 12a

| FIG. 12 | FIG. 12a |
|---|---|
| | FIG. 12b |

1072 CTGTCCACTAGAGGAGTTCAAATTGCTTCAAATGAAAACATGGAAACAATGGACTCCATTACT
358▶ LeuSerThrArgGlyValGlnIleAlaSerAsnGluAsnMetGluThrMetAspSerIleThr

1135 CTTGAACTGAGAAGCAAATACTGGGCTATAAGAACCAGGAGCGGAGGAAACACCAACCAACAG
379▶ LeuGluLeuArgSerLysTyrTrpAlaIleArgThrArgSerGlyGlyAsnThrAsnGlnGln

1198 AGGGCATCTGCAGGGCAAATCAGTGTACAACCTACTTTCTCGGTACAGAGAAATCTTCCTTTC
400▶ ArgAlaSerAlaGlyGlnIleSerValGlnProThrPheSerValGlnArgAsnLeuProPhe

1261 GAGAGAGCGACCATCATGGCAGCATTTACAGGGAACACTGAAGGCAGAACATCTGACATGAGG
421▶ GluArgAlaThrIleMetAlaAlaPheThrGlyAsnThrGluGlyArgThrSerAspMetArg

1324 ACTGAAATTATAAGAATGATGGAAAGTGCCAGACCAGAAGATGTGTCCTTCCAGGGGCGGGGA
442▶ ThrGluIleIleArgMetMetGluSerAlaArgProGluAspValSerPheGlnGlyArgGly

1387 GTCTTCGAGCTCTCGGACGAAAAAGCAACGAACCCGATCGTGCCTTCCTTTGACGTGAGTAAT
463▶ ValPheGluLeuSerAspGluLysAlaThrAsnProIleValProSerPheAspValSerAsn

1450 GAGGGATCTTATTTCTTCGGAGACAATGCAGAGGAGTATAACAATTAA
484▶ GluGlySerTyrPhePheGlyAspAsnAlaGluGluTyrAsnAsn•••

| | FIG. 12a |
|---|---|
| FIG. 12b | FIG. 12 |
| | FIG. 12b |

POLYNUCLEOTIDE VACCINE FORMULA AGAINST PORCINE REPRODUCTIVE AND RESPIRATORY PATHOLOGIES

This is a divisional application of application Ser. No. 09/232,468, filed Jan. 15, 1999, now U.S. Pat. No. 6,207,165, which is a continuation-in-part of PCT/FR97/01313 filed Jul. 15, 1997, and designating the U.S. and claiming priority from French Application No. 96/09338, filed Jul. 19, 1996.

Reference is also made to the applications of Audonnet et al., Ser. Nos. 09/232,278, 09/232,479, 09/232,477, 09/232,279, and 09/232,478 and to the application of Rijsewijk et al. Ser. No. 09/232,469, all filed Jan. 15, 1999. All of the above-mentioned applications, as well as all documents cited herein and documents referenced or cited in documents cited herein, are hereby incorporated herein by reference. Vectors of vaccines or immunological compositions of the aforementioned applications, as well as of documents cited herein or documents referenced or cited in documents cited herein or portions of such vectors (e.g., one or more or all of regulatory sequences such as DNA for promoter, leader for secretion, terminator), may to the extent practicable with respect to the preferred host of this application, also be employed in the practice of this invention; and, DNA for vectors of vaccines or immunological compositions herein can be obtained from available sources and knowledge in the art, e.g., GeneBank, such that from this disclosure, no undue experimentation is required to make or use such vectors.

The present invention relates to a vaccine formula allowing in particular the vaccination of pigs against reproductive and respiratory pathologies. It also relates to a corresponding method of vaccination.

During the past decades, the methods for the production of pigs have changed fundamentally. The intensive breeding in an enclosed space has become generalized with, as a corollary, the dramatic development of respiratory pathologies.

The range of symptoms of porcine respiratory pathology is in general grouped under the complex name of pig respiratory disease and involves a wide variety of pathogenic agents comprising viruses as well as bacteria and mycoplasmas.

The principal agents involved in the respiratory disorders are *Actinobacillus pleuropneumoniae,* the infertility and respiratory syndrome virus (PRRS) also called mysterious disease virus, the Aujeszky's disease virus (PRV) and the swine flu virus.

Other viruses cause reproductive disorders leading to abortions, mummifications of the foetus and infertility. The principal viruses are PRRS, the parvovirus and the conventional hog cholera virus (HCV). Secondarily, the swine flu virus PRV and *A. pleuropneumoniae* can also cause such disorders. Deaths may occur with *A. pleuropneumoniae,* HCV and PRV.

In addition, interactions between microorganisms are very important in the porcine respiratory complex. Indeed, most of the bacterial pathogens are habitual hosts of the nasopharangeal zones and of the tonsils in young animals. These pathogens, which are derived from the sows, are often inhaled by the young pigs during their first few hours of life, before the cholostral immunity has become effective. The organisms living in the upper respiratory tract may invade the lower tract when the respiratory defense mechanisms of the host are damaged by a precursor agent such as *A. pleuropneumoniae* or by viruses. The pulmonary invasion may be very rapid, in particular in the case of precursor pathogens such as *A. pleuropneumoniae* which produce potent cytotoxins capable of damaging the cilia of the respiratory epithelial cells and the alveolar macrophages.

Major viral infections, such as influenza, and respiratory coronavirus and Aujeszky's virus infections, may play a role in the pathogenicity of the respiratory complex, besides bacteria with respiratory tropism and mycoplasmas.

Finally, some agents have both a respiratory and a reproductive effect. Interactions may also occur from the point of view of the pathology of reproduction.

It therefore appears to be necessary to try to develop an effective prevention against the principal pathogenic agents involved in porcine reproductive and respiratory pathologies.

The associations developed so far were prepared from inactivated vaccines or live vaccines and, optionally, mixtures of such vaccines. Their development poses problems of compatibility between valencies and of stability. It is indeed necessary to ensure both the compatibility between the different vaccine valencies, whether from the point of view of the different antigens used from the point of view of the formulations themselves, especially in the case where both inactivated vaccines and live vaccines are combined. The problem of the conservation of such combined vaccines and also of their safety especially in the presence of an adjuvant also exists. These vaccines are in general quite expensive.

Patent applications WO-A-90 11092, WO-A-93 19183, WO-A-94 21797 and WO-A-95 20660 have made use of the recently developed technique of polynucleotide vaccines. It is known that these vaccines use a plasmid capable of expressing, in the host cells, the antigen inserted into the plasmid. All the routes of administration have been proposed (intraperitoneal, intravenous, intramuscular, transcutaneous, intradermal, mucosal and the like). Various vaccination means can also be used, such as DNA deposited at the surface of gold particles and projected so as to penetrate into the animals' skin (Tang et al., Nature, 356, 152–154, 1992) and liquid jet injectors which make it possible to transfect at the same time the skin, the muscle, the fatty tissues and the mammary tissues (Furth et al., Analytical Biochemistry, 205, 365–368, 1992). (See also U.S. Pat. Nos. 5,846,946, 5,620, 896, 5,643,578, 5,580,589, 5,589,466, 5,693,622, and 5,703, 055; Science, 259:1745–49, 1993; Robinson et al., seminars in IMMUNOLOGY, 9:271–83, 1997; Luke et al., J. Infect. Dis. 175(1):91–97, 1997; Norman et al., Vaccine, 15(8):801–803, 1997; Bourne et al., The Journal of Infectious Disease, 173:800–7, 1996; and, note that generally a plasmid for a vaccine or immunological composition can comprise DNA encoding an antigen operatively linked to regulatory sequences which control expression or expression and secretion of the antigen from a host cell, e.g., a mammalian cell; for instance, from upstream to downstream, DNA for a promoter, DNA for a eukaryotic leader peptide for secretion, DNA for the antigen, and DNA encoding a terminator.).

The polynucleotide vaccines may also use both naked DNAs and DNAs formulated, for example, inside cationic lipid liposomes.

M-F Le Potier et al., (Second International Symposium on the Eradication of Aujeszky's Disease (pseudorabies) Virus Aug. 6th to 8th 1995 Copenhagen, Denmark) and M. Monteil et al., (Les Journées d'Animation Scientifique du Département de Pathologie Animale [Scientific meeting organized by the department of animal pathology], INRA-ENV, Ecole Nationale Vétérinaire, LYON, Dec. 13–14, 1994) have tried to vaccinate pigs against the Aujeszky's disease virus with the aid of a plasmid allowing the expression of the gD gene under the control of a strong promoter, the type 2 adenovirus major late promoter. In spite of a good antibody response level, no protection could be detected. Now, satisfactory results in the area of protection have been recorded after inoculation of pigs with a recombinant adenovirus into which the gD gene and the same promoter have been inserted, proving that the gD glcyoprotein could be sufficient for inducing protection in pigs.

The prior art gives no protective result in pigs by the polynucleotide vaccination method.

The invention proposes to provide a multivalent vaccine formula which makes it possible to ensure vaccination of pigs against a number of pathogenic agents involved in particular in respiratory pathology and/or in reproductive pathology.

Another objective of the invention is to provide such a vaccine formula combining different valencies while exhibiting all the criteria required for mutual compatibility and stability of the valencies.

Another objective of the invention is to provide such a vaccine formula which makes it possible to combine different valencies in the same vehicle.

Another objective of the invention is to provide such a vaccine formula which is easy and inexpensive to use.

Yet another objective of the invention is to provide such a vaccine formula and a method for vaccinating pigs which makes it possible to obtain protection, including multivalent protection, with a high level of efficiency and of long duration, as well as good safety and an absence of residues.

The subject of the present invention is therefore a vaccine formula in particular against porcine reproductive and/or respiratory pathology, comprising at least 3 polynucleotide vaccine valencies each comprising a plasmid integrating, so as to express it in vivo in the host cells, a gene with one porcine pathogen valency, these valencies being selected from those of the group consisting of Aujeszky's disease virus (PRV or pseudorabies virus), swine flu virus (swine influenza virus, SIV), pig mysterious disease virus (PRRS virus), parvovirosis virus (PPV virus), conventional hog cholera virus (HCV virus) and bacterium responsible for actinobacillosis (*A. pleuropneumoniae*), the plasmids comprising, for each valency, one or more of the genes selected from the group consisting of gB and gD for the Aujeszky's disease virus, HA, NP and N for the swine flu virus, ORF5 (E), ORF3, ORF6 (M) for the PRRS virus, VP2 for the parvovirosis virus, E1, E2 for the conventional hog cholera virus and apxI, apxII and apxIII for *A. pleuropneumoniae*.

Valency in the present invention is understood to mean at least one antigen providing protection against the virus for the pathogen considered, it being possible for the valency to contain, as subvalency, one or more modified natural genes from one or more strains of the pathogen considered.

Pathogenic agent gene is understood to mean not only the complete gene but also the various nucleotide sequences, including fragments which retain the capacity to induce a protective response. The notion of a gene covers the nucleotide sequences equivalent to those described precisely in the examples, that is to say the sequences which are different but which encode the same protein. It also covers the nucleotide sequences of other strains of the pathogen considered, which provide cross-protection or a protection specific for a strain or for a strain group. It also covers the nucleotide sequences which have been modified in order to facilitate the in vivo expression by the host animal but encoding the same protein.

Preferably, the vaccine formula according to the invention will comprise the Aujeszky and porcine flu valencies to which other valencies, preferably selected from the PRRS and *A. pleuropneumoniae* (actinobacillosis) valencies, can be added. Other valencies selected from the parvovirosis and conventional hog cholera valencies can be optionally added to them.

It goes without saying that all the combinations of valencies are possible. However, within the framework of the invention, the Aujeszky and porcine flu, followed by PRRS and *A. pleuropneumoniae,* valencies are considered to be preferred.

From the point of viewing of a vaccination directed more specifically against the porcine respiratory pathology the valencies will be preferably selected from Aujeszky, porcine flu, PRRS and actinobacilosis.

From the point of view of a vaccination directed specifically against the reproductive pathology, the valencies will be preferably selected from PRRS, parvovirosis, conventional hog cholera and Aujeszky.

As regards the Aujeszky valency, either of the gB and gD genes may be used. Preferably, both genes are used, these being in this case mounted in different plasmids or in one and the same plasmid.

As regards the porcine flu valency, the HA and NP genes are preferably used. Either of these two genes or both genes simultaneously can be used, mounted in different plasmids or in one and the same plasmid. Preferably, the HA sequences from more than one influenza virus strain, in particular from the different strains found in the field, will be combined in the same vaccine. On the other hand, NP provides cross-protection and the sequence from a single virus strain will therefore be satisfactory.

As regards the PRSS valency, the E and ORF3 or alternatively M genes are preferably used. These genes can be used alone or in combination; in the case of a combination, the genes can be mounted into separate plasmids or into plasmids combining 2 or 3 of these genes. Genes derived from at least two strains, especially from a European strain and an American strain, will be advantageously combined in the same vaccine.

As regards the conventional hog cholera valency, either of the E1 and E2 genes or also E1 and E2 genes combined, in two different plasmids or optionally in one and the same plasmid, can be used.

As regards the actinobacillosis valency, one of the three genes mentioned above or a combination of 2 or 3 of these genes, mounted in different plasmids or mixed plasmids, may be used in order to provide protection against the different serotypes of *A. pleuropneumoniae*. For the apxI, II and III antigens, it may be envisaged that the coding sequences be modified in order to obtain the detoxified antigens, in particular as in the examples.

The vaccine formula according to the invention can be provided in the form of a dose volume generally of between 0.1 and 10 ml, and in particular between 1 and 5 ml especially for vaccinations by the intramuscular route.

The dose will be generally between 10 ng and 1 mg, preferably between 100 ng and 50 $\mu$g and preferably between 1 $\mu$g and 250 $\mu$g per plasmid type.

Use will preferably be made of naked plasmids simply placed in the vaccination vehicle which will be in general physiological saline (0.9% NaCl), ultrapure water, TE buffer and the like. All the polynucleotide vaccine forms described in the prior art can of course be used.

Each plasmid comprises a promoter capable of ensuring the expression of the gene inserted, under its control, into the host cells. This will be in general a strong eukaryotic promoter and in particular a cytomegalovirus early CMV-IE promoter of human or murine origin, or optionally of another origin such as rats, pigs and guinea pigs.

More generally, the promoter may be either of viral origin or of cellular origin. As viral promoter, there may be mentioned the SV40 virus early or late promoter or the Rous sarcoma virus LTR promoter. It may also be a promoter from the virus from which the gene is derived, for example the gene's own promoter.

As cellular promoter, there may be mentioned the promoter of a cytoskeleton gene, for example the desmin promoter (Belmont et al., Journal of Submicroscopic Cytology and Pathology, 1990, 22, 117–122; and Zhenlin et al., Gene, 1939, 78, 243–254), or alternatively the actin promoter.

When several genes are present in the same plasmid, these may be presented in the same transcription unit or in two different units.

The combination of the different vaccine valencies according to the invention may be preferably achieved by mixing the polynucleotide plasmids expressing the antigen (s) of each valency, but it is also possible to envisage causing antigens of several valencies to be expressed by the same plasmid.

The subject of the invention is also monovalent vaccine formulae comprising one or more plasmids encoding one or more genes from one of the viruses selected from the group consisting of PRV, PRRS, PPV, HCV and *A. pleuropneumoniae,* the genes being those described above. Besides their monovalent character, these formulae may possess the characteristics stated above as regards the choice of the genes, their combinations, the composition of the plasmids, the dose volumes, the doses and the like.

The monovalent vaccine formulae may be used (i) for the preparation of a polyvalent vaccine formula as described above, (ii) individually against the actual pathology, (iii) combined with a vaccine of another type (live or inactivated whole, recombinant, subunit) against another pathology, or (iv) as booster for a vaccine as described below.

The subject of the present invention is in fact also the use of one or more plasmids according to the invention for the manufacture of a vaccine intended to vaccinate pigs first vaccinated by means of a first conventional vaccine of the type in the prior art, namely, in particular, selected from the group consisting of a live whole vaccine, an inactivated whole vaccine, a subunit vaccine, a recombinant vaccine, this first vaccine (monovalent or multivalent) having (that is to say containing or capable of expressing) the antigen(s) encoded by the plasmids or antigen(s) providing cross-protection. Remarkably, the polynucleotide vaccine has a potent booster effect which results in an amplification of the immune response and the acquisition of a long-lasting immunity.

In general, the first-vaccination vaccines can be selected from commercial vaccines available from various veterinary vaccine producers.

The subject of the invention is also a vaccination kit grouping together a first-vaccination vaccine as described above and a vaccine formula according to the invention for the booster. It also relates to a vaccine formula according to the invention accompanied by a leaflet indicating the use of this formula as a booster for a first vaccination as described above.

The subject of the present invention is also a method for vaccinating pigs against the porcine reproductive pathology and/or respiratory pathology, comprising the administration of an effective dose of a vaccine formula as described above. This vaccination method comprises the administration of one or more doses of the vaccine formula, it being possible for these doses to be administered in succession over a short period of time and/or in succession at widely spaced intervals.

The vaccine formulae according to the invention can be administered in the context of this method of vaccination, by the different routes of administration proposed in the prior art for polynucleotide vaccination and by means of known techniques of administration. The vaccination can in particular be used by the intradermal route with the aid of a liquid jet, preferably multiple jet, injector and in particular an injector using an injection head provided with several holes or nozzles, in particular comprising from 5 or 6 holes or nozzles, such as the Pigjet apparatus manufactured and distributed by the company Endoscoptic, Laons, France.

The dose volume for such an apparatus will be reduced preferably to between 0.1 and 0.9 ml, in particular between 0.2 and 0.6 ml and advantageously between 0.4 and 0.5 ml, it being possible for the volume to be applied in one or several, preferably 2, applications.

The subject of the invention is also the method of vaccination consisting in making a first vaccination as described above and a booster with a vaccine formula according to the invention. In a preferred embodiment of the process according to the invention, there is administered in a first instance, to the animal, an effective dose of the vaccine of the conventional, especially inactivated, live, attenuated or recombinant, type, or alternatively a subunit vaccine, so as to provide a first vaccination, and, after a period preferably of 2 to 6 weeks, the polyvalent or monovalent vaccine according to the invention is administered.

The invention also relates to the method of preparing the vaccine formulae, namely the preparation of the valencies and mixtures thereof, as evident from this description.

The invention will now be described in greater detail with the aid of the embodiments of the invention taken with reference to the accompanying drawings.

BRIEF DESCRIPTION OF THE DRAWINGS

FIG. 2: Sequence of the PRV gB gene (NIA3 strain)

FIG. 6: Sequence of the porcine flu HA gene (H1N1 strain)

FIG. 8: Sequence of the porcine flu NP gene (H1N1 strain)

FIG. 10: Sequence of the porcine flu HA gene (H3N2 strain)

FIG. 12: Sequence of the porcine flu NP gene (H3N2 strain)

FIG. 13: Construction of the plasmid pPB132

FIG. 14: Plasmid pAB025

FIG. 15: Plasmid pAB001

FIG. 16: Plasmid pAB091

FIG. 17: Plasmid pAB092

FIG. 18: Plasmid pAB004

FIG. 19: Plasmid pAB069

FIG. 20: Plasmid pAB061

EXAMPLES

Example 1

Culture of the Viruses

The viruses are cultured on the appropriate cellular system until a cytopathic effect is obtained. The cellular systems to be used for each virus are well known to persons skilled in the art. Briefly, the cells sensitive to the virus used, which are cultured in Eagle's minimum essential medium (MEM medium) or another appropriate medium, are inoculated with the viral strain studied using a multiplicity of infection of 1. The infected cells are then incubated at 37° C. for the time necessary for the appearance of a complete cytopathic effect (on average 36 hours).

Example 2

Culture of the Bacteria and Extraction of the Bacterial DNA

The *Actinobacillus pleuropneumoniae* strains were cultured as described by A. Rycroft et al. (J. Gen. Microbiol., 1991, 137, 561–568). The high-molecular weight DNA (chromosomal DNA) was prepared according to the standard techniques described by J. Sambrook et al. (*Molecular Cloning: A Laboratory Manual,* 2nd Edition, Cold Spring Harbor Laboratory, Cold Spring Harbor, N.Y., 1989).

Example 3

Extraction of the Viral Genomic DNAs

After culturing, the supernatant and the lysed cells are harvested and the entire viral suspension is centrifuged at 1000 g for 10 minutes at +4° C. so as to remove the cellular debris. The viral particles are then harvested by ultracentrifugation at 400,000 g for 1 hour at +4° C. The pellet is taken up in a minimum volume of buffer (10 mM Tris, 1 mM EDTA; pH 8.0). This concentrated viral suspension is treated with proteinase K (100 $\mu$g/ml final) in the presence of sodium dodecyl sulphate (SDS) (0.5% final) for 2 hours at 37° C. The viral DNA is then extracted with a phenol/chloroform mixture and then precipitated with 2 volumes of absolute ethanol. After leaving overnight at −20° C., the DNA is centrifuged at 10,000 g for 15 minutes at +4° C. The DNA pellet is dried and then taken up in a minimum volume of sterile ultrapure water. It can then be digested with restriction enzymes.

Example 4

Isolation of the Viral Genomic RNAs

The RNA viruses were purified according to techniques well known to persons skilled in the art. The genomic viral RNA of each virus was then isolated using the "guanidium thiocyanate/phenol-chloroform" extraction technique described by P. Chromczynski and N. Sacchi (Anal. Biochem., 1987, 162, 156–159).

Example 5
Molecular Biology Techniques

All the constructions of plasmids were carried out using the standard molecular biology techniques described by J. Sambrook et al. (*Molecular Cloning: A Laboratory Manual*, 2nd Edition, Cold Spring Harbor Laboratory, Cold Spring Harbor, N.Y., 1989). All the restriction fragments used for the present invention were isolated using the "Geneclean" kit (BIO 101 Inc. La Jolla, Calif.).

Example 6
RT-PCR Technique

Specific oligonucleotides (comprising restriction sites at their 5' ends to facilitate the cloning of the amplified fragments) were synthesized such that they completely cover the coding regions of the genes which are to be amplified (see specific examples). The reverse transcription (RT) reaction and the polymerase chain reaction (PCR) were carried out according to standard techniques (J. Sambrook et al., *Molecular Cloning: A Laboratory Manual*, 2nd Edition, Cold Spring Harbor Laboratory, Cold Spring Harbor, N.Y., 1989). Each RT-PCR reaction was performed with a pair of specific amplimers and taking, as template, the viral genomic RNA extracted. The complementary DNA amplified was extracted with phenol/chloroform/isoamyl alcohol (25:24:1) before being digested with restriction enzymes.

Example 7
Plasmid pVR1012

Figure 1:
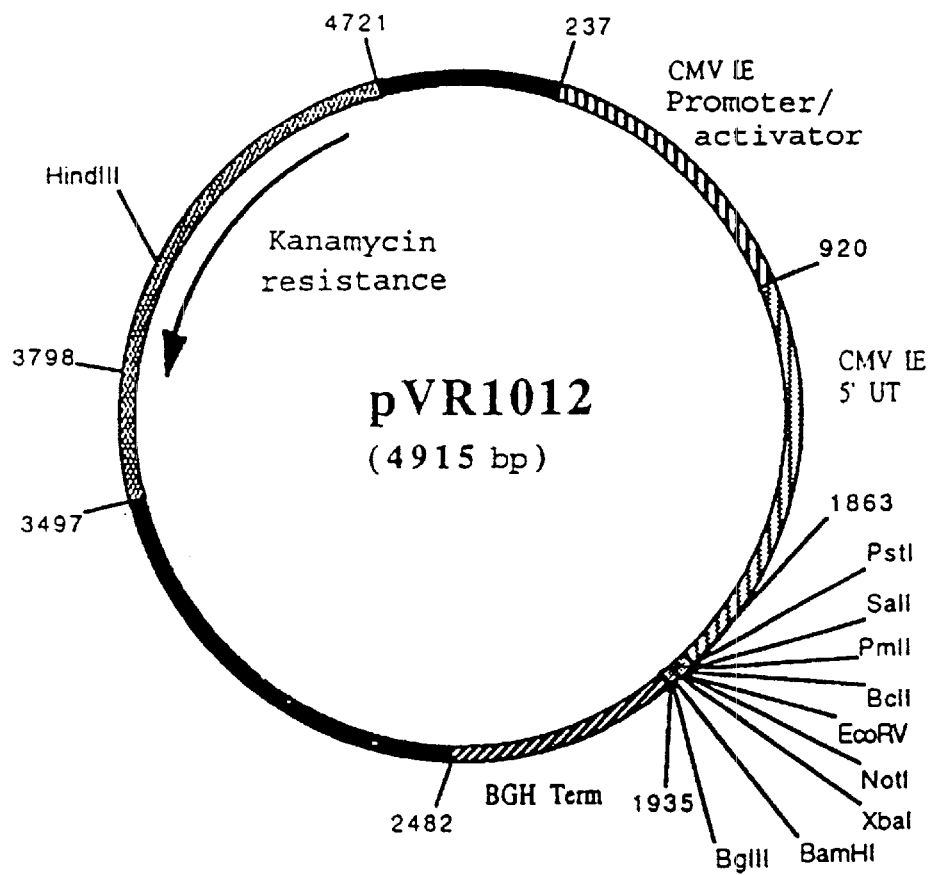
FIG. 1: Plasmid pVR102
Figure 3:
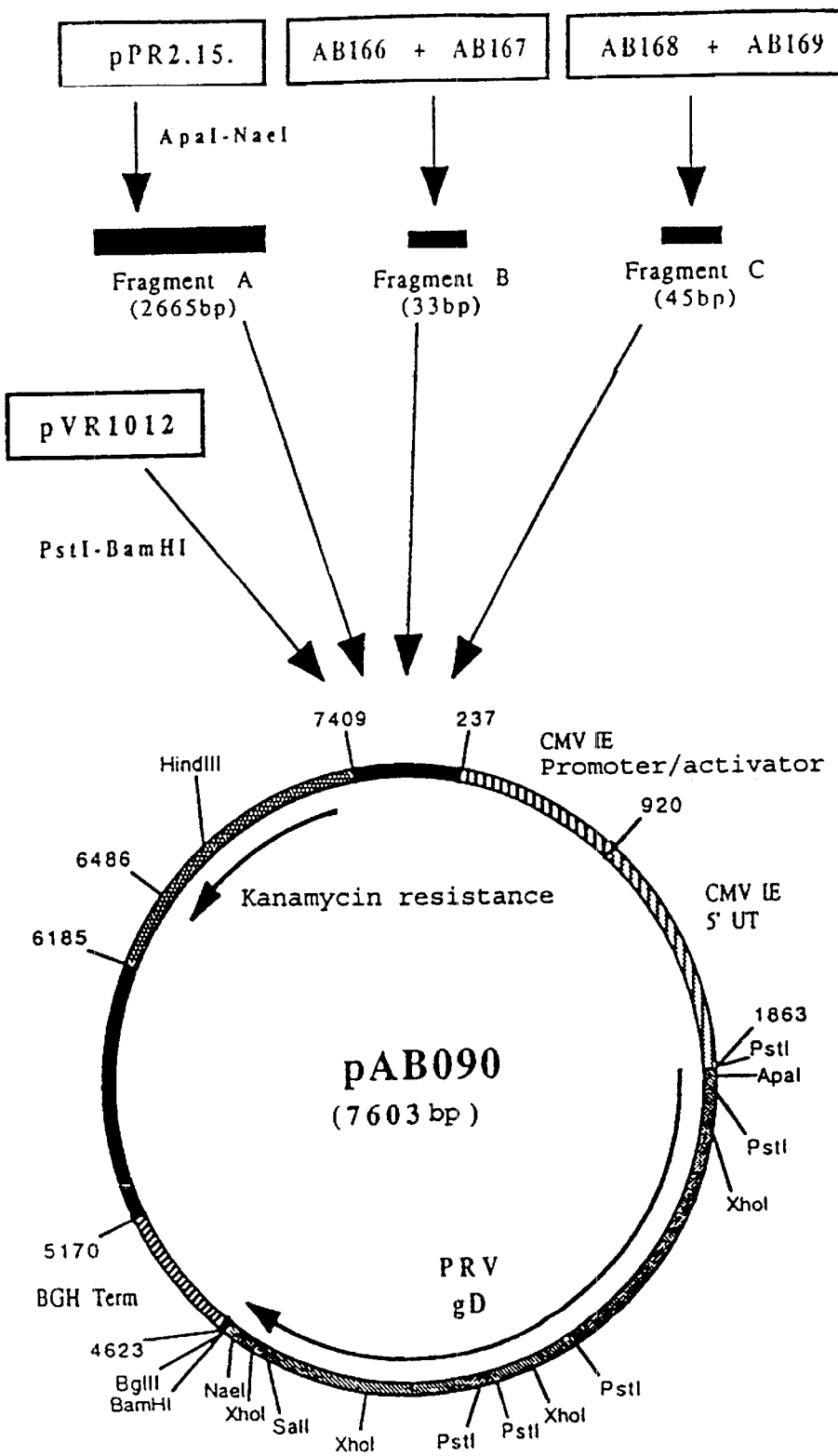
FIG. 3: Construction of the plasmid pAB090
Figures 4, 4B:
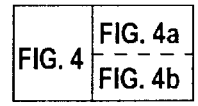
FIG. 4: Sequence of the PRV gD gene (NIA3 strain)
Figure 5:
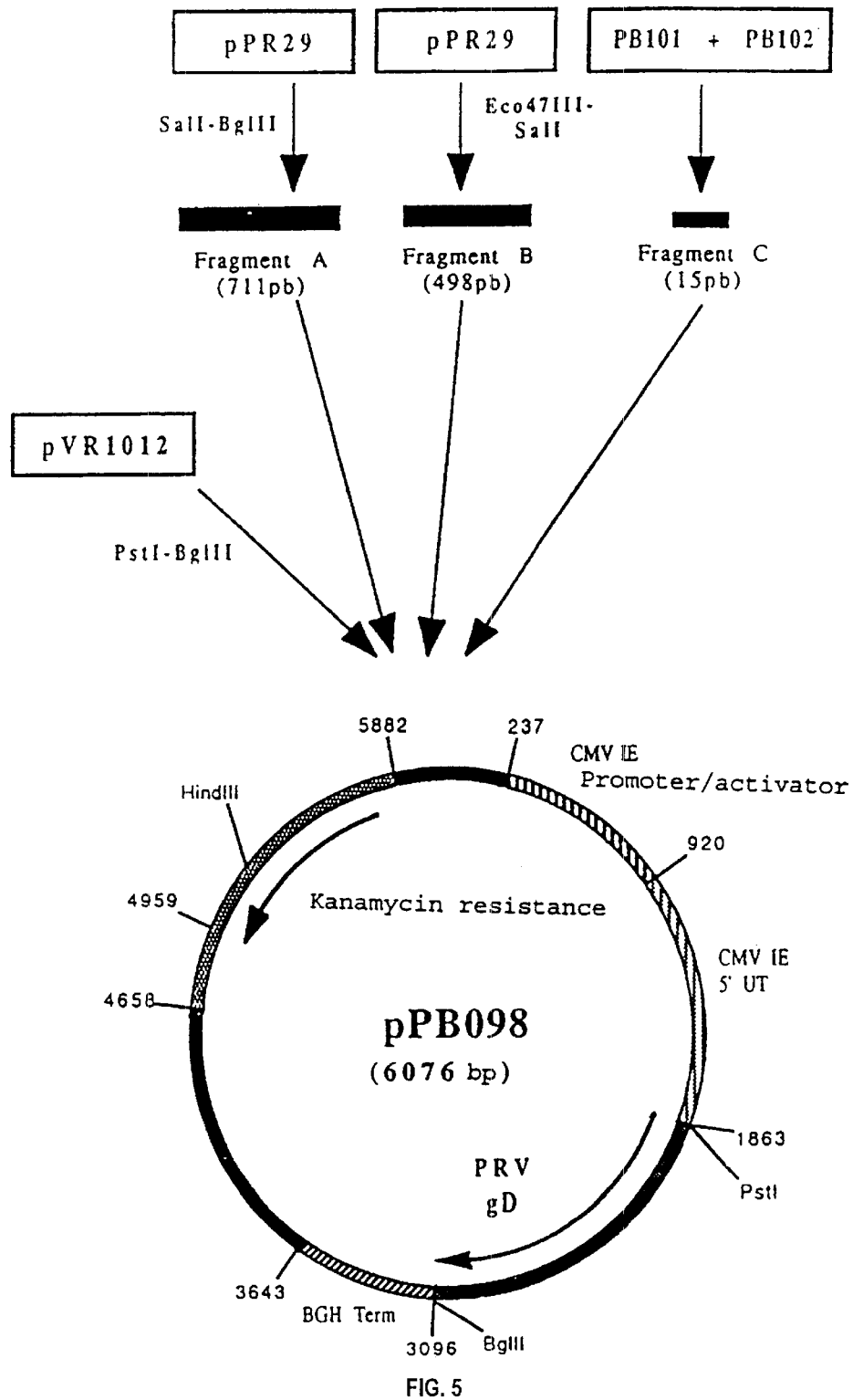
FIG. 5: Construction of the plasmid pPB098
Figure 7:
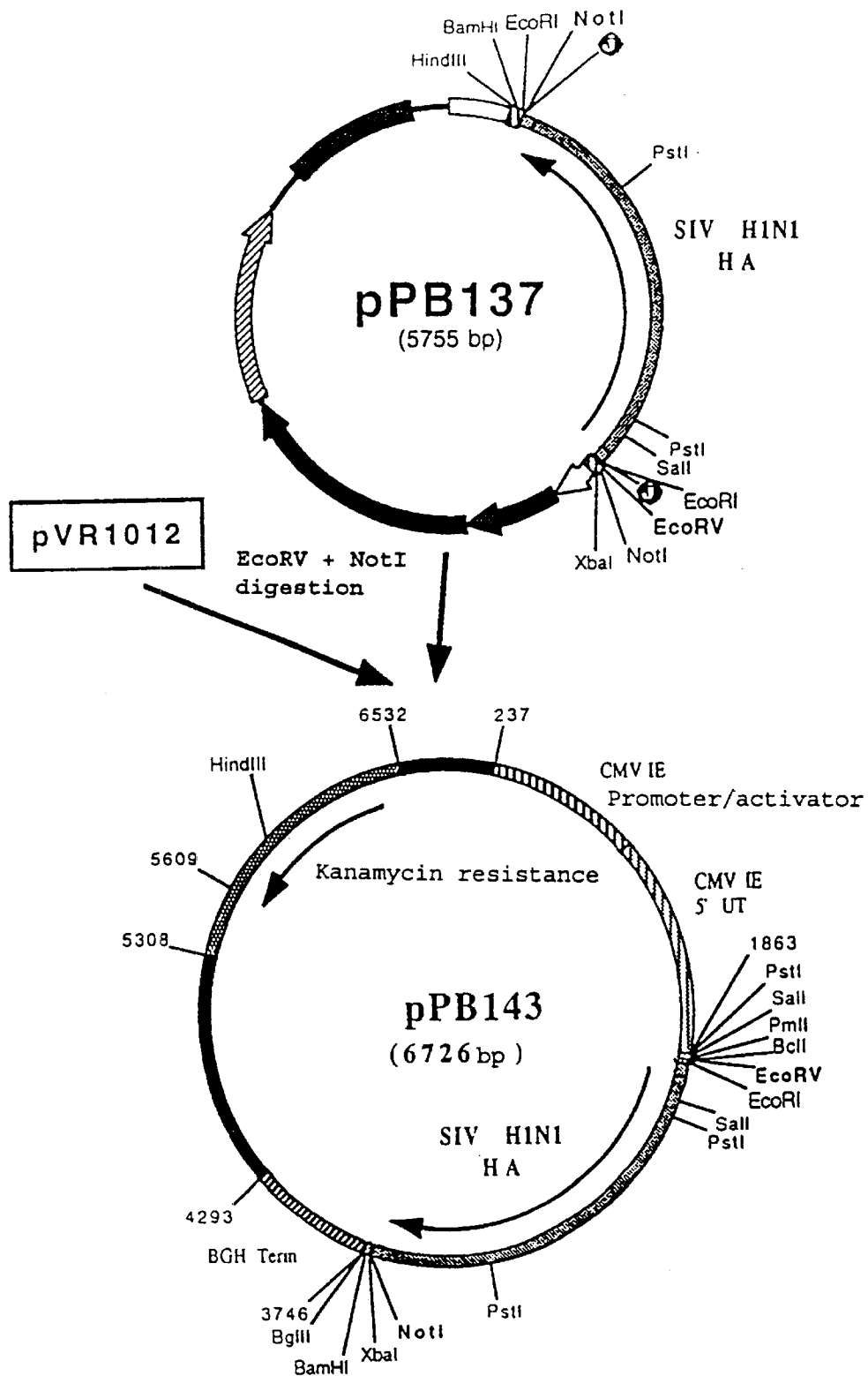
FIG. 7: Construction of the plasmid pPB143

The plasmid pVR1012 (FIG. 1) was obtained from Vical Inc., San Diego, Calif., USA. Its construction has been described in J. Hartikka et al. (Human Gene Therapy, 1996, 7, 1205–1217).

Example 8
Construction of the Plasmid pAB090 (PRV gB Gene)

The plasmid pPR2.15 (M. Riviere et al., J. Virol., 1992, 66, 3424–3434) was digested with ApaI and NaeI in order to release a 2665 bp ApaI-NaeI fragment (Fragment A) containing the gene encoding Aujeszky's disease virus (NIA3 strain) gB glycoprotein (FIG. 2 and SEQ ID NOS: 1 and 49)

By hybridizing the following 2 oligonucleotides:

AB166 (33 mer) (SEQ ID No. 2)

5' GATGCCCGCTGGTGGCGGTCTTTGGCGCGGGCC 3'

AB167 (33 mer) (SEQ ID No. 3)

5' ACGTCTACGGGCGACCACCGCCAGAAACCGCGC 3' a 33 bp fragment containing the sequence of the gD gene, from the initial ATG codon up to the ApaI site, was reconstructed, with the creation of a PstI site in 5' (fragment B).

By hybridizing the following 2 oligonucleotides:

AB168 (45 mer) (SEQ ID No. 4)

5' GGCACTACCAGCGCCTCGAGAGCGAG-GACCCCGACGCCCTGTAGG 3'

AB169 (49 mer) (SEQ ID No. 5)

5' GATCCCTACAGGGCGTCGGGGTC-CTCGCTCTCGAGGCGCTGGTAGTGCC 340 a 45 bp fragment containing the sequence of the gD gene, from the NaeI site to the TAG stop codon was reconstructed, with the creation of a BamHI site in 3' (fragment C).

The fragments A, B and C were ligated together into the vector pVR1012 (Example 7), previously digested with PstI and BamHI, to give the plasmid pAB090 (7603 bp) (FIG. 3).

Example 9

Construction of the Plasmid pPB098 (PRV gD Gene)

The plasmid pPR29 (M. Riviere et al., J. Virol., 1992, 66, 3424–3434) was digested with SalI and BglII in order to liberate a 711 bp SalI-BglII fragment (fragment A) containing the 3' part of the gene encoding the Aujeszky's disease virus (NIA3 strain) gD glycoprotein (FIG. 4 and SEQ ID NOS: 6 and 50).

The plasmid pPR29 was digested with Eco47III and SalI in order to liberate a 498 bp Eco47III-SalI fragment containing the 5' part of the gene encoding the Aujeszky's disease virus (NIA3 strain) gD glycoprotein (fragment B).

By hybridizing the following 2 oligonucleotides:

PB101 (15 mer) (SEQ ID No. 7)

5' GATGCTGCTCGCAGC 3'

PB102 (19 mer) (SEQ ID No. 8)

5' GCTGCGAGCAGCATCTGCA 3' a 15 bp fragment containing the 5' sequence of the gD gene, from the initial ATG codon up to the Eco47III site was reconstructed, with the creation of a PstI site in 5' (fragment C).

After purification, the fragments A, B and C were ligated together into the vector pVR1012 (Example 7), previously digested with PstI and BglII, to give the plasmid pPB098 (6076 bp) (FIG. 5).

Example 10

Construction of the Plasmid pBP143 (Porcine Flu HA Gene, H1N1 Strain)

An RT-PCR reaction according to the technique described in Example 6 was carried out in the porcine flu virus (SIV, H1N1 "SW" strain) genomic RNA, prepared according to the technique described in Example 4, and with the following oligonucleotides:

PB1107 (32 mer) (SEQ ID No. 9)

5' GTTCTGCAGCACCCGGGAGCAAAAGCAGGGGA 3'

PB108 (33 mer) (SEQ ID No. 10)

5' ATTGCGGCCGCTAGTAGAAACAAGGGTGTTTTT 3' so as to precisely isolate the gene encoding the HA protein from SIV H1N1 (FIG. 6 and SEQ ID NOS. 11 and 51) in the form of a 1803 bp PCR fragment. After purification, this fragment was ligated with the vector PCRII-direct (Invitrogen Reference K2000-01), to give the vector pPB137 (5755 bp). The vector pPB137 was digested with EcoRV and NotI in order to liberate a 1820 bp EcoRV-NotI fragment containing the HA gene. This fragment was then ligated into the vector pVR1012 (Example 7), previously digested with EcoRV and NotI, to give the plasmid pPB143 (6726 bp) (FIG. 7).

Example 11

Construction of the Plasmid pPB142 (Porcine Flu NP Gene, H1N1 Strain)

An RT-PCR reaction according to the technique described in Example 6 was carried out with the porcine flu virus (SIV H1N1 "SW" strain) genomic RNA, prepared according to the technique described in Example 4, and with the following oligonucleotides:

PB097 (36 mer) (SEQ ID No. 12)

5' CCGGTCGACCGGGATAATCACTCACT-GAGTGACATC 3'

PB098 (33 mer) (SEQ ID No. 13)

5' TTGCGGCCGCTGTAGAAACAAGGGTATTTTTCT 3' so as to precisely isolate the gene encoding the NP protein from SIV H1N1 (FIG. 8 and SEQ ID NOS. 14 and 52) in the form of an SalI-NotI fragment. After purification, the 1566 bp RT-PCR product was ligated with the vector PCRII-direct (Invitrogen Reference K2000-01), to give the vector pPB127 (5519 bp).

Figure 9:
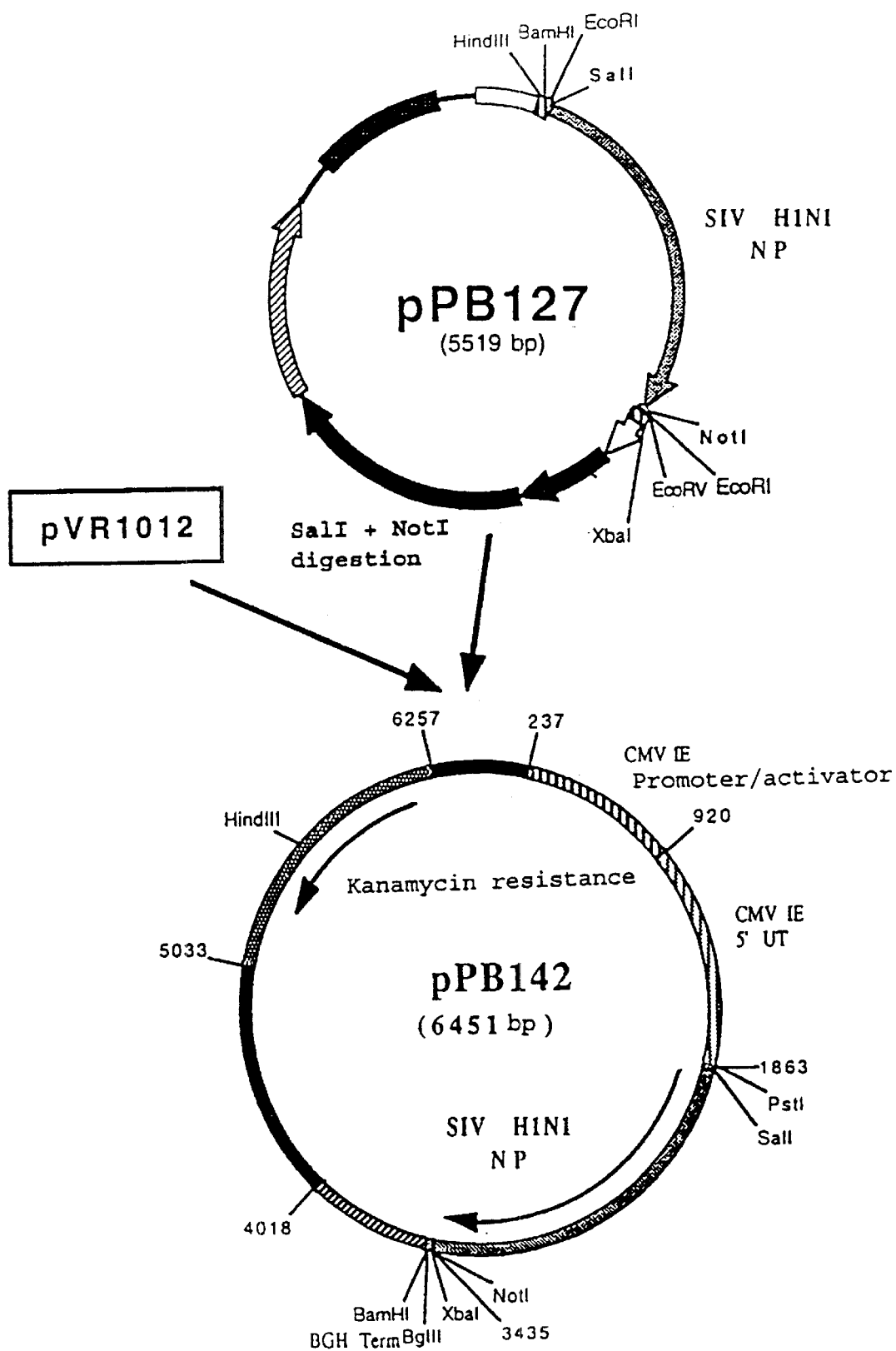
FIG. 9: Construction of the plasmid pPB42

The vector pPB127 was digested with SalI and NotI in order to liberate a 1560 bp SalI-NotI fragment containing the NP gene. This fragment was then ligated into the vector pVR1012 (Example 7), previously digested with SalI and NotI, to give the plasmid pPB142 (6451 bp) (FIG. 9).

Example 12
Construction of the Plasmid pPB144 (Porcine Flu HA Gene, H3N2 Strain)

An RT-PCR reaction according to the technique described in Example 6 was carried out with the porcine flu virus (strain SIV H3N2 Cotes du Nord 1987) genomic RNA, prepared according to the technique described in Example 4, and with the following oligonucleotides:
PB095 (31 mer) (SEQ ID No. 15)
5' GTTCTGCAGGCAGGGGATAATTCTATCAACC 3'
PB096 (36 mer) (SEQ ID No. 16)
5' TTGCGGCCGCAAGGGTGTTTTAATTAC-TAATATAC 3'
so as to precisely isolate the gene encoding the HA protein from SIV H3N2 (FIG. 10 and SEQ ID NOS: 17 and 53) in the form of a PstI-NotI fragment. After purification, the 1765 bp RT-PCR product was ligated with the vector PCRII-direct (Invitrogen Reference K2000-01) to give the vector pPB120 (5716 bp).

Figure 11:
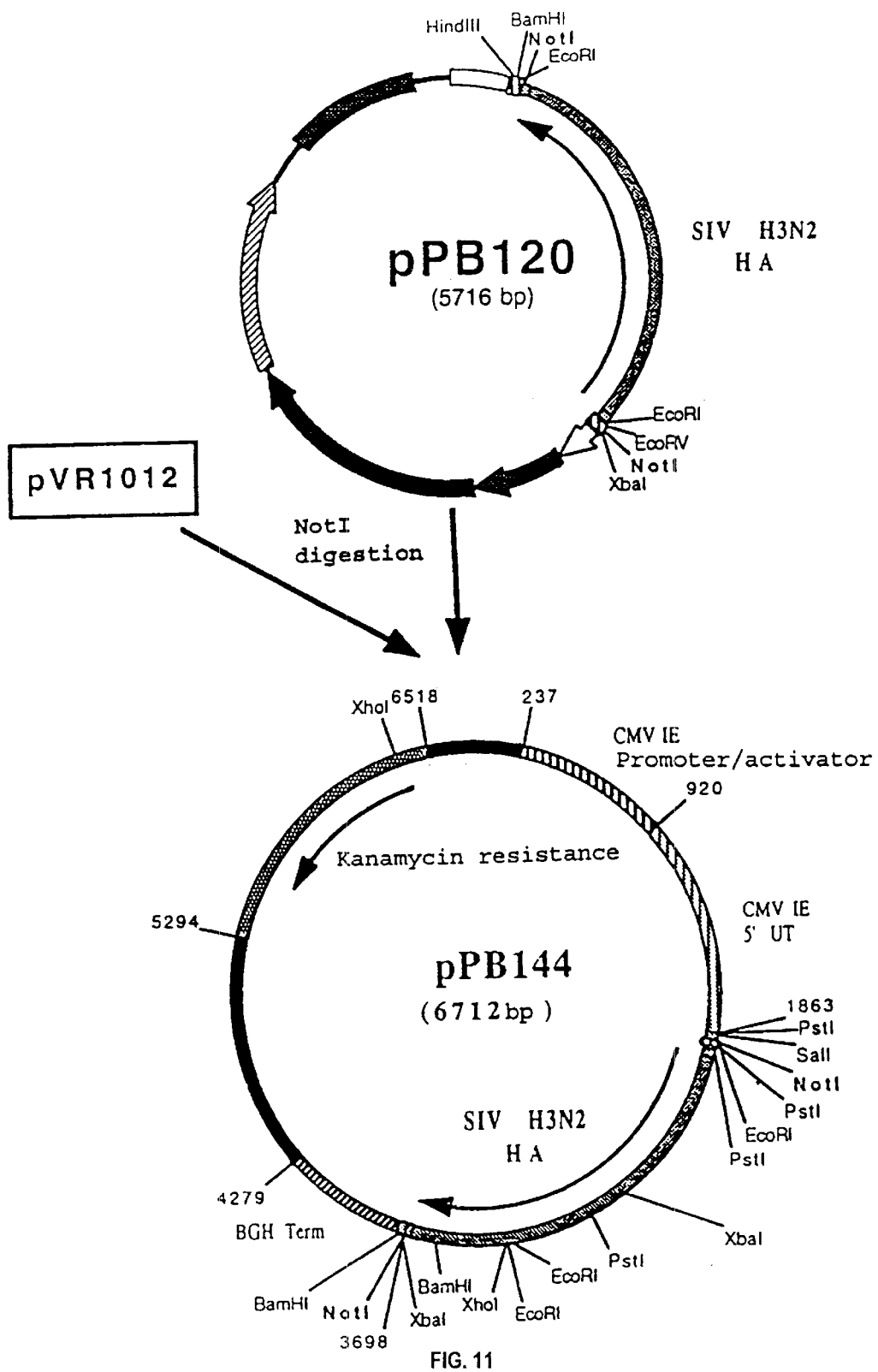
FIG. 11: Construction of the plasmid pPB144

The vector pPB120 was digested with NotI in order to liberate a 1797 bp NotI-NotI fragment containing the HA gene. This fragment was then ligated into the vector pVR1012 (Example 7), previously digested with NotI, to give the plasmid pPB144 (6712 bp) containing the H3N2 HA gene in the correct orientation relative to the promoter (FIG. 11).

Example 13
Construction of the Plasmid pPB132 (Porcine Flu NP Gene, H3N2 Strain)

An RT-PCR reaction according to the technique described in Example 6 was carried out with the porcine flu virus (strain SIV H3 N2 Cotes du Nord 1987) genomic RNA, prepared according to the technique described in Example 4, and with the following oligonucleotides:
PB097 (36 mer) (SEQ ID No. 12)
5' CCGGTCGACCGGGATAATCACTCACT-GAGTGACATC 3'
PB098 (33 mer) (SEQ ID No. 13)
5' TTGCGGCCGCTGTAGAAACAAGGGTATTTTTCT 3'
so as to precisely isolate the gene encoding the NP protein from SIV H3N2 (FIG. 12 and SEQ ID NOS. 18 and 54) in the form of a SalI-NotI fragment. After purification, the 1564 bp RT-PCR product was ligated with the vector PCRII-direct (Invitrogen Reference K2000-01) in order to give the vector pPB123 (5485 bp).

Figure 13:
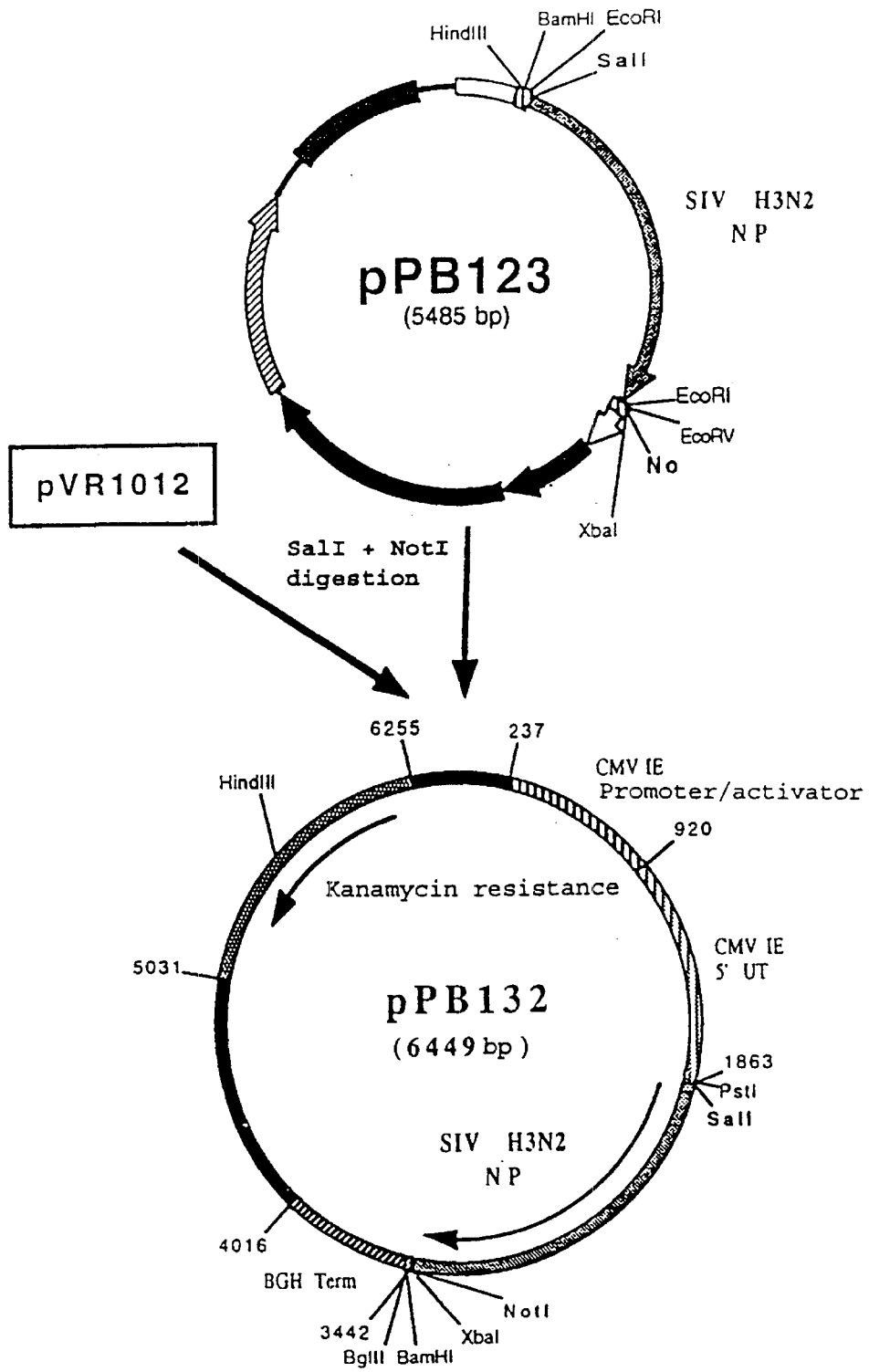

The vector pPB123 was digested with SalI and NotI in order to liberate a SalI-NotI fragment of 1558 bp containing the NP gene. This fragment was then ligated into the vector pVR1012 (Example 7), previously digested with SalI and NotI, to give the plasmid pPB132 (6449 bp) (FIG. 13).

Example 14
Construction of the Plasmid pAB025 (PRRSV ORF5 Gene, Lelystad Strain)

Figure 14:
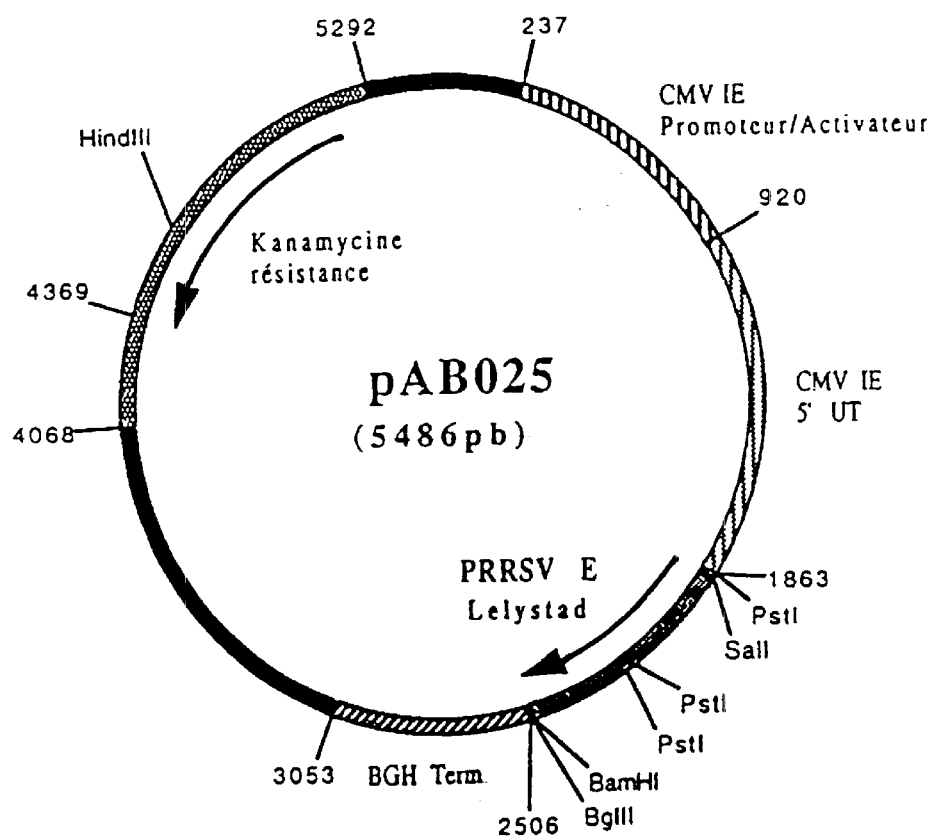

An RT-PCR reaction according to the technique described in Example 6 was carried out with the PRRSV virus (Lelystad strain) genomic RNA (J. Meulenberg et al., Virology, 1993, 19, 62–72), prepared according to the technique described in Example 4, and with the following oligonucleotides:
AB055 (34 mer) (SEQ ID No. 19)
5' ACGCGTCGACAATATGAGATGTTCTCACAAATTG 3'
AB056 (33 mer) (SEQ ID No. 20)
5' CGCGGATCCCGTCTAGGCCTCCCATTGCTCAGC 3'
so as to precisely isolate the "ORF5" gene encoding the envelope glycoprotein E (gp25) from the PRRS virus, Lelystad strain. After purification, the 630 bp RT-PCR product was digested with SalI and BamHI in order to isolate a 617 bp SalI-BamHI fragment. This fragment was ligated with the vector pVR1012 (Example 7), previously digested with SalI and BamHI, to give the plasmid pAB025 (5486 bp) (FIG. 14).

Example 15
Construction of the plasmid pAB001 (PRRSV ORF5 Gene, USA Strain)

Figure 15:
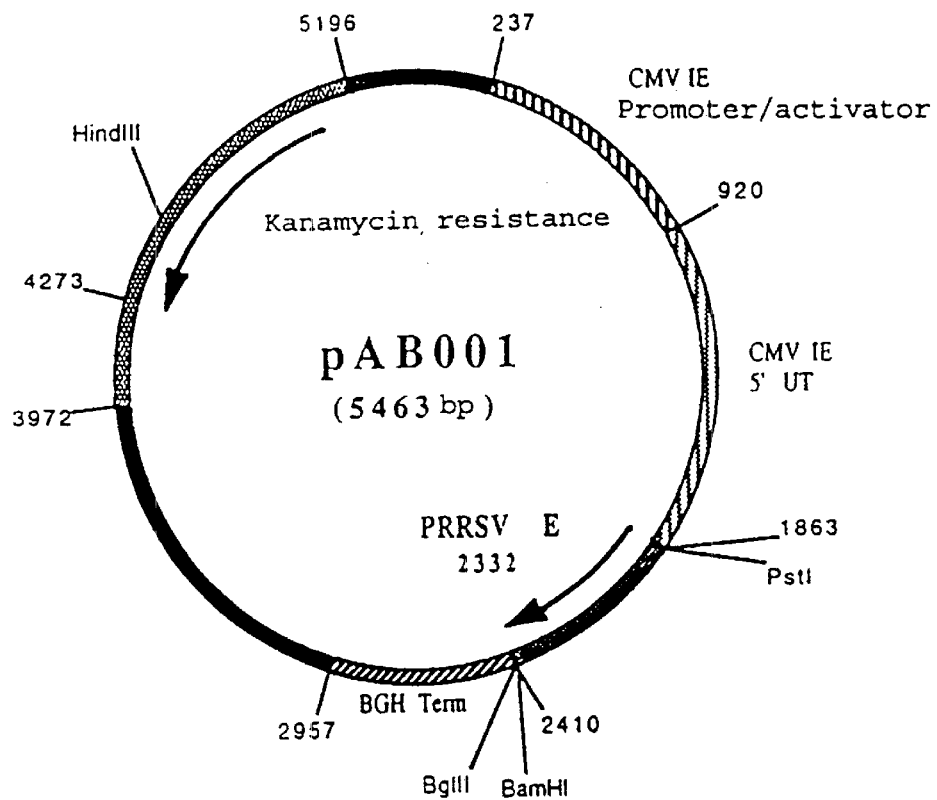

An RT-PCR reaction according to the technique described in Example 6 was carried out with the PRRSV virus (ATCC VR2332 strain) genomic RNA (M. Murtaugh et al., Arch Virol., 1995, 140, 1451–1460), prepared according to the technique described in Example 4, and with the following oligonucleotides:
AB001 (30 mer) (SEQ ID No. 21)
5' AACTGCAGATGTTGGAGAAATGCTTGACCG 3'
AB002 (30 mer) (SEQ ID No. 22)
5' CGGGATCCCTAAGGACGACCCCATTGTTCC 3'
so as to precisely isolate the gene encoding the envelope glycoprotein E("gp25") from the PRRS virus, ATCC-VR2332 strain. After purification, the 620 bp RT-PCR product was digested with PstI and BamHI in order to isolate a 606 bp PstI-BamHI fragment. This fragment was ligated with the vector pVR1012 (Example 7), previously digested with PstI and BamHI, to give the plasmid pAB001 (5463 bp) (FIG. 15).

Example 16
Construction of the Plasmid pAB091 (PPRSV ORF3 gene, Lelystad Strain)

Figure 16:
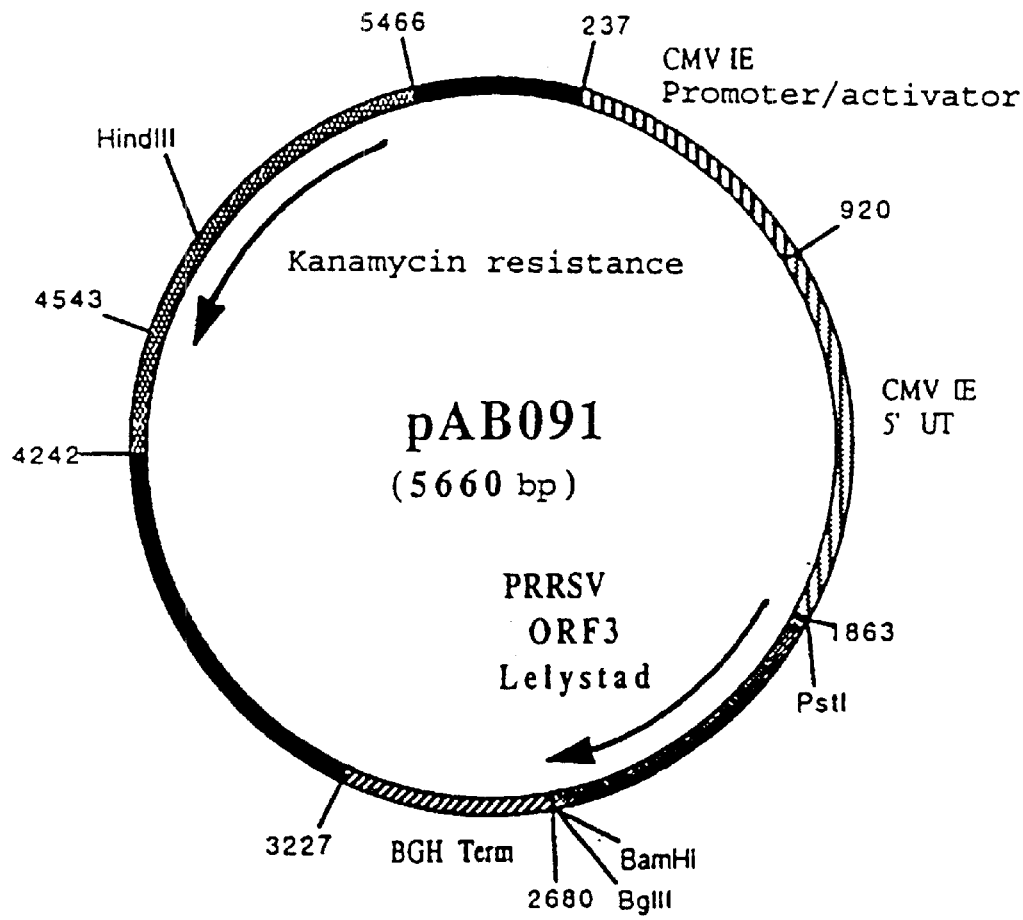
Figure 17:
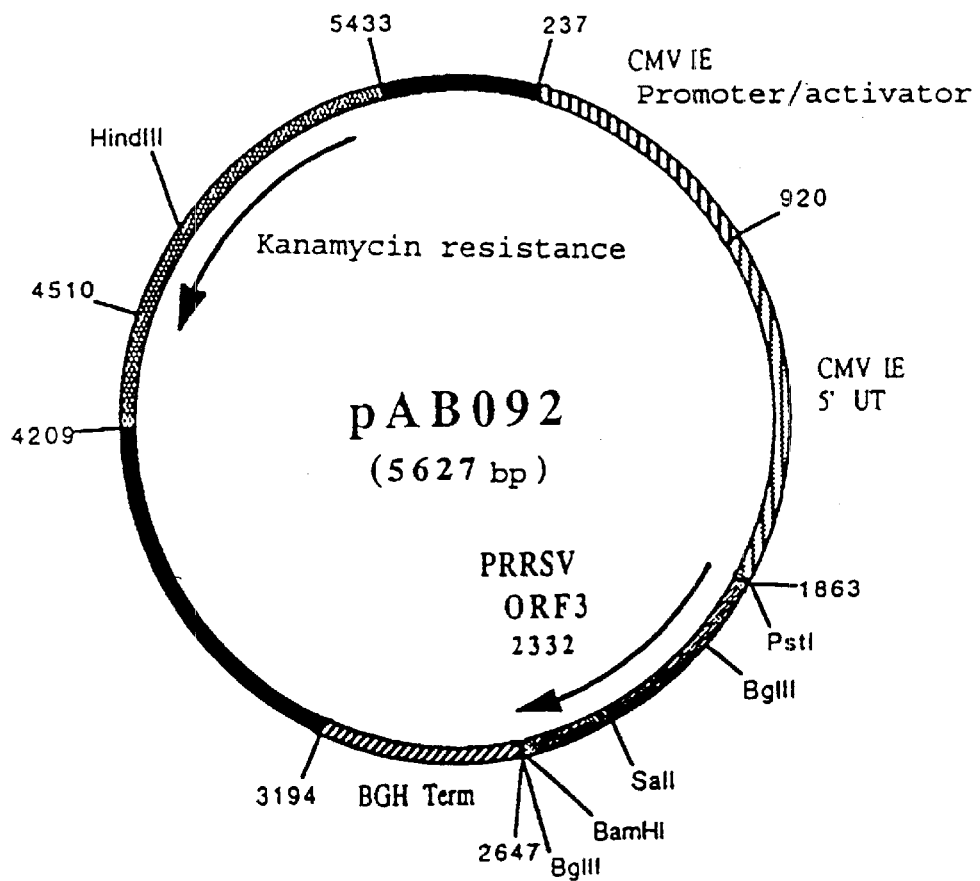
Figure 18:
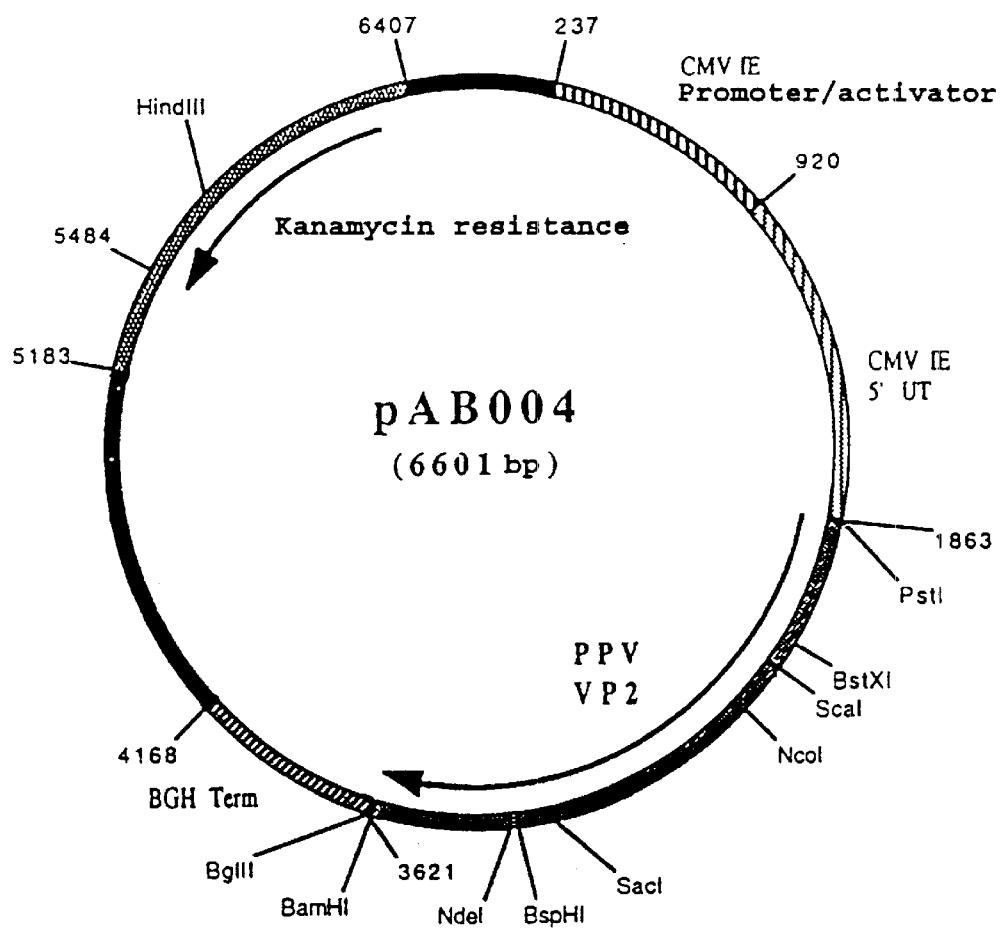
Figure 19:
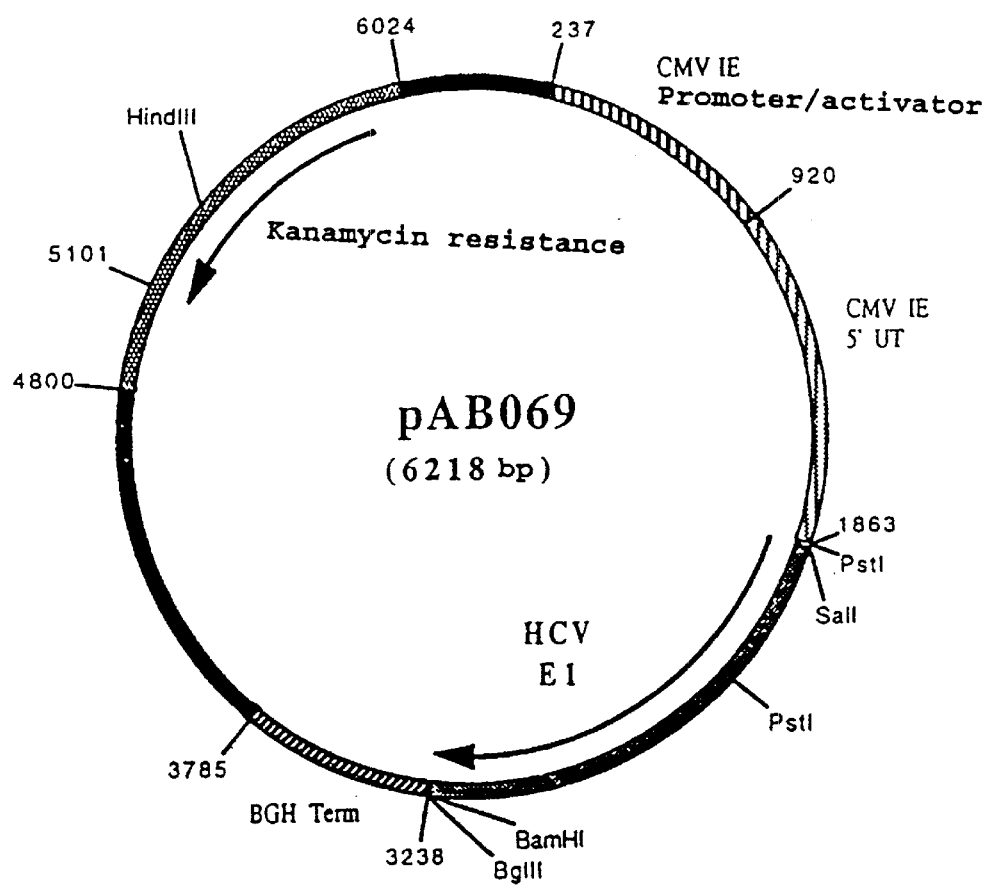
Figure 20:
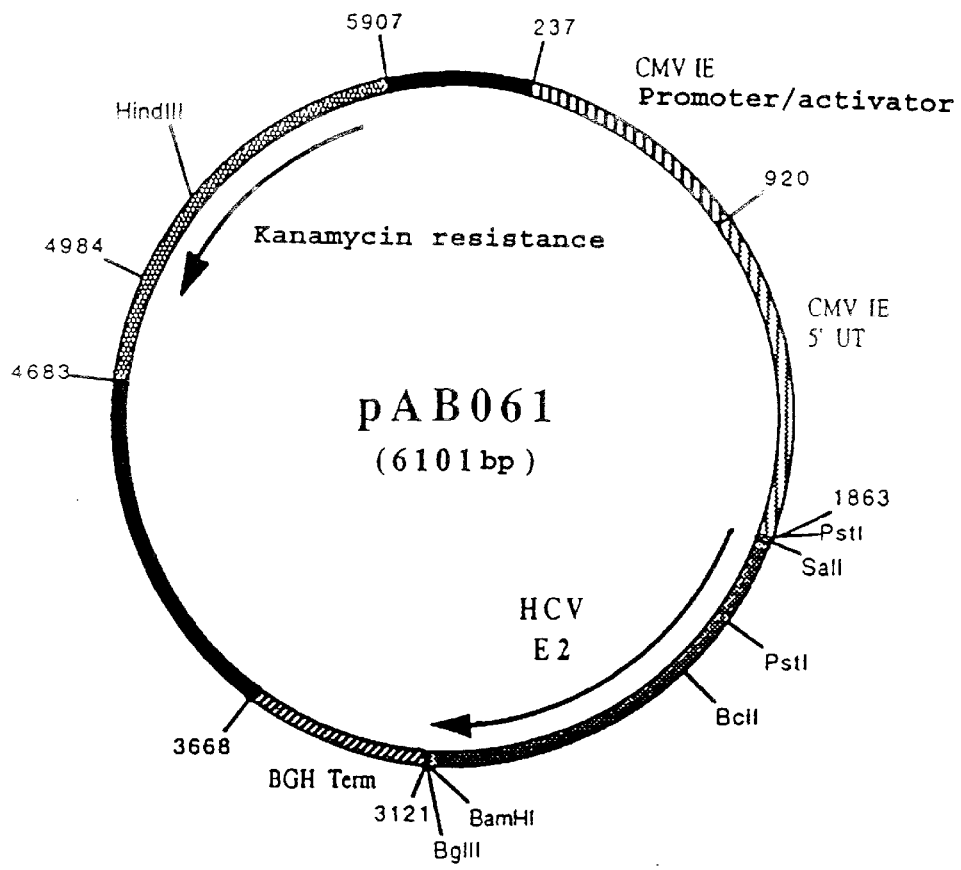
Figure 21:
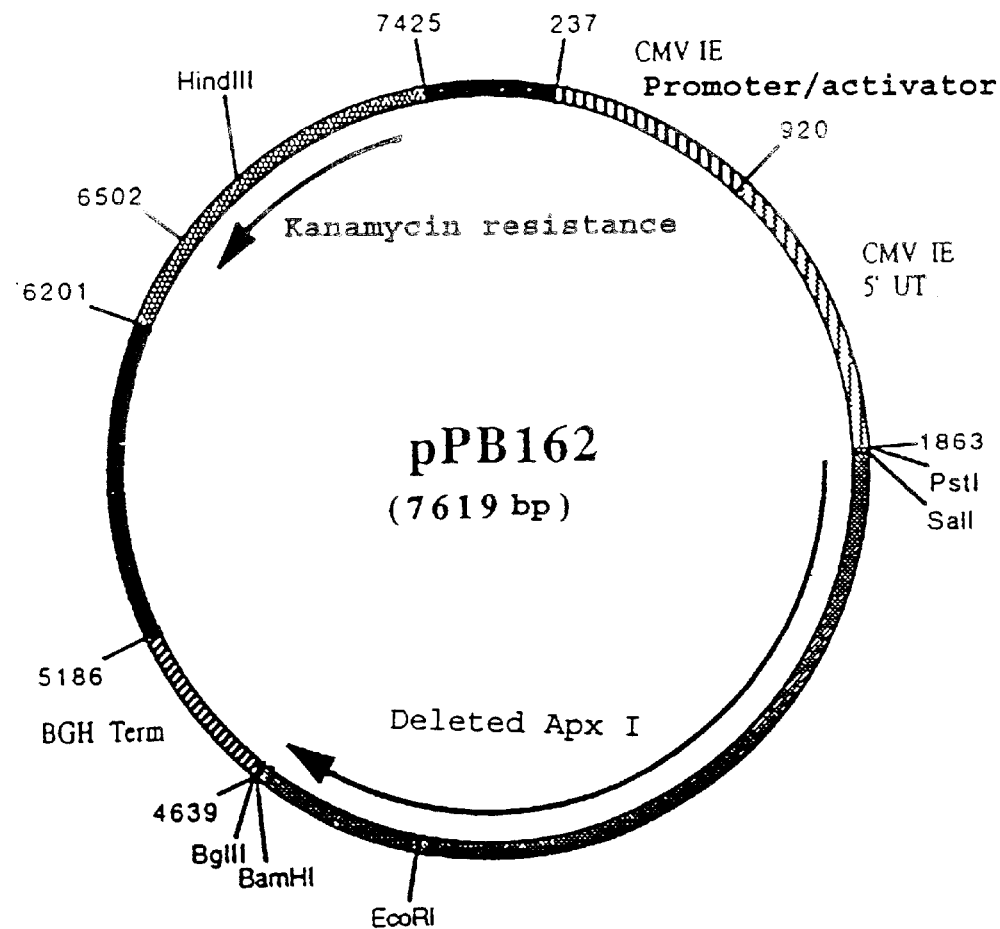
FIG. 21: Plasmid pPB162

An RT-PCR reaction according to the technique described in Example 6 was carried out with the PRRSV virus (Lelystad strain) genomic RNA (J. Meulenberg et al., Virology, 1993, 19, 62–72), prepared according to the technique described in Example 4, and with the following oligonucleotides:
AB170 (32 mer) (SEQ ID No. 23)
5' AAACTGCAGCAATGGCTCATCAGTGTGCACGC 3'
AB171 (30 mer) (SEQ ID No. 24)
5' CGCGGATCCTTATCGTGATGTACTGGGGAG 3'
so as to precisely isolate the "ORF3" gene encoding the envelope glycoprotein "gp45" from the PRRS virus, Lelystad strain. After purification, the 818 bp RT-PCR product was digested with PstI and BamHI in order to isolate an 802 bp PstI-BamHI fragment. This fragment was ligated with the vector pVR1012 (Example 7), previously digested with PstI and BamHI, to give the plasmid pAB091 (5660 bp) (FIG. 16).

Example 17
Construction of the Plasmid pAB092 (PPRSV ORF3 Gene, USA Strain)

An RT-PCR reaction according to the technique described in Example 6 was carried out with the PRRSV virus (ATCC-VR2332 strain) genomic RNA (M. Murtaugh et al., Arch Virol., 1995, 140, 1451–1460), prepared according to the technique described in Example 4, and with the following oligonucleotides:
AN172 (32 mer) (SEQ ID No. 25)
5' AAACTGCAGCAATGGTTAATAGCTGTACATTC 3'
AB173 (32 mer) (SEQ ID No. 26)
5' CGCGGATCCCTATCGCCGTACGGCACTGAGGG 3'
so as to precisely isolate the "ORF3" gene encoding the envelope glycoprotein "gp45" from the PRRS virus, ATCC-VR2332 strain. After purification, the 785 bp RT-PCR product was digested with EstI and BamHI in order to isolate a 769 bp Pst-BamHI fragment. This fragment was ligated with the vector pVR1012 (Example 7), previously digested with PstI and BamHI, to give the plasmid pAB092 (5627 bp) (FIG. 17).

Example 18

Construction of the Plasmid pAB004 (Porcine Parvovirus VP2 Gene)

An RT-PCR reaction according to the technique described in Example 6 was carried out with the porcine parvovirus (NADL2 strain) genomic RNA (J. Vasudevacharya et al., Virology, 1990, 178, 611–616), prepared according to the technique described in Example 4, and with the following oligonucleotides:

AB007 (33 mer) SEQ ID No. 27)

5' AAAACTGCAGAATGAGTGAAAATGTGGAACAAC 3'

AB010 (33 mer) (SEQ ID No. 28)

5' CGCGGATCCCTAGTATAATTTTCTTGGTATAAG 3' so as to amplify a 1757 bp fragment containing the gene encoding the porcine parvovirus VP2 protein. After purification, the RT-PCR product was digested with PstI and BamHI to give a 1740 bp PstI-BamHI fragment. This fragment was ligated with the vector pVR1012 (Example 7), previously digested with PstI and BamHI, to give the plasmid pAB004 (6601 bp) (FIG. 18).

Example 19

Construction of the Plasmid pAB069 (Hog Chlolera HCV E1 Gene)

An RT-PCR reaction according to the technique described in Example 6 was carried out with the hog cholera virus (HCV) (Alfort strain) genomic RNA (G. Meyers et al., Virology, 1989, 171, 18–27), prepared according to the technique described in Example 4, and with the following oligonucleotides:

AB126 (36 mer) (SEQ ID No. 29)

5' ACGCGTCGACATGAAACTAGAAAAAGC-CCTGTTGGC 3'

AB127 (34 mer) (SEQ ID No. 30)

5' CGCGGATCCTCATAGCCGCCCTTGTGCCCCGGTC 3' so as to isolate the sequence encoding the E1 protein from the HCV virus in the form of a 1363 bp RT-PCR fragement. After purification, this fragment was digested with SalI and BamHI to give a 1349 bp SalI-BamHI fragment.

This fragment was ligated with the vector pVR1012 (Example 7), previously digested with SalI and BamHI, to give the plasmid pAB069 (6218 bp) (FIG. No. 19).

Example 20

Construction of the Plasmid pAB061 (Hog Cholera HCV E2 Gene)

An RT-PCR reaction according to the technique described in Example 6 was carried out with the hog cholera virus (HCV) (Alfort strain) genomic RNA (G. Meyers et al., Virology, 1989, 171, 18–27), prepared according to the technique described in Example 4, and with the following oligonucleotides:

AB118 (36 mer) (SEQ ID No. 31)

5' ACGCGTCGACATGTCAACTACT-GCGTTTCTCATTTG 3'

AB119 (33 mer) (SEQ ID No. 32)

5' CGCGGATCCTCACTGTAGACCAGCAGCGAGCTG 3' so as to isolate the sequence encoding the E2 protein from the HCV virus in the form of a 1246 bp RT-PCR fragment. After purification, this fragment was digested with SalI and BamHI to give a 1232 bp SalI-BamHI fragment. This fragment was ligated with the vector pVR1012 (Example 7), previously digested with SalI and BamHI, to give the plasmid pAB061 (6101 bp) (FIG. 20).

Example 21

Construction of the Plasmid pBP162 (Deleted *Actinobacillus pleuropneumoniae* apxI Gene)

The *Actinobacillus pleuropneumoniae* apxI gene was cloned so as to delete the glycine-rich amino acid region (involved in the binding of the calcium ion) which is between amino acids 719 and 846.

A PCR reaction was carried out with the *Actinobacillus pleuropneumoniae* (serotype 1) genomic DNA (J. Frey et al., Infect. Immun., 1991, 59, 3026–3032), prepared according to the technique described in Examples 2 and 3, and with the following oligonucleotides:

PB174 (32 mer) (SEQ ID No. 33)

5' TTGTCGACGTAAATAGCTAAGGAGACAACATG 3'

PB189 (29 mer) (SEQ ID No. 34)

5' TTGAATTCTTCTTCAACAGAATGTAATTC 3' so as to amplify the 5' part of the apxI gene encoding the *Actinobacillus pleuropneumoniae* haemolysin I protein, in the form of a SalI-EcoRI fragment. After purification, the 2193 bp PCR product was digested with SalI and EcoRI in order to isolate a 2183 bp SalI-EcoRI fragment (fragment A).

A PCR reaction was carried out with the *Actinobacillus pleuropneumoniae* (serotype 1) genonic DNA (J. Frey et al., Infect. Immun., 1991, 59, 3026–3032) and with the following oligonucleotides:

BP190 (32 mer) (SEQ ID No. 35)

5' TTGAATTCTATCGCTACAGTAAGGAGTACGG 3'

PB175 (31 mer) (SEQ ID No. 36)

5' TTGGATCCGCTATTTATCATCTAAAAATAAC 3' so as to amplify the 3' part of the apxi gene encoding the *Actinobacillus pleuropneumoniae* haemolysin I protein, in the form of an EcoRI-BamHI fragment. After purification, the 576 bp PCR product was digested with EcoRI and BamHI in order to isolate a 566 bp EcoRI-BamHI fragment (fragment B). The fragments A and B were ligated together with the vector pVR1012 (Example 7), previously digested with SalI and BamHI, to give the plasmid pPB162 (7619 bp) (FIG. 21).

Example 22

Construction of the Plasmid pPB163 (Deleted *Actinobacillus pleuropneumaniae* apxII Gene)

The *Actinobacillus pleuropneumoniae* apxII gene was cloned so as to delete the glycine-rich amino acid region (involved in the binding of the calcium ion) which is between amino acids 716 and 813.

A PCR reaction was carried out with the *Actinobacillus pleuropneumoniae* (serotype 9) genomic DNA (M. Smits et al., Infection and Immunity, 1991, 59, 4497–4504), prepared according to the technique described in Examples 2 and 3, and with the following oligonucleotides:

PB176 (31 mer) (SEQ ID No. 37)

5' TTGTCGACGATCAATTATATAAAGGAGACTC 3'

PB191 (30 mer) (SEQ ID No. 38)
5' TTGAATTCCTCTTCAACTGATTTGAGTGAG 3'
so as to amplify the 5' part of the apxII gene encoding the *Actinobacillus pleuropneumoniae* haemolysin II protein, in the form of an SalI-EcoRI fragment. After purification, the 2190 bp PCR product was digested with SalI and EcoRI in order to isolate a 2180 bp SalI-EcoRI fragment (fragment A).

A PCR reaction was carried out with the *Actinobacillus pleuropneumoniae* (serotype 9) genomic DNA (M. Smits et al., Infection and Immunity, 1991, 59, 4497–4504) and with the following oligonucleotides:
PB192 (29 mer) (SEQ ID No. 39)
5' TTGAATTCGTAAATCTTAAAGACCTCACC 3'
PB177 (30 mer) (SEQ ID No. 40)
5' TTGGATCCACCATAGGATTGCTATGATTTG 3'
so as to amplify the 3' part of the apxII gene encoding the *Actinobacillus pleuropneumoniae* haemolysin II protein, in the form of an EcoRI-BamHI fragment. After purification, the 473 bp PCR product was digested with EcoRI and BamHI in order to isolate a 463 bp EcoRI-BamHI fragment (fragment B).

Figure 22:
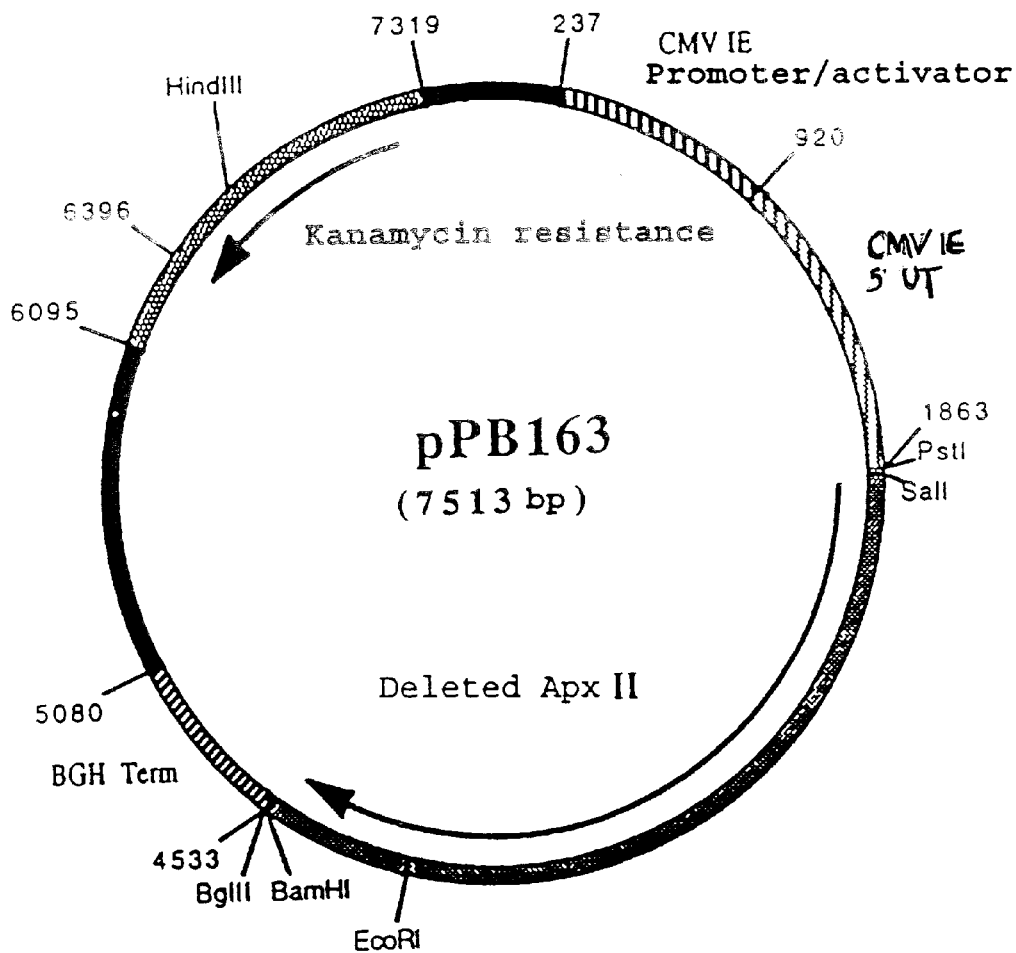
FIG. 22: Plasmid pPB163
Figure 23:
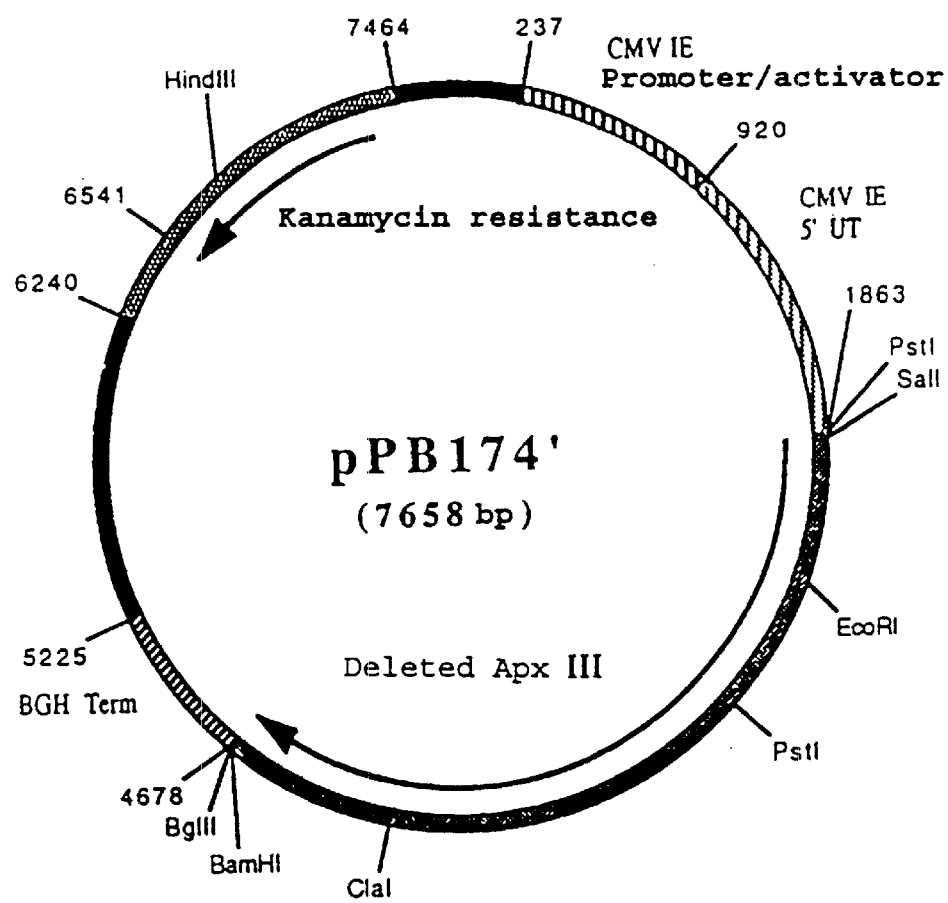
FIG. 23: Plasmid pPB174
Figure 24:
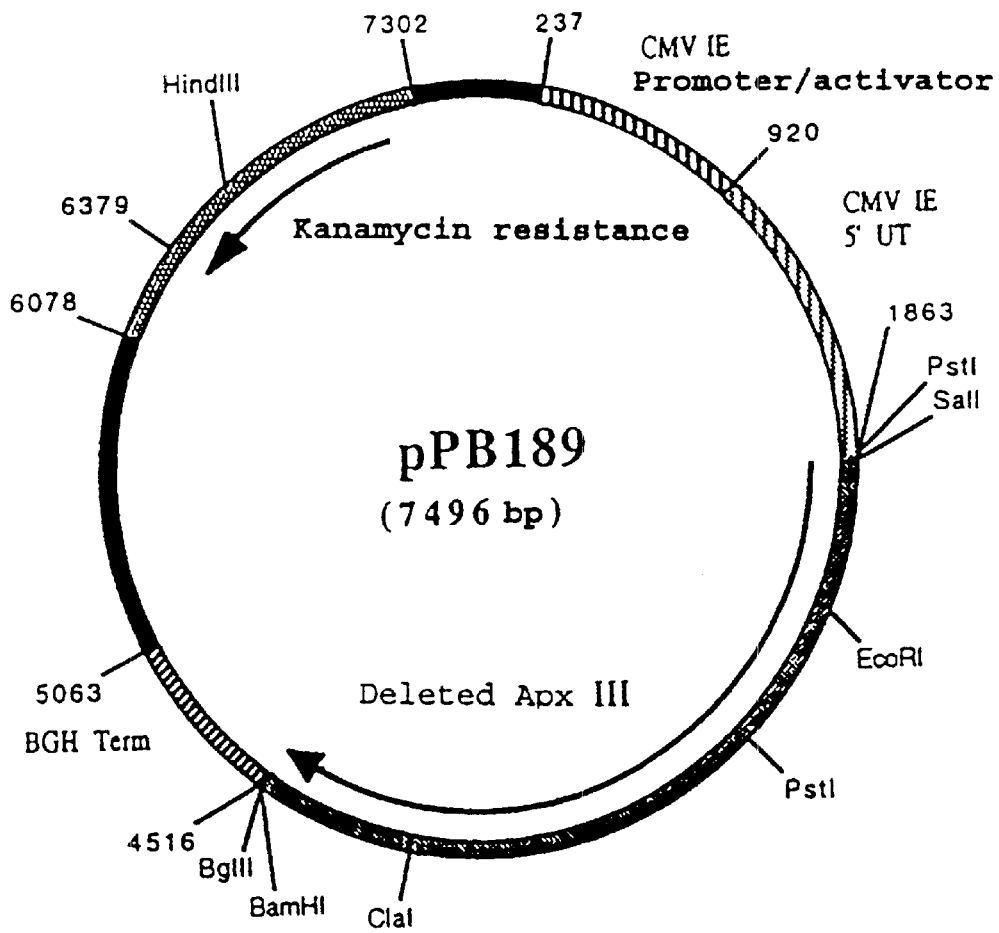
'
FIG. 24: Plasmid pPB189

The fragments A and B were ligated together with the vector pVR1012 (Example 7), previously digested with SalI and BamHI, to give the plasmid pPB163 (7513 bp) (FIG. 22).

Example 23
Construction of the Plasmids pPB174', pPB189 and pPB190 (Deleted *Actinobacillus pleuropneumoniae* apxIII Gene)
First Example of Deletion in AxIII (Plasmid pPB174')

The *Actinobacillus pleuropneumoniae* apxIII gene was cloned so as to delete the glycine-rich amino acid region (involved in the binding of the calcium ion) which is between amino acids 733 and 860.

Figure 25:
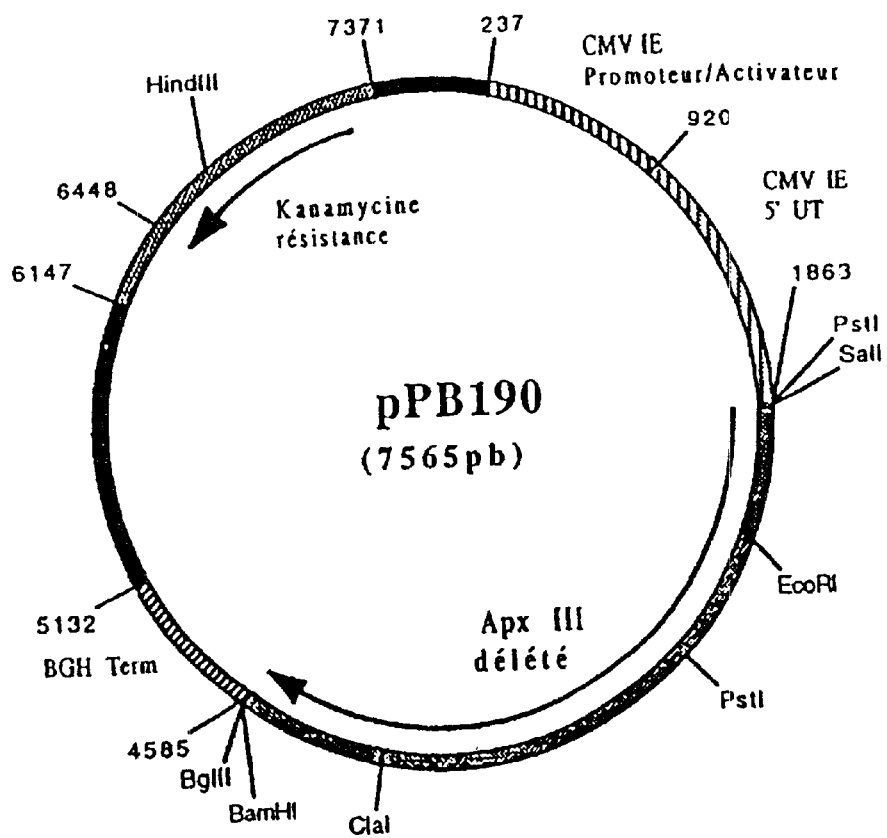
FIG. 25: Plasmid pPB190
Sequence listing SEQ ID No.
SEQ ID No.: 1: Sequence of the PRV gB gene (NIA3 strain)
SEQ ID No.: 2: Oligonucleotide AB166
SEQ ID No.: 3: Oligonucleotide AB167
SEQ ID No.: 4: Oligonucleotide AB168
SEQ ID No.: 5: Oligonucleotide AB169
SEQ ID No.: 6: Sequence of the PRV gD gene (NIA3 strain)
SEQ ID No.: 7: Oligonucleotide PB101
SEQ ID No.: 8: Oligonucleotide PB102
SEQ ID No.: 9: Oligonucleotide PB107
SEQ ID No.: 10: Oligonucleotide PB108
SEQ ID No.: 11: Sequence of the porcine flu HA gene (H1N1 train)
SEQ ID No.: 12: Oligonucleotide PB097
SEQ ID No.: 13: Oligonucleotide PB098
SEQ ID No.: 14: Sequence of the porcine flu NP gene (H1N1 strain)
SEQ ID No.: 15: Oligonucleotide PB095
SEQ ID No.: 16: Oligonucleotide PB096
SEQ ID No.: 17: Sequence of the porcine flu HA gene (H3N2 strain)
SEQ ID No.: 18: Sequence of the porcine flu NP gene (H3N2 strain)
SEQ ID No.: 19: Oligonucleotide AB055
SEQ ID No.: 20: Oligonucleotide AB056
SEQ ID No.: 21: Oligonucleotide AB001
SEQ ID No.: 22: Oligonucleotide AB002
SEQ ID No.: 23: Oligonucleotide AB170
SEQ ID No.: 24: Oligonucleotide AB171
SEQ ID No.: 25: Oligonucleotide AB172
SEQ ID No.: 26: Oligonucleotide AB173
SEQ ID No.: 27: Oligonucleotide AB007
SEQ ID No.: 28: Oligonucleotide AB010
SEQ ID No.: 29: Oligonucleotide AB126
SEQ ID No.: 30: Oligonucleotide AB127
SEQ ID No.: 31: Oligonucleotide AB118
SEQ ID No.: 32: Oligonucleotide AB119
SEQ ID No.: 33: Oligonucleotide PB174
SEQ ID No.: 34: Oligonucleotide PB189
SEQ ID No.: 35: Oligonucleotide PB190
SEQ ID No.: 36: Oligonucleotide PB175
SEQ ID No.: 37: Oligonucleotide PB176
SEQ ID No.: 38: Oligonucleotide PB191
SEQ ID No.: 39: Oligonucleotide PB192
SEQ ID No.: 40: Oligonucleotide PB177
SEQ ID No.: 41: Oligonucleotide PB278
SEQ ID No.: 42: Oligonucleotide PB279
SEQ ID No.: 43: Oligonucleotide PB280
SEQ ID No.: 44: Oligonucleotide PB307
SEQ ID No.: 45: Oligonucleotide PB303
SEQ ID No.: 46: Oligonucleotide PB306
SEQ ID No.: 47: Oligonucleotide PB304
SEQ ID No.: 48: Oligonucleotide PB305";
SEQ ID No.: 49 Sequence of the PRV gB gene (NIA3 strain)
SEQ ID No.: 50 Sequence of the PRV gD gene (NIA3 strain)
SEQ ID No.: 51 Sequence of the porcine flu HA gene (H1N1 train)
SEQ ID No.: 52 Sequence of the porcine flu NP gene (H1N1 strain)
SEQ ID No.: 53 Sequence of the porcine flu HA gene (H3N2 strain)
SEQ ID No.: 54 Sequence of the porcine flu NP gene (H3N2 strain)

A PCR reaction was carried out with the *Actinobacillus pleuropneumonia* (serotype 8) genomic DNA (M. Smits, 1992, Genbank sequence accession No.=X68815), prepared according to the technique described in Examples 2 and 3, and with the following oligonucleotides:
PB278 (30 mer) (SEQ ID No. 41)
5' TTTGTCGACATGAGTACTTGGTCAAGCATG 3'
PB279 (28 mer) (SEQ ID No. 42)
5' TTTATCGATTCTTCTACTGAATGTAATTC 3'
so as to amplify the 5' part of the apxIII gene (encoding the *Actinobacillus pleuropneumonia* haemolysin III protein) in the form of an SalI and ClaI fragment. After purification, the 2216 bp PCR product was digested with SalI and ClaI in order to isolate a 2205 bp SalI-ClaI fragment (fragment A).

A PCR reaction was carried out with the *Actinobacillus pleuropneumonia* (serotype 8) genomic DNA (M. Smits, 1992, Genbank sequence accession No. =X68815) and with the following oligonucleotides:
PB280 (33 mer) (SEQ ID No. 43)
5' TTTATCGATTTATGTTTATCGTTCCACTTCAGG 3'
PB307 (32 mer) (SEQ ID No. 44)
5' TTGGATCCTTAAGCTGCTCTAGCTAGGTTACC 3'
so as to amplify the 3' part of the apxIII gene (encoding the *Actinobacillus pleuropneumonia* haemolysin III protein) in the form of a ClaI-BamHI fragment. After purification, the 596 bp PCR product was digested with ClaI and BamHI in order to isolate a 583 bp ClaI-BamHI fragment (fragment B).

The fragments A and B were ligated together with the vector pVR1012 (Example 7), previously digested with SalI and BamHI, to give the plasmid pPB174' (7658 bp) (FIG. 23).

Second Example of Deletion in ApxIII (Plasmid pPB189)

The *Actinobacillus pleuropneumonia* apxIII gene was cloned so as to delete the glycine-rich amino acid region (involved in the binding of the calcium ion) which is between amino acids 705 and 886.

A PCR reaction was carried out with the *Actinobacillus pleuropneumonia* (serotype 8) genomic DNA (M. Smits, 1992, Genbank sequence accession No.=X68815), prepared according to the technique described in Examples 2 and 3, and with the following oligonucleotides:
PB278 (30 mer) (SEQ ID No. 41)
5' TTTGTCGACATGAGTACTTGGTCAAGCATG 3'
PB303 (32 mer) (SEQ ID No. 45)
5' TTTATCGATTTCTTCACGTTTACCAACAGCAG 3'
so as to amplify the 5' part of the apxIII gene (encoding the *Actinobacillus pleuropneumonia* haemolysin III protein) in the form of a SalI-ClaI fragment. After purification, the 2133 bp PCR product was digested with SalI and ClaI in order to isolate a 2122 bp SalI-ClaI fragment (fragment A).

A PCR reaction was carried out with the *Actinobacillus pleuropneumonia* (serotype 8) genomic DNA (M. Smits, 1992, Genbank sequence accession No.=X68815) and with the following oligonucleotides:
PB306 (31 mer) (SEQ ID No. 46)
5' TTTATCGATTCTGATTTTTCCTTCGATCGTC 3'
PB307 (32 mer) (SEQ ID No. 44)
5' TTGGATCCTTAAGCTGCTCTAGCTAGGTTACC 3'
so as to amplify the 3' part of the apxIII gene (encoding the *Actinobacillus pleuropneumonia* haemolysin III protein) in the form of a ClaI-BamHI fragment. After purification, the 518 bp PCR product was digested with ClaI and BamHI in order to isolat a 506 bp ClaI-BamHI fragment (fragment B).

The fragments A and B were ligated together with the vector pVR1012 (Example 7), previously digested with SalI and BamHI, to give the plasmid pPB189 (7496 bp) (FIG. 24).

Third Example of Deletion in ApxIII (Plasmid pPB190)

The *Actinobacillus pleuropneumonia* apxIII gene was cloned so as to delete the glycine-rich amino acid region (involved in the binding of the calcium ion) which is between amino acids 718 and 876.

A PCR reaction was carried out with the *Actinobacillus pleuropneumonia* (serotype 8) genomic DNA (M. Smits, 1992, Genbank sequence accession No.=X68815), prepared according to the technique described in Examples 2 and 3, and with the following oligonucleotides:
PB278 (30 mer) (SEQ ID No. 41)
5' TTTGTCGACATGAGTACTTGGTCAAGCATG 3'
PB304 (33 mer) (SEQ ID No. 47)
5' TTTATCGATACCTGATTGCGTTAATTCATAATC 3'
so as to amplify the 5' part of the apxIII gene (encoding the *Actinobacillus pleuropneumonia* haemolysin III protein) in the form of a SalI-ClaI fragment. After purification, the 2172 bp PCR product was digested with SalI and ClaI in order to isolate a 2161 bp SalI-ClaI fragment (fragment A).

A PCR reaction was carried out with the *Actinobacillus pleuropneumonia* (serotype 8) genomic DNA (M. Smits, 1992, Genbank sequence accession No. X68815) and with the following oligonucleotides:
PB305 (31 mer) (SEQ ID No. 48)
5' TTTATCGATAAATCTAGTGATTTAGATAAAC 3'
PB307 (32 mer) (SEQ ID No. 44)
5' TTGGATCCTTAAGCTGCTCTAGCTAGGTTACC 3'
so as to amplify the 3' part of the apxIII gene (encoding the *Actinobacillus pleuropneumonia* haemolysin III protein) in the form of a ClaI-BamHI fragment. After purification, the 548 bp PCR product was digested with ClaI and BamHI in order to isolate a 536 bp ClaI-BamHI fragment (fragment B).

The fragments A and B were ligated together with the vector pVR1012 (Example 7), previously digested with SalI and BamHI, to give the plasmid pPB190 (7565 bp) (FIG. 25).

Example 24
Preparation and Purification of the Plasmids

For the preparation of the plasmids intended for the vaccination of animals, any technique may be used which makes it possible to obtain a suspension of purified plasmids predominantly in the supercoiled form. These techniques are well known to persons skilled in the art. There may be mentioned in particular the alkaline lysis technique followed by two successive ultracentrifugations on a caesium chloride gradient in the presence of ethidium bromide as described in J. Sambrook et al. (*Molecular Cloning: A Laboratory Manual,* 2nd edition, Cold Spring Harbor Laboratory, Cold Spring Harbor, N.Y., 1989). Reference may also be made to patent applications PCT WO 85/21250 and PCT WO 96/02658 which describe methods for producing, on an industrial scale, plasmids which can be used for vaccination. For the purposes of the manufacture of vaccines (see Example 17), the purified plasmids are resuspended so as to obtain solutions at a high concentration (>2 mg/ml) which are compatible with storage. To do this the plasmids are resuspended either in ultrapure water or in TE buffer (10 mM Tris-HCl; 1 mM EDTA, pH 8.0).

Example 25
Manufacture of the Associated Vaccines

The various plasmids necessary for the manufacture of an associated vaccine are mixed starting with their concentrated solutions (Example 16). The mixtures are prepared such that the final concentration of each plasmid corresponds to the effective dose of each plasmid. The solutions which can be used to adjust the final concentration of the vaccine may be either a 0.9% NaCl solution, or PBS buffer.

Specific formulations such as liposomes, cationic lipids, may also be used for the manufacture of the vaccines.

Example 26
Vaccination of Pigs

The pigs are vaccinated with doses of 100 µg, 250 µg or 500 µg per plasmid.

The injections can be performed with a needle by the intramuscular route. In this case, the vaccinal doses are administered in a volume of 2 ml.

The injections can be performed by the intradermal route using a liquid jet injection apparatus (with no needle) delivering a dose of 0.2 ml at 5 points (0.04 ml per point of injection) (for example "PIGJET" apparatus). In this case, the vaccinal doses are administered in 0.2 or 0.4 ml volumes, which corresponds to one or two administrations respectively. When two successive administrations are performed by means of the PIGJET apparatus, these administrations are spaced out so that the two injection zones are separated from each other by a distance of about 1 to 2 centimeters.

What is claimed is:

1. A porcine vaccine comprising plasmid(s) that contain(s) and express(es) in vivo in a porcine host cell nucleic acid sequence(s) from the Aujeszky's disease virus encoding protein(s) selected from the group consisting of gB, gD and gB and gD, and a pharmaceutically acceptable carrier.

2. The vaccine according to claim 1, wherein the plasmid contains nucleic acid sequences encoding both the gB and gD proteins.

3. The vaccine according to claim 1, wherein the plasmid contains a nucleic acid sequence encoding the gB protein.

4. The vaccine according to claim 1, wherein the plasmid contains a nucleic acid sequence encoding the gD protein.

5. The vaccine according to claim 1, which comprises a first plasmid that contains a nucleic acid sequence encoding the gB protein and a second plasmid that a nucleic acid sequence encoding the gD protein.

6. A porcine vaccine comprising plasmid(s) that contain(s) and express(es) in vivo in a porcine host cell nucleic acid sequence(s) from PRRS virus encoding protein(s) selected from the group consisting of E, ORF3 and M and combinations thereof, and a pharmaceutically acceptable carrier.

7. The vaccine according to claim 6, wherein the plasmid contains a nucleic acid sequence encoding the E protein.

8. The vaccine according to claim 6, wherein the plasmid contains a nucleic acid sequence encoding the ORF3 protein.

9. The vaccine according to claim 6, wherein the plasmid contains a nucleic acid sequence encoding the M protein.

10. The vaccine according to claim 6, which comprises a first plasmid that contains a nucleic acid sequence encoding a PRRS protein and a second plasmid that contains a nucleic acid sequence encoding another PRRS protein, wherein the PRRS proteins of the first and second plasmids are selected from the group consisting of E, ORF3, and M and combinations thereof.

11. A porcine vaccine comprising plasmid(s) that contain(s) and express(es) in vivo in a porcine host cell nucleic acid sequence(s) from hog cholera virus encoding protein(s) selected from the group consisting of E1, E2, and E1 and E2, and a pharmaceutically acceptable carrier.

12. The vaccine according to claim 11, wherein the plasmid contains a nucleic acid sequence encoding the E1 protein.

13. The vaccine according to claim 11, wherein the plasmid contains a nucleic acid sequence encoding the E2 protein.

14. The vaccine according to claim 11, wherein the plasmid contains nucleic acid sequences encoding both the E1 and E2 proteins.

15. The vaccine according to claim 11, which comprises a first plasmid that contains a nucliec acid sequence encoding the E1 protein and a second plasmid that contains a nucliec acid sequence encoding the E2 protein.

16. The vaccine according to claim 1, wherein expression of the nucleic acid sequence(s) is/are under the control of a promoter selected from the group consisting of a CMV-IE promoter, a SV40 early promoter, a SV40 late promoter, a Rous sarcoma virus LTR promoter, and a promoter of a cytoskeleton gene.

17. The vaccine according to claim 6, wherein expression of the nucleic acid sequence(s) is/are under the control of a promoter selected from the group consisting of a CMV-IE promoter, a SV40 early promoter, a SV40 late promoter, a Rous sarcoma virus LTR promoter, and a promoter of a cytoskeleton gene.

18. The vaccine according to claim 11, wherein expression of the nucleic acid sequence(s) is/are under the control of a promoter selected from the group consisting of a CMV-IE promoter, a SV40 early promoter, a SV40 late promoter, a Rous sarcoma virus LTR promoter, and a promoter of a cytoskeleton gene.

19. The vaccine according to claim 16, wherein the promoter is the CMV-IE promoter.

20. The vaccine according to claim 17, wherein the promoter is the CMV-IE promoter.

21. The vaccine according to claim 18, wherein the promoter is the CMV-IE promoter.

22. A method of vaccinating a porcine host comprising: administering to said porcine a vaccine selected from the group consisting of a live whole vaccine, an inactivated whole vaccine, a subunit vaccine, and a recombinant vaccine; and thereafter, administering to said porcine a vaccine as claimed in claim 1.

23. A method of vaccinating a porcine host comprising: administering to said porcine a vaccine selected from the group consisting of a live whole vaccine, an inactivated whole vaccine, a subunit vaccine, and a recombinant vaccine; and thereafter, administering to said porcine a vaccine as claimed in claim 6.

24. A method of vaccinating a porcine host comprising: administering to said porcine a vaccine selected from the group consisting of a live whole vaccine, an inactivated whole vaccine, a subunit vaccine, and a recombinant vaccine; and thereafter, administering to said porcine a vaccine as claimed in claim 11.

25. A method for vaccinating a porcine comprising administering to said porcine a vaccine as claimed in claim 1.

26. A method for vaccinating a porcine comprising administering to said porcine a vaccine as claimed in claim 6.

27. A method for vaccinating a porcine comprising administering to said porcine a vaccine as claimed in claim 11.

28. A kit comprising (i) a vaccine according to claim 1, and (ii) a porcine vaccine selected from the group consisting of a live whole vaccine, an inactivated whole vaccine, a subunit vaccine, and recombinant vaccine.

29. A kit comprising (i) a vaccine according to claim 6, and (ii) a porcine vaccine selected from the group consisting of a live whole vaccine, an inactivated whole vaccine, a subunit vaccine, and recombinant vaccine.

30. A kit comprising (i) a vaccine according to claim 11, and (ii) a porcine vaccine selected from the group consisting of a live whole vaccine, an inactivated whole vaccine, a subunit vaccine, and recombinant vaccine.

* * * * *

UNITED STATES PATENT AND TRADEMARK OFFICE
CERTIFICATE OF CORRECTION

PATENT NO.     : 6,576,243 B1                                                   Page 1 of 1
DATED          : June 10, 2003
INVENTOR(S)    : Jean-Christophe Audonnet et al.

It is certified that error appears in the above-identified patent and that said Letters Patent is hereby corrected as shown below:

<u>Title page,</u>
Item [75], Inventors, change "Lyons" to -- Lyon --

Item [73], Assignee, change "Lyons" to -- Lyon --

Signed and Sealed this

Twenty-third Day of December, 2003

JAMES E. ROGAN
*Director of the United States Patent and Trademark Office*

UNITED STATES PATENT AND TRADEMARK OFFICE
CERTIFICATE OF CORRECTION

| | |
|---|---|
| PATENT NO. | : 6,576,243 B1 |
| APPLICATION NO. | : 09/784984 |
| DATED | : June 10, 2003 |
| INVENTOR(S) | : Jean-Christophe Audonnet et al. |

It is certified that error appears in the above-identified patent and that said Letters Patent is hereby corrected as shown below:

On the Cover Page, item (57), lines 2, 3, 4 and 6:

In the abstract, for the recitation of "bovine", each occurrence, should read --porcine--.

Signed and Sealed this

Fourth Day of August, 2009

JOHN DOLL
*Acting Director of the United States Patent and Trademark Office*

UNITED STATES PATENT AND TRADEMARK OFFICE
CERTIFICATE OF CORRECTION

PATENT NO.       : 6,576,243 B1
APPLICATION NO.  : 09/784984
DATED            : June 10, 2003
INVENTOR(S)      : Jean-Christophe Audonnet et al.

It is certified that error appears in the above-identified patent and that said Letters Patent is hereby corrected as shown below:

On the Cover Page, item (57), lines 2, 3, 4 and 6:

In the abstract, for the recitation of "arvian", each occurrence, should read --porcine--.

This certificate supersedes the Certificate of Correction issued August 4, 2009.

Signed and Sealed this

Seventeenth Day of November, 2009

David J. Kappos
*Director of the United States Patent and Trademark Office*

SEQUENCE LISTING

<160> NUMBER OF SEQ ID NOS: 54

<210> SEQ ID NO 1
<211> LENGTH: 2742
<212> TYPE: DNA
<213> ORGANISM: Pseudorabies virus
<220> FEATURE:
<221> NAME/KEY: CDS
<222> LOCATION: (1)..(2742)
<223> OTHER INFORMATION:

<400> SEQUENCE: 1

```
atg ccc gct ggt ggc ggt ctt tgg cgc ggg ccc cgg ggg cat cgg ccc        48
Met Pro Ala Gly Gly Gly Leu Trp Arg Gly Pro Arg Gly His Arg Pro
1               5                   10                  15 ggg cac cac ggc ggt gct ggc ctc gga cgt ctt tgg cct gct cca cac        96
Gly His His Gly Gly Ala Gly Leu Gly Arg Leu Trp Pro Ala Pro His
                20                  25                  30 cac gct gca gct gcg cgg ggc gcc gtc gcg cta gcg ctg ctg ctg ctg       144
His Ala Ala Ala Ala Arg Gly Ala Val Ala Leu Ala Leu Leu Leu Leu
            35                  40                  45 gcg ctc gcc gcg gcc ccg ccg tgc ggc gcg gcg gcc gtg acg cgg gcc       192
Ala Leu Ala Ala Ala Pro Pro Cys Gly Ala Ala Ala Val Thr Arg Ala
        50                  55                  60 gcc tcg gcc tcg ccg acg ccc ggg acg ggc gcc acc ccc aac gac gtc       240
Ala Ser Ala Ser Pro Thr Pro Gly Thr Gly Ala Thr Pro Asn Asp Val
65                  70                  75                  80 tcc gcc gag gcg tcc ctc gag gag atc gag gcg ttc tcc ccc ggc ccc       288
Ser Ala Glu Ala Ser Leu Glu Glu Ile Glu Ala Phe Ser Pro Gly Pro
                85                  90                  95 tcg gag gcc ccc gac ggc gag tac ggc gac ctg gac gcg cgg acg gcc       336
Ser Glu Ala Pro Asp Gly Glu Tyr Gly Asp Leu Asp Ala Arg Thr Ala
                100                 105                 110
```

```
gtg cgc gcg gcc gcg acc gag cgg gac cgc ttc tac gtc tgc ccg ccg      384
Val Arg Ala Ala Ala Thr Glu Arg Asp Arg Phe Tyr Val Cys Pro Pro
        115                 120                 125 ccg tcc ggc tcc acg gtg gtg cgg ctg gag ccc gag cag gcc tgc ccc      432
Pro Ser Gly Ser Thr Val Val Arg Leu Glu Pro Glu Gln Ala Cys Pro
130                 135                 140 gag tac tcg cag ggg cgc aac ttc acg gag ggg atc gcc ctg ctc ttc      480
Glu Tyr Ser Gln Gly Arg Asn Phe Thr Glu Gly Ile Ala Leu Leu Phe
145                 150                 155                 160 aag gag aac atc gcc ccg cac aag ttc aag gcc cac atc tac tac aag      528
Lys Glu Asn Ile Ala Pro His Lys Phe Lys Ala His Ile Tyr Tyr Lys
                165                 170                 175 aac gtc atc gtc acg acc gtg tgg tcc ggg agc acg tac gcg gcc atc      576
Asn Val Ile Val Thr Thr Val Trp Ser Gly Ser Thr Tyr Ala Ala Ile
            180                 185                 190 acg aac cgc ttc aca gac cgc gtg ccc gtc ccc gtg cag gag atc acg      624
Thr Asn Arg Phe Thr Asp Arg Val Pro Val Pro Val Gln Glu Ile Thr
        195                 200                 205 gac gtg atc gac cgc cgc ggc aag tgc gtc tcc aag gcc gag tac gtg      672
Asp Val Ile Asp Arg Arg Gly Lys Cys Val Ser Lys Ala Glu Tyr Val
    210                 215                 220 cgc aac aac cac aag gtg acc gcc ttc gac cgc gac gag aac ccc gtc      720
Arg Asn Asn His Lys Val Thr Ala Phe Asp Arg Asp Glu Asn Pro Val
225                 230                 235                 240 gag gtg gac ctg cgc ccc tcg cgc ctg aac gcg ctc ggc acc cgc gcc      768
Glu Val Asp Leu Arg Pro Ser Arg Leu Asn Ala Leu Gly Thr Arg Ala
                245                 250                 255 tgg cac acc acc aac gac acc tac acc aag atc ggc gcc gcg ggc ttc      816
Trp His Thr Thr Asn Asp Thr Tyr Thr Lys Ile Gly Ala Ala Gly Phe
            260                 265                 270 tac cag acg ggc acc tcc gtc aac tgc atc gtc gag gag gtg gag gcg      864
Tyr Gln Thr Gly Thr Ser Val Asn Cys Ile Val Glu Glu Val Glu Ala
        275                 280                 285 cgc tcc gtg tac ccc tac gac tcc ttc gcc ctg tcc acg ggg gac att      912
Arg Ser Val Tyr Pro Tyr Asp Ser Phe Ala Leu Ser Thr Gly Asp Ile
    290                 295                 300 gtg tac atg tcc ccc ttc tac ggc ctg cgc gag ggg gcc cac ggg gag      960
Val Tyr Met Ser Pro Phe Tyr Gly Leu Arg Glu Gly Ala His Gly Glu
305                 310                 315                 320 cag atc ggc tac gcg ccc ggg cgc ttc cag cag gtg gag cac tac tac     1008
Gln Ile Gly Tyr Ala Pro Gly Arg Phe Gln Gln Val Glu His Tyr Tyr
                325                 330                 335 ccc atc gac ctg gac tcg cgc ctc cgc gcc tcc gag agc gtg acg cgc     1056
Pro Ile Asp Leu Asp Ser Arg Leu Arg Ala Ser Glu Ser Val Thr Arg
            340                 345                 350 aac ttt cta cgc acg ccg cac ttc acg gtg gcc tgg gac tgg gcc ccc     1104
Asn Phe Leu Arg Thr Pro His Phe Thr Val Ala Trp Asp Trp Ala Pro
        355                 360                 365 aag acg cgg cgc gtg tgc agc ctg gcc aag tgg cgc gag gcc gag gag     1152
Lys Thr Arg Arg Val Cys Ser Leu Ala Lys Trp Arg Glu Ala Glu Glu
    370                 375                 380 atg acc cgc gac gag acg cgc gac ggc tcc ttc cgc ttc acg tcg cgg     1200
Met Thr Arg Asp Glu Thr Arg Asp Gly Ser Phe Arg Phe Thr Ser Arg
385                 390                 395                 400 gcc ctg ggc gcc tcc ttc gtc agc gac gtc acg cag ctg gac ctg cag     1248
Ala Leu Gly Ala Ser Phe Val Ser Asp Val Thr Gln Leu Asp Leu Gln
                405                 410                 415 cgc gtg cac ctg ggc gac tgc gtc ctc cgc gag gcc tcg gag gcc atc     1296
Arg Val His Leu Gly Asp Cys Val Leu Arg Glu Ala Ser Glu Ala Ile
```

-continued

|  |  |  |  |  |  |  |  |  |  |  |  |  |  |  |  |  |
|---|---|---|---|---|---|---|---|---|---|---|---|---|---|---|---|---|
|  |  |  | 420 |  |  |  |  | 425 |  |  |  |  | 430 |  |  |  |

```
gac gcc atc tac cgg cgg cgc tac aac agc acg cac gtg ctg gcc ggc     1344
Asp Ala Ile Tyr Arg Arg Arg Tyr Asn Ser Thr His Val Leu Ala Gly
            435                 440                 445 gac agg ccc gag gtg tac ctc gcc cgc ggg ggc ttc gtg gtg gcc ttc     1392
Asp Arg Pro Glu Val Tyr Leu Ala Arg Gly Gly Phe Val Val Ala Phe
    450                 455                 460 cgc ccg ctg atc tcg aac gag ctg gcg cag ctg tac gcg cgc gag ctc     1440
Arg Pro Leu Ile Ser Asn Glu Leu Ala Gln Leu Tyr Ala Arg Glu Leu
465                 470                 475                 480 gag cgc ctc ggc ctc gcc ggc gtc gtg ggc ccc gcg gcc ccc gcg gcc     1488
Glu Arg Leu Gly Leu Ala Gly Val Val Gly Pro Ala Ala Pro Ala Ala
                485                 490                 495 gcc cgt cgg gcc cgg cgc tcc ccc ggc ccg gcg ggg acg ccc gag ccg     1536
Ala Arg Arg Ala Arg Arg Ser Pro Gly Pro Ala Gly Thr Pro Glu Pro
            500                 505                 510 ccg gcc gtc aac ggc acg ggg cac ctg cgc atc acc acg ggc tcg gcg     1584
Pro Ala Val Asn Gly Thr Gly His Leu Arg Ile Thr Thr Gly Ser Ala
        515                 520                 525 gag ttt gcg cgc ctg cag ttc acc tac gac cac atc cag gcg cac gtg     1632
Glu Phe Ala Arg Leu Gln Phe Thr Tyr Asp His Ile Gln Ala His Val
    530                 535                 540 aac gac atg ctg ggc cgc atc gcg gcc gcc tgg tgc gag ctg cag aac     1680
Asn Asp Met Leu Gly Arg Ile Ala Ala Ala Trp Cys Glu Leu Gln Asn
545                 550                 555                 560 aag gac cgc acc ctg tgg agc gag atg tcg cgc ctg aac ccc agc gcc     1728
Lys Asp Arg Thr Leu Trp Ser Glu Met Ser Arg Leu Asn Pro Ser Ala
                565                 570                 575 gtg gcc acg gcc gcg ctc ggc cag cgc gtc tgc gcg cgc atg ctc ggc     1776
Val Ala Thr Ala Ala Leu Gly Gln Arg Val Cys Ala Arg Met Leu Gly
            580                 585                 590 gac gtg atg gcc atc tcg cgg tgc gtg gag gtg cgc ggc ggc gtg tac     1824
Asp Val Met Ala Ile Ser Arg Cys Val Glu Val Arg Gly Gly Val Tyr
        595                 600                 605 gtg cag aac tcc atg cgc gtg ccc ggc gag cgc ggc acg tgc tac agc     1872
Val Gln Asn Ser Met Arg Val Pro Gly Glu Arg Gly Thr Cys Tyr Ser
    610                 615                 620 cgc ccg ctg gtc acc ttc gag cac aac ggc acg ggc gtg atc gag ggc     1920
Arg Pro Leu Val Thr Phe Glu His Asn Gly Thr Gly Val Ile Glu Gly
625                 630                 635                 640 cag ctc ggc gac gac aac gag ctc ctc atc tcg cgc gac ctc atc gag     1968
Gln Leu Gly Asp Asp Asn Glu Leu Leu Ile Ser Arg Asp Leu Ile Glu
                645                 650                 655 ccc tgc acc ggc aac cac cgg cgc tac ttt aag ctg ggg agc ggg tac     2016
Pro Cys Thr Gly Asn His Arg Arg Tyr Phe Lys Leu Gly Ser Gly Tyr
            660                 665                 670 gtg tac tac gag gac tac aac tac gtg cgc atg gtg gag gtg ccc gag     2064
Val Tyr Tyr Glu Asp Tyr Asn Tyr Val Arg Met Val Glu Val Pro Glu
        675                 680                 685 acg atc agc acg cgg gtt acc ctg aac ctg acg ctg ctg gag gac cgc     2112
Thr Ile Ser Thr Arg Val Thr Leu Asn Leu Thr Leu Leu Glu Asp Arg
    690                 695                 700 gag ttc ctg ccc ctc gag gtg tac acg cgc gag gag ctc gcc gac acg     2160
Glu Phe Leu Pro Leu Glu Val Tyr Thr Arg Glu Glu Leu Ala Asp Thr
705                 710                 715                 720 ggc ctc ctg gac tac agc gag atc cag cgc cgc aac cag ctg cac gcg     2208
Gly Leu Leu Asp Tyr Ser Glu Ile Gln Arg Arg Asn Gln Leu His Ala
                725                 730                 735 ctc aag ttc tac gac atc gac cgc gtg gtc aag gtg gac cac aac gtg     2256
```

```
                Leu Lys Phe Tyr Asp Ile Asp Arg Val Val Lys Val Asp His Asn Val
                                740                 745                 750 gtg ctg ctg cgc ggc atc gcc aac ttc ttc cag ggc ctc ggc gac gtg            2304
Val Leu Leu Arg Gly Ile Ala Asn Phe Phe Gln Gly Leu Gly Asp Val
            755                 760                 765 ggc gcc gcc gtc ggc aag gtg gtc ctg ggt gcc acg ggg gcc gtg atc            2352
Gly Ala Ala Val Gly Lys Val Val Leu Gly Ala Thr Gly Ala Val Ile
770                 775                 780 tcg gcc gtc ggc ggc atg gtg tcc ttc ctg tcc aac ccc ttc ggg gcg            2400
Ser Ala Val Gly Gly Met Val Ser Phe Leu Ser Asn Pro Phe Gly Ala
785                 790                 795                 800 ctc gcc atc ggg ctg ctg gtg ctg gcc ggc ctg gtc gcg gcc ttc ctg            2448
Leu Ala Ile Gly Leu Leu Val Leu Ala Gly Leu Val Ala Ala Phe Leu
                805                 810                 815 gcc tac cgg cac atc tcg cgc ctg cgc cgc aac ccc atg aag gcc ctg            2496
Ala Tyr Arg His Ile Ser Arg Leu Arg Arg Asn Pro Met Lys Ala Leu
            820                 825                 830 tac ccc gtc acg acg aag acg ctc aag gag gac ggc gtc gac gaa ggc            2544
Tyr Pro Val Thr Thr Lys Thr Leu Lys Glu Asp Gly Val Asp Glu Gly
        835                 840                 845 gac gtg gac gag gcc aag ctg gac cag gcc cgg gac atg atc cgg tac            2592
Asp Val Asp Glu Ala Lys Leu Asp Gln Ala Arg Asp Met Ile Arg Tyr
850                 855                 860 atg tcc atc gtg tcg gcc ctc gag cag cag gag cac aag gcg cgc aag            2640
Met Ser Ile Val Ser Ala Leu Glu Gln Gln Glu His Lys Ala Arg Lys
865                 870                 875                 880 aag aac agc ggg ccc gcg ctg ctg gcc agc cgc gtc ggg gcg atg gcc            2688
Lys Asn Ser Gly Pro Ala Leu Leu Ala Ser Arg Val Gly Ala Met Ala
                885                 890                 895 acg cgc cgc cgg cac tac cag cgc ctc gag agc gag gac ccc gac gcc            2736
Thr Arg Arg Arg His Tyr Gln Arg Leu Glu Ser Glu Asp Pro Asp Ala
            900                 905                 910 ctg tag                                                                    2742
Leu <210> SEQ ID NO 2
<211> LENGTH: 33
<212> TYPE: DNA
<213> ORGANISM: Aujesky's Disease Virus (NIA3 Strain)

```
<212> TYPE: DNA
<213> ORGANISM: Aujesky's Disease Virus (NIA3 Strain)

<400> SEQUENCE: 5
gatccctaca gggcgtcggg gtcctcgctc tcgaggcgct ggtagtgcc                49

<210> SEQ ID NO 6
<211> LENGTH: 1213
<212> TYPE: DNA
<213> ORGANISM: Aujesky's Disease Virus (NIA3 Strain)
<220> FEATURE:
<221> NAME/KEY: CDS
<222> LOCATION: (1)..(1212)
<223> OTHER INFORMATION:

<400> SEQUENCE: 6
```

| atg | ctg | ctc | gca | gcg | cta | ttg | gcg | gcg | ctg | gtc | gcc | cgg | acg | acg | ctc | 48 |
|---|---|---|---|---|---|---|---|---|---|---|---|---|---|---|---|---|
| Met | Leu | Leu | Ala | Ala | Leu | Leu | Ala | Ala | Leu | Val | Ala | Arg | Thr | Thr | Leu | |
| 1 | | | | 5 | | | | | 10 | | | | | 15 | | |

| ggt | gcg | gac | gtg | gac | gcc | gtg | ccc | gcg | ccg | acc | ttc | ccc | ccg | ccc | gcg | 96 |
|---|---|---|---|---|---|---|---|---|---|---|---|---|---|---|---|---|
| Gly | Ala | Asp | Val | Asp | Ala | Val | Pro | Ala | Pro | Thr | Phe | Pro | Pro | Pro | Ala | |
| | | | 20 | | | | | 25 | | | | | 30 | | | |

| tac | ccg | tac | acc | gag | tcg | tgg | cag | ctg | acg | ctg | acg | acg | gtc | ccc | tcg | 144 |
|---|---|---|---|---|---|---|---|---|---|---|---|---|---|---|---|---|
| Tyr | Pro | Tyr | Thr | Glu | Ser | Trp | Gln | Leu | Thr | Leu | Thr | Thr | Val | Pro | Ser | |
| | | 35 | | | | | 40 | | | | | 45 | | | | |

| ccc | ttc | gtc | ggc | ccc | gcg | gac | gtc | tac | cac | acg | cgc | ccg | ctg | gag | gac | 192 |
|---|---|---|---|---|---|---|---|---|---|---|---|---|---|---|---|---|
| Pro | Phe | Val | Gly | Pro | Ala | Asp | Val | Tyr | His | Thr | Arg | Pro | Leu | Glu | Asp | |
| | 50 | | | | | 55 | | | | | 60 | | | | | |

| ccg | tgc | ggg | gtg | gtg | gcg | ctg | atc | tcc | gac | ccg | cag | gtg | gac | cgg | ctg | 240 |
|---|---|---|---|---|---|---|---|---|---|---|---|---|---|---|---|---|
| Pro | Cys | Gly | Val | Val | Ala | Leu | Ile | Ser | Asp | Pro | Gln | Val | Asp | Arg | Leu | |
| 65 | | | | | 70 | | | | | 75 | | | | | 80 | |

| ctg | aac | gag | gcg | gtg | gcc | cac | cgg | cgg | ccc | acg | tac | cgc | gcc | cac | gtg | 288 |
|---|---|---|---|---|---|---|---|---|---|---|---|---|---|---|---|---|
| Leu | Asn | Glu | Ala | Val | Ala | His | Arg | Arg | Pro | Thr | Tyr | Arg | Ala | His | Val | |
| | | | | 85 | | | | | 90 | | | | | 95 | | |

| gcc | tgg | tac | cgc | atc | gcg | gac | ggg | tgc | gca | cac | ctg | ctg | tac | ttt | atc | 336 |
|---|---|---|---|---|---|---|---|---|---|---|---|---|---|---|---|---|
| Ala | Trp | Tyr | Arg | Ile | Ala | Asp | Gly | Cys | Ala | His | Leu | Leu | Tyr | Phe | Ile | |
| | | | 100 | | | | | 105 | | | | | 110 | | | |

| gag | tac | gcc | gac | tgc | gac | ccc | agg | cag | gca | gat | ctt | tgg | gcg | ctg | ccg | 384 |
|---|---|---|---|---|---|---|---|---|---|---|---|---|---|---|---|---|
| Glu | Tyr | Ala | Asp | Cys | Asp | Pro | Arg | Gln | Ala | Asp | Leu | Trp | Ala | Leu | Pro | |
| | | 115 | | | | | 120 | | | | | 125 | | | | |

| gcg | ccg | cac | cac | gcc | gat | gtg | gtg | gac | ccc | gtc | cgc | gga | cta | cat | gtt | 432 |
|---|---|---|---|---|---|---|---|---|---|---|---|---|---|---|---|---|
| Ala | Pro | His | His | Ala | Asp | Val | Val | Asp | Pro | Val | Arg | Gly | Leu | His | Val | |
| | 130 | | | | | 135 | | | | | 140 | | | | | |

| ccc | cac | gga | gga | cga | gct | ggg | gct | gct | cat | ggt | ggc | ccc | cgg | gcg | gtt | 480 |
|---|---|---|---|---|---|---|---|---|---|---|---|---|---|---|---|---|
| Pro | His | Gly | Gly | Arg | Ala | Gly | Ala | Ala | His | Gly | Gly | Pro | Arg | Ala | Val | |
| 145 | | | | | 150 | | | | | 155 | | | | | 160 | |

| caa | cga | ggg | cca | gta | ccg | gcg | cct | ggt | gtc | cgt | cga | cgg | cgt | gaa | cat | 528 |
|---|---|---|---|---|---|---|---|---|---|---|---|---|---|---|---|---|
| Gln | Arg | Gly | Pro | Val | Pro | Ala | Pro | Gly | Val | Arg | Arg | Arg | Arg | Glu | His | |
| | | | | 165 | | | | | 170 | | | | | 175 | | |

| cct | cac | cga | ctt | cat | ggt | ggc | gct | ccc | cga | ggg | gca | aga | gtg | ccc | gtt | 576 |
|---|---|---|---|---|---|---|---|---|---|---|---|---|---|---|---|---|
| Pro | His | Arg | Leu | His | Gly | Gly | Ala | Pro | Arg | Gly | Ala | Arg | Val | Pro | Val | |
| | | | 180 | | | | | 185 | | | | | 190 | | | |

| cgc | ccg | cgt | gga | cca | gca | ccg | cac | gta | caa | gtt | cgg | cgc | gtg | ctg | gag | 624 |
|---|---|---|---|---|---|---|---|---|---|---|---|---|---|---|---|---|
| Arg | Pro | Arg | Gly | Pro | Ala | Pro | His | Val | Gln | Val | Arg | Arg | Val | Leu | Glu | |
| | | 195 | | | | | 200 | | | | | 205 | | | | |

| cga | cga | cag | ctt | caa | gcg | ggg | cgt | gga | cgt | gat | gcg | att | cct | gac | gcc | 672 |
|---|---|---|---|---|---|---|---|---|---|---|---|---|---|---|---|---|
| Arg | Arg | Gln | Leu | Gln | Ala | Gly | Arg | Gly | Arg | Asp | Ala | Ile | Pro | Asp | Ala | |
| | | 210 | | | | | 215 | | | | | 220 | | | | |

| gtt | cta | cca | gca | gcc | ccc | gca | ccg | gga | ggt | ggt | gaa | cta | ctg | gta | ccg | 720 |
|---|---|---|---|---|---|---|---|---|---|---|---|---|---|---|---|---|
| Val | Leu | Pro | Ala | Ala | Pro | Ala | Pro | Gly | Gly | Gly | Glu | Leu | Leu | Val | Pro | |
| 225 | | | | | 230 | | | | | 235 | | | | | 240 | |

```
caa gaa cgg ccg gac gct ccc gcg ggc cca cgc cgc cgc cac gcc gta        768
Gln Glu Arg Pro Asp Ala Pro Ala Gly Pro Arg Arg Arg His Ala Val
                245                 250                 255 cgc cat cga ccc cgc gcg gcc ctc ggg ctc gcc gag gcc ccg gcc            816
Arg His Arg Pro Arg Ala Ala Leu Gly Gly Leu Ala Glu Ala Pro Ala
            260                 265                 270 ccg gcc ccg gcc ccg gcc ccg gcc gaa gcc cga gcc cgc ccc ggc gac        864
Pro Ala Pro Ala Pro Ala Pro Ala Glu Ala Arg Ala Arg Pro Gly Asp
        275                 280                 285 gcc cgc gcc ccc cga ccg cct gcc cga gcc ggc gac gcg gga cca cgc        912
Ala Arg Ala Pro Arg Pro Pro Ala Arg Ala Gly Asp Ala Gly Pro Arg
290                 295                 300 cgc cgg ggg ccg ccc cac gcc gcg acc ccc gag gcc cga gac gcc gca        960
Arg Arg Gly Pro Pro His Ala Ala Thr Pro Glu Ala Arg Asp Ala Ala
305                 310                 315                 320 ccg ccc ctt cgc ccc gcc ggc cgt cgt gcc cag cgg gtg gcc gca gcc       1008
Pro Pro Leu Arg Pro Ala Gly Arg Arg Ala Gln Arg Val Ala Ala Ala
                325                 330                 335 cgc gga gcc gtt cca gcc gcg gac ccc cgc cgc gcc ggg cgt ctc gcg       1056
Arg Gly Ala Val Pro Ala Ala Asp Pro Arg Arg Ala Gly Arg Leu Ala
            340                 345                 350 cca ccg ctc ggt gat cgt cgg cac ggg cac cgc gat ggg cgc gct cct       1104
Pro Pro Leu Gly Asp Arg Arg His Gly His Arg Asp Gly Arg Ala Pro
        355                 360                 365 ggt ggg cgt gtg cgt cta cat ctt ctt ccg cct gag ggg ggc gaa ggg       1152
Gly Gly Arg Val Arg Leu His Leu Leu Pro Pro Glu Gly Gly Glu Gly
370                 375                 380 gta tcg cct cct ggg cgg tcc cgc gga cgc cga cga gct aaa agc gca       1200
Val Ser Pro Pro Gly Arg Ser Arg Gly Arg Arg Arg Ala Lys Ser Ala
385                 390                 395                 400 gcc cgg tcc gta g                                                     1213
Ala Arg Ser Val <210> SEQ ID NO 7
<211> LENGTH: 15
<212> TYPE: DNA
<213> ORGANISM: Aujesky's Disease Virus (NIA3 Strain)

<400> SEQUENCE: 7
gatgctgctc gcagc                                                        15

<210> SEQ ID NO 8
<211> LENGTH: 19
<212> TYPE: DNA
<213> ORGANISM: Pseudorabies virus

<400> SEQUENCE: 8
gctgcgagca gcatctgca                                                    19

<210> SEQ ID NO 9
<211> LENGTH: 32
<212> TYPE: DNA
<213> ORGANISM: Porcine Flu Virus (SIV, H1N1 "SW" Strain

<400> SEQUENCE: 9
gttctgcagc acccgggagc aaaagcaggg ga                                     32

<210> SEQ ID NO 10
<211> LENGTH: 33
<212> TYPE: DNA
<213> ORGANISM: Porcine Flu Virus (SIV, H1N1 "SW" Strain
```

<210> SEQ ID NO 11
<211> LENGTH: 1701
<212> TYPE: DNA
<213> ORGANISM: Porcine Flu Virus (SIV, H1N1 "SW" Strain
<220> FEATURE:
<221> NAME/KEY: CDS
<222> LOCATION: (1)..(1698)
<223> OTHER INFORMATION:

<400> SEQUENCE: 11

```
atg gaa gca aaa cta ttc gta tta ttc tgt aca ttc act gcg ctg aaa        48
Met Glu Ala Lys Leu Phe Val Leu Phe Cys Thr Phe Thr Ala Leu Lys
1               5                   10                  15 gct gac acc atc tgt gta gga tac cat gct aac aat tcc aca gat act        96
Ala Asp Thr Ile Cys Val Gly Tyr His Ala Asn Asn Ser Thr Asp Thr
            20                  25                  30 gtc gac aca ata ctg gag aag aat gtg act gtg act cat tca gtt aat       144
Val Asp Thr Ile Leu Glu Lys Asn Val Thr Val Thr His Ser Val Asn
        35                  40                  45 tta cta gaa aac agt cat aat gga aaa ctc tgc agc ctg aat gga gta       192
Leu Leu Glu Asn Ser His Asn Gly Lys Leu Cys Ser Leu Asn Gly Val
    50                  55                  60 gcc ccc ttg caa cta ggg aag tgc aac gta gca ggg tgg atc ctt ggc       240
Ala Pro Leu Gln Leu Gly Lys Cys Asn Val Ala Gly Trp Ile Leu Gly
65                  70                  75                  80 aac cca gaa tgt gac ctg ttg ctc aca gcg aat tca tgg tct tac ata       288
Asn Pro Glu Cys Asp Leu Leu Leu Thr Ala Asn Ser Trp Ser Tyr Ile
                85                  90                  95 ata gag act tca aat tca gaa aat gga aca tgc tac ccc gga gaa ttc       336
Ile Glu Thr Ser Asn Ser Glu Asn Gly Thr Cys Tyr Pro Gly Glu Phe
            100                 105                 110 att gat tat gag gaa tta agg gag cag ctg agt tca gtg tct tca ttt       384
Ile Asp Tyr Glu Glu Leu Arg Glu Gln Leu Ser Ser Val Ser Ser Phe
        115                 120                 125 gaa agg ttt gaa att ttc cca aaa gca aac tca tgg cca aat cat gag       432
Glu Arg Phe Glu Ile Phe Pro Lys Ala Asn Ser Trp Pro Asn His Glu
    130                 135                 140 aca acc aaa ggt att aca gct gca tgc tct tac tct gga acc ccc agt       480
Thr Thr Lys Gly Ile Thr Ala Ala Cys Ser Tyr Ser Gly Thr Pro Ser
145                 150                 155                 160 ttt tat cgg aat ttg cta tgg ata gta gag agg gaa aat tcc tat cct       528
Phe Tyr Arg Asn Leu Leu Trp Ile Val Glu Arg Glu Asn Ser Tyr Pro
                165                 170                 175 aaa ctc agc aaa tca tac aca aac aaa ggg aaa gaa gtg ctt ata            576
Lys Leu Ser Lys Ser Tyr Thr Asn Asn Lys Gly Lys Glu Val Leu Ile
            180                 185                 190 atc tgg gga gtg cac cac cct cca act acc aat gac caa caa agc ctc       624
Ile Trp Gly Val His His Pro Pro Thr Thr Asn Asp Gln Gln Ser Leu
        195                 200                 205 tat cag aat gct gat gca tat gtt tca gtt ggg tca tca aaa tac aac       672
Tyr Gln Asn Ala Asp Ala Tyr Val Ser Val Gly Ser Ser Lys Tyr Asn
    210                 215                 220 cga agg ttc aca cca gaa ata gca gct aga cct aaa gtc aaa gga caa       720
Arg Arg Phe Thr Pro Glu Ile Ala Ala Arg Pro Lys Val Lys Gly Gln
225                 230                 235                 240 gca ggc aga atg aat tat tat tgg aca ttg tta gat caa gga gac acc       768
Ala Gly Arg Met Asn Tyr Tyr Trp Thr Leu Leu Asp Gln Gly Asp Thr
                245                 250                 255
```

```
ata acg ttt gaa gcc act ggg aac tta ata gca cca tgg tac gcc ttc      816
Ile Thr Phe Glu Ala Thr Gly Asn Leu Ile Ala Pro Trp Tyr Ala Phe
            260                 265                 270 gca ttg aat aag ggc tct ggt tct gga att ata acg tcg gat act ccg      864
Ala Leu Asn Lys Gly Ser Gly Ser Gly Ile Ile Thr Ser Asp Thr Pro
            275                 280                 285 gtt cac aat tgt gat aca aag tgc caa acc cct cat ggg gcc ttg aac      912
Val His Asn Cys Asp Thr Lys Cys Gln Thr Pro His Gly Ala Leu Asn
        290                 295                 300 agt agt ctt cct ttt cag aac gta cat ccc atc act att gga gaa tgc      960
Ser Ser Leu Pro Phe Gln Asn Val His Pro Ile Thr Ile Gly Glu Cys
305                 310                 315                 320 ccc aaa tat gtt aaa agc acc aaa ctg aga atg gca aca gga cta agg     1008
Pro Lys Tyr Val Lys Ser Thr Lys Leu Arg Met Ala Thr Gly Leu Arg
                325                 330                 335 aac gtc ccc tct att caa tcc aga gga ctt ttc gga gca att gct gga     1056
Asn Val Pro Ser Ile Gln Ser Arg Gly Leu Phe Gly Ala Ile Ala Gly
                340                 345                 350 ttc att gaa gga gga tgg aca gga atg ata gat ggg tgg tat ggg tat     1104
Phe Ile Glu Gly Gly Trp Thr Gly Met Ile Asp Gly Trp Tyr Gly Tyr
                355                 360                 365 cac cat cag aat gag cag gga tct ggt tac gca gct gat cag aaa agc     1152
His His Gln Asn Glu Gln Gly Ser Gly Tyr Ala Ala Asp Gln Lys Ser
        370                 375                 380 aca caa att gca att gac ggg atc agc aac aaa gtg aac tca gta att     1200
Thr Gln Ile Ala Ile Asp Gly Ile Ser Asn Lys Val Asn Ser Val Ile
385                 390                 395                 400 gag aaa atg aac act caa ttc act gca gtg ggc aag gaa ttc aat gat     1248
Glu Lys Met Asn Thr Gln Phe Thr Ala Val Gly Lys Glu Phe Asn Asp
                405                 410                 415 cta gaa aaa agg att gag aat ttg aat aag aaa gtc gat gat ggg ttt     1296
Leu Glu Lys Arg Ile Glu Asn Leu Asn Lys Lys Val Asp Asp Gly Phe
            420                 425                 430 ttg gat gtt tgg aca tat aat gct gag ttg ctc gtt ttg ctc gag aac     1344
Leu Asp Val Trp Thr Tyr Asn Ala Glu Leu Leu Val Leu Leu Glu Asn
            435                 440                 445 gaa agg act cta gat ttc cat gac ttt aac gta aga aat tta tat gaa     1392
Glu Arg Thr Leu Asp Phe His Asp Phe Asn Val Arg Asn Leu Tyr Glu
450                 455                 460 aag gtc aag tca caa ttg aga aac aat gcc aaa gaa atc ggg aat ggt     1440
Lys Val Lys Ser Gln Leu Arg Asn Asn Ala Lys Glu Ile Gly Asn Gly
465                 470                 475                 480 tgt ttt gag ttc tat cac aaa tgt gat gac gaa tgc atg aag agc gta     1488
Cys Phe Glu Phe Tyr His Lys Cys Asp Asp Glu Cys Met Lys Ser Val
                485                 490                 495 aag aat ggc aca tat aac tac ccc aaa tat tca gaa gaa tcc aaa ttg     1536
Lys Asn Gly Thr Tyr Asn Tyr Pro Lys Tyr Ser Glu Glu Ser Lys Leu
                500                 505                 510 aat aga gag gaa ata gac ggt gtg aaa cta gaa tca atg gga gtt tac     1584
Asn Arg Glu Glu Ile Asp Gly Val Lys Leu Glu Ser Met Gly Val Tyr
            515                 520                 525 cag att ttg gcg atc tac tcc aca gtc gcc agt tcc ctg gtc ttg tta     1632
Gln Ile Leu Ala Ile Tyr Ser Thr Val Ala Ser Ser Leu Val Leu Leu
            530                 535                 540 gtc tcc ctg ggg gca atc agc ttc tgg atg tgt tct aat ggg tca ttg     1680
Val Ser Leu Gly Ala Ile Ser Phe Trp Met Cys Ser Asn Gly Ser Leu
545                 550                 555                 560 caa tgc aga ata tgc att taa                                         1701
Gln Cys Arg Ile Cys Ile
```

```
<210> SEQ ID NO 12
<211> LENGTH: 36
<212> TYPE: DNA
<213> ORGANISM: Porcine Flu Virus (SIV, H1N1 "SW" Strain

<400> SEQUENCE: 12
ccggtcgacc gggataatca ctcactgagt gacatc                              36

<210> SEQ ID NO 13
<211> LENGTH: 33
<212> TYPE: DNA
<213> ORGANISM: Porcine Flu Virus (SIV, H1N1 "SW" Strain

<400> SEQUENCE: 13
ttgcggccgc tgtagaaaca agggtatttt tct                                 33

<210> SEQ ID NO 14
<211> LENGTH: 1497
<212> TYPE: DNA
<213> ORGANISM: Swine Influenza Virus
<220> FEATURE:
<221> NAME/KEY: CDS
<222> LOCATION: (1)..(1494)
<223> OTHER INFORMATION:

<400> SEQUENCE: 14
```

| | | | | | | | | | | | | | | | | |
|---|---|---|---|---|---|---|---|---|---|---|---|---|---|---|---|---|
| atg | gcg | tct | caa | ggc | acc | aaa | cga | tct | tat | gag | cag | atg | gaa | acc | ggt | 48 |
| Met | Ala | Ser | Gln | Gly | Thr | Lys | Arg | Ser | Tyr | Glu | Gln | Met | Glu | Thr | Gly | |
| 1 | | | | 5 | | | | | 10 | | | | | 15 | | |
| gga | gaa | cgc | cag | aat | gct | act | gaa | atc | aga | gca | tct | gtt | ggg | gga | atg | 96 |
| Gly | Glu | Arg | Gln | Asn | Ala | Thr | Glu | Ile | Arg | Ala | Ser | Val | Gly | Gly | Met | |
| | | | 20 | | | | | 25 | | | | | 30 | | | |
| gtt | ggt | gga | att | gga | aga | ttc | tac | ata | cag | atg | tgc | act | gaa | ctc | aaa | 144 |
| Val | Gly | Gly | Ile | Gly | Arg | Phe | Tyr | Ile | Gln | Met | Cys | Thr | Glu | Leu | Lys | |
| | | 35 | | | | | 40 | | | | | 45 | | | | |
| ctc | agt | gac | tat | gaa | ggg | agg | ctg | atc | cag | aac | agc | ata | aca | ata | gag | 192 |
| Leu | Ser | Asp | Tyr | Glu | Gly | Arg | Leu | Ile | Gln | Asn | Ser | Ile | Thr | Ile | Glu | |
| | 50 | | | | | 55 | | | | | 60 | | | | | |
| aga | atg | gtt | ctc | tct | gca | ttt | gat | gag | agg | agg | aac | aaa | tac | ctg | gaa | 240 |
| Arg | Met | Val | Leu | Ser | Ala | Phe | Asp | Glu | Arg | Arg | Asn | Lys | Tyr | Leu | Glu | |
| 65 | | | | | 70 | | | | | 75 | | | | | 80 | |
| gaa | cat | ccc | agt | gcg | ggg | aag | gac | cca | aag | aaa | act | gga | ggt | cca | atc | 288 |
| Glu | His | Pro | Ser | Ala | Gly | Lys | Asp | Pro | Lys | Lys | Thr | Gly | Gly | Pro | Ile | |
| | | | | 85 | | | | | 90 | | | | | 95 | | |
| tac | aga | aag | aga | gac | gga | aaa | tgg | atg | aga | gag | ctg | att | cta | tat | gac | 336 |
| Tyr | Arg | Lys | Arg | Asp | Gly | Lys | Trp | Met | Arg | Glu | Leu | Ile | Leu | Tyr | Asp | |
| | | | 100 | | | | | 105 | | | | | 110 | | | |
| aaa | gag | gag | atc | agg | agg | att | tgg | cgt | caa | gca | aac | aat | ggt | gaa | gat | 384 |
| Lys | Glu | Glu | Ile | Arg | Arg | Ile | Trp | Arg | Gln | Ala | Asn | Asn | Gly | Glu | Asp | |
| | | 115 | | | | | 120 | | | | | 125 | | | | |
| gct | act | gct | ggt | ctc | act | cat | ctg | atg | att | tgg | cat | tcc | aac | ctg | aat | 432 |
| Ala | Thr | Ala | Gly | Leu | Thr | His | Leu | Met | Ile | Trp | His | Ser | Asn | Leu | Asn | |
| | 130 | | | | | 135 | | | | | 140 | | | | | |
| gat | gcc | aca | tat | cag | aga | aca | aga | gct | ctc | gtg | cgt | act | ggg | atg | gac | 480 |
| Asp | Ala | Thr | Tyr | Gln | Arg | Thr | Arg | Ala | Leu | Val | Arg | Thr | Gly | Met | Asp | |
| 145 | | | | | 150 | | | | | 155 | | | | | 160 | |
| ccc | aga | atg | tgc | tct | ctg | atg | caa | gga | tca | act | ctc | ccg | agg | aga | tct | 528 |
| Pro | Arg | Met | Cys | Ser | Leu | Met | Gln | Gly | Ser | Thr | Leu | Pro | Arg | Arg | Ser | |
| | | | | 165 | | | | | 170 | | | | | 175 | | |
| gga | gct | gct | ggt | gcg | gca | gta | aag | gga | gtt | ggg | acg | atg | gta | atg | gaa | 576 |

-continued

```
                Gly Ala Ala Gly Ala Ala Val Lys Gly Val Gly Thr Met Val Met Glu
                                180                 185                 190 ctg att cgg atg ata aaa gcg ggg atc aat gat cgg aac ttc tgg aga            624
Leu Ile Arg Met Ile Lys Ala Gly Ile Asn Asp Arg Asn Phe Trp Arg
            195                 200                 205 ggc gaa aat gga cga aga aca aga att gca tat gag aga atg tgc aac            672
Gly Glu Asn Gly Arg Arg Thr Arg Ile Ala Tyr Glu Arg Met Cys Asn
210                 215                 220 atc ctc aaa ggg aaa ttt cag aca gca gcg caa caa gca atg atg gac            720
Ile Leu Lys Gly Lys Phe Gln Thr Ala Ala Gln Gln Ala Met Met Asp
225                 230                 235                 240 cag gtg cga gaa atg aca aat cct ggg aat gct gag act gaa gac ctt            768
Gln Val Arg Glu Met Thr Asn Pro Gly Asn Ala Glu Thr Glu Asp Leu
                245                 250                 255 atc ttt ctg gca cga tct gca ctc att ctg aga gga tca gtg gct cat            816
Ile Phe Leu Ala Arg Ser Ala Leu Ile Leu Arg Gly Ser Val Ala His
            260                 265                 270 aaa tcc tgc ctg cct gct tgt gta tat gga ctt gtt gtg gca agt gga            864
Lys Ser Cys Leu Pro Ala Cys Val Tyr Gly Leu Val Val Ala Ser Gly
        275                 280                 285 tat gac ttt gaa aga gaa ggg tac tct cta gtc gga ata gat cct ttc            912
Tyr Asp Phe Glu Arg Glu Gly Tyr Ser Leu Val Gly Ile Asp Pro Phe
    290                 295                 300 cgt ctg ctc caa aac agc cag gtg ttc agc ctc att aga cca aat gag            960
Arg Leu Leu Gln Asn Ser Gln Val Phe Ser Leu Ile Arg Pro Asn Glu
305                 310                 315                 320 aat cca gca cat aag agt cag ctg gta tgg atg gca tgc cat tct gca           1008
Asn Pro Ala His Lys Ser Gln Leu Val Trp Met Ala Cys His Ser Ala
                325                 330                 335 gca ttt gaa gat ctg aga gtg tca agt ttc atc aga ggg aca aga gtg           1056
Ala Phe Glu Asp Leu Arg Val Ser Ser Phe Ile Arg Gly Thr Arg Val
            340                 345                 350 gtc cca aga gga caa ctg tcc acc aga gga gtt caa att gct tca aat           1104
Val Pro Arg Gly Gln Leu Ser Thr Arg Gly Val Gln Ile Ala Ser Asn
        355                 360                 365 gaa aac atg gaa aca atg gag tcc agt act ctt gaa ctg aga agc aaa           1152
Glu Asn Met Glu Thr Met Glu Ser Ser Thr Leu Glu Leu Arg Ser Lys
    370                 375                 380 tac tgg gct ata aga acc agg agc gga gga aac acc aac caa cag aga           1200
Tyr Trp Ala Ile Arg Thr Arg Ser Gly Gly Asn Thr Asn Gln Gln Arg
385                 390                 395                 400 gca tct gca ggg caa atc agt gta caa ctt act ttc tcg gta cag aga           1248
Ala Ser Ala Gly Gln Ile Ser Val Gln Leu Thr Phe Ser Val Gln Arg
                405                 410                 415 aat ctt cct ttc gag aga gcg acc atc atg gca gca ttt aca ggg aac           1296
Asn Leu Pro Phe Glu Arg Ala Thr Ile Met Ala Ala Phe Thr Gly Asn
            420                 425                 430 act gaa ggc aga aca tct gac atg agg act gaa att ata aga atg atg           1344
Thr Glu Gly Arg Thr Ser Asp Met Arg Thr Glu Ile Ile Arg Met Met
        435                 440                 445 gaa agt gcc aga cca gaa gat gtg tcc ttc cag ggg cgg gga gtc ttc           1392
Glu Ser Ala Arg Pro Glu Asp Val Ser Phe Gln Gly Arg Gly Val Phe
    450                 455                 460 gag ctc tcg gac gaa aag gca acg aac ccg atc gtg cct tcc ttt gac           1440
Glu Leu Ser Asp Glu Lys Ala Thr Asn Pro Ile Val Pro Ser Phe Asp
465                 470                 475                 480 atg agt aat gag gga tct tat ttc ttc gga gac aat gca gag gag tat           1488
Met Ser Asn Glu Gly Ser Tyr Phe Phe Gly Asp Asn Ala Glu Glu Tyr
                485                 490                 495
```

-continued

```
gac aat taa                                                       1497
Asp Asn <210> SEQ ID NO 15
<211> LENGTH: 31
<212> TYPE: DNA
<213> ORGANISM: Porcine Flu Virus (SIV, H1N1 "SW" Strain

<400> SEQUENCE: 15
gttctgcagg caggggataa ttctatcaac c                                  31

<210> SEQ ID NO 16
<211> LENGTH: 36
<212> TYPE: DNA
<213> ORGANISM: Porcine Flu Virus

<400> SEQUENCE: 16
ttgcggccgc aagggtgttt ttaattacta atatac                             36

<210> SEQ ID NO 17
<211> LENGTH: 1701
<212> TYPE: DNA
<213> ORGANISM: Swine Influenza Virus
<220> FEATURE:
<221> NAME/KEY: CDS
<222> LOCATION: (1)..(1698)
<223> OTHER INFORMATION:

<400> SEQUENCE: 17 atg aag act gtc att gcc ttg agc tac att ttc tgt ctg gtt ctt ggc      48
Met Lys Thr Val Ile Ala Leu Ser Tyr Ile Phe Cys Leu Val Leu Gly
1               5                   10                  15 caa gac ctt cca gaa aat ggc agc agc aca gca aag cct ggt ctg gga      96
Gln Asp Leu Pro Glu Asn Gly Ser Ser Thr Ala Lys Pro Gly Leu Gly
            20                  25                  30 cat cat gcg gtg cca aac gga acg tta gtg aaa aca atc acg aat gat     144
His His Ala Val Pro Asn Gly Thr Leu Val Lys Thr Ile Thr Asn Asp
        35                  40                  45 cag atc gaa gtg act aat gct act gag ctg gtc cag agt ttc tca atg     192
Gln Ile Glu Val Thr Asn Ala Thr Glu Leu Val Gln Ser Phe Ser Met
    50                  55                  60 ggt aaa ata tgc aac aat cct cat cga gtt ctt gat gga gca aac tgt     240
Gly Lys Ile Cys Asn Asn Pro His Arg Val Leu Asp Gly Ala Asn Cys
65                  70                  75                  80 aca ctg ata gat gct cta ttg ggg gac cct cat tgt gat ggc ttt caa     288
Thr Leu Ile Asp Ala Leu Leu Gly Asp Pro His Cys Asp Gly Phe Gln
                85                  90                  95 aat gag aaa tgg gac ctt ttc gtt gaa cgc agc aaa tgc ttc agc aac     336
Asn Glu Lys Trp Asp Leu Phe Val Glu Arg Ser Lys Cys Phe Ser Asn
            100                 105                 110 tgt tac cct tat gat gtg cca gat tat gcc tcc ctt agg tca cta att     384
Cys Tyr Pro Tyr Asp Val Pro Asp Tyr Ala Ser Leu Arg Ser Leu Ile
        115                 120                 125 gcc tct tcg ggc act ttg gag ttt atc aat gaa ggt ttc aat tgg act     432
Ala Ser Ser Gly Thr Leu Glu Phe Ile Asn Glu Gly Phe Asn Trp Thr
    130                 135                 140 ggg gtc act cag aac gga gga agc aat gct tgc aag agg ggg cct gat     480
Gly Val Thr Gln Asn Gly Gly Ser Asn Ala Cys Lys Arg Gly Pro Asp
145                 150                 155                 160 agc ggt ttc ttc agt agg ctg aac tgg ttg tac aaa tca gga aac aca     528
Ser Gly Phe Phe Ser Arg Leu Asn Trp Leu Tyr Lys Ser Gly Asn Thr
                165                 170                 175
```

```
                                              -continued tac ccg atg ctg aac gtg act atg cca aac agt gat aat ttt gac aaa     576
Tyr Pro Met Leu Asn Val Thr Met Pro Asn Ser Asp Asn Phe Asp Lys
        180                 185                 190 tta tac att tgg ggg gtt cac cat ccg agc aca gac agg gaa caa acc     624
Leu Tyr Ile Trp Gly Val His His Pro Ser Thr Asp Arg Glu Gln Thr
            195                 200                 205 aac cta tat gtt caa gta tca ggg aaa gca acg gtt ttc acc aag aga     672
Asn Leu Tyr Val Gln Val Ser Gly Lys Ala Thr Val Phe Thr Lys Arg
    210                 215                 220 agc cag cag acc ata atc ccg aac agt cgg tct aga ccc tgg gta agg     720
Ser Gln Gln Thr Ile Ile Pro Asn Ser Arg Ser Arg Pro Trp Val Arg
225                 230                 235                 240 ggt ctg tct agt aga ata agc atc cat tgg aca ata gtt aaa ccg ggg     768
Gly Leu Ser Ser Arg Ile Ser Ile His Trp Thr Ile Val Lys Pro Gly
                245                 250                 255 gac att ctg ata att aat agt aat ggg aac cta att gct cct cgg ggt     816
Asp Ile Leu Ile Ile Asn Ser Asn Gly Asn Leu Ile Ala Pro Arg Gly
            260                 265                 270 tac ttc aaa atg cac aat ggg aga agc tca ata atg agg tca gat gca     864
Tyr Phe Lys Met His Asn Gly Arg Ser Ser Ile Met Arg Ser Asp Ala
        275                 280                 285 cct att ggc acc tgc agt tct gaa tgc atc act cca aat gga agc atc     912
Pro Ile Gly Thr Cys Ser Ser Glu Cys Ile Thr Pro Asn Gly Ser Ile
    290                 295                 300 cca aat gac aaa ccc ttt caa aac gta aac aag atc aca tat ggg gca     960
Pro Asn Asp Lys Pro Phe Gln Asn Val Asn Lys Ile Thr Tyr Gly Ala
305                 310                 315                 320 tgt cct aag tat gtt aaa caa aac act ctg aag ttg gca aca ggg atg    1008
Cys Pro Lys Tyr Val Lys Gln Asn Thr Leu Lys Leu Ala Thr Gly Met
                325                 330                 335 cgg aat ata ccg gaa aaa caa act aga ggc ata ttc ggc gca ata gca    1056
Arg Asn Ile Pro Glu Lys Gln Thr Arg Gly Ile Phe Gly Ala Ile Ala
            340                 345                 350 ggt ttc ata gag aat ggt tgg gaa gga atg gta gac ggc tgg tac ggt    1104
Gly Phe Ile Glu Asn Gly Trp Glu Gly Met Val Asp Gly Trp Tyr Gly
        355                 360                 365 ttc aga cat caa aat tct gag ggc aca gga caa gca gca gac ctt aaa    1152
Phe Arg His Gln Asn Ser Glu Gly Thr Gly Gln Ala Ala Asp Leu Lys
    370                 375                 380 agc acc caa gca gcc atc gac caa atc aac ggg aaa ctg aat aga cta    1200
Ser Thr Gln Ala Ala Ile Asp Gln Ile Asn Gly Lys Leu Asn Arg Leu
385                 390                 395                 400 atc gag aag acg aac ggg aaa ttc cat caa atc gaa aag gaa ttc tca    1248
Ile Glu Lys Thr Asn Gly Lys Phe His Gln Ile Glu Lys Glu Phe Ser
                405                 410                 415 ata gta gaa ggg aga att cag gac ctc gag aaa tac gtt gaa gac act    1296
Ile Val Glu Gly Arg Ile Gln Asp Leu Glu Lys Tyr Val Glu Asp Thr
            420                 425                 430 aaa ata gat ctc tgg tct tac aat gcg gaa ctt ctt gtc gct ctg gag    1344
Lys Ile Asp Leu Trp Ser Tyr Asn Ala Glu Leu Leu Val Ala Leu Glu
        435                 440                 445 aac caa cat aca att gat ctg act gac tcg gaa atg agc aaa ctg ttt    1392
Asn Gln His Thr Ile Asp Leu Thr Asp Ser Glu Met Ser Lys Leu Phe
    450                 455                 460 gaa aaa aca agg agg caa ctg agg gaa aat gct gag gac atg gga aac    1440
Glu Lys Thr Arg Arg Gln Leu Arg Glu Asn Ala Glu Asp Met Gly Asn
465                 470                 475                 480 ggt tgc ctt caa ata tac cac aaa tgt gac aat gct tgc ata gag tca    1488
Gly Cys Leu Gln Ile Tyr His Lys Cys Asp Asn Ala Cys Ile Glu Ser
                485                 490                 495
```

-continued

```
atc aga aat ggg act tat gac cat aat gaa tac aga gac gaa gca tta     1536
Ile Arg Asn Gly Thr Tyr Asp His Asn Glu Tyr Arg Asp Glu Ala Leu
            500                 505                 510 aac aac cga ttt cag atc aaa ggt gtt gag ctg aag tcg gga tac aaa     1584
Asn Asn Arg Phe Gln Ile Lys Gly Val Glu Leu Lys Ser Gly Tyr Lys
        515                 520                 525 gac tgg atc ctg tgg att tcc tct gcc ata tca tgc ttt ttg ctt tgt     1632
Asp Trp Ile Leu Trp Ile Ser Ser Ala Ile Ser Cys Phe Leu Leu Cys
    530                 535                 540 gtt gtt ttg cta gga ttt atc atg tgg gcc tgc cag aaa ggc aac att     1680
Val Val Leu Leu Gly Phe Ile Met Trp Ala Cys Gln Lys Gly Asn Ile
545                 550                 555                 560 agg tgc aac att tgc atc tga                                         1701
Arg Cys Asn Ile Cys Ile
                565

<210> SEQ ID NO 18
<211> LENGTH: 1497
<212> TYPE: DNA
<213> ORGANISM: Swine Influenza Virus
<220> FEATURE:
<221> NAME/KEY: CDS
<222> LOCATION: (1)..(1494)
<223> OTHER INFORMATION:

<400> SEQUENCE: 18 atg gcg tct caa ggc act aaa cga tct tat gag cag atg gaa acc ggt       48
Met Ala Ser Gln Gly Thr Lys Arg Ser Tyr Glu Gln Met Glu Thr Gly
1               5                   10                  15 gga gaa cgc cgg aat gct act gaa atc aga gca tct gtt ggg gga atg       96
Gly Glu Arg Arg Asn Ala Thr Glu Ile Arg Ala Ser Val Gly Gly Met
            20                  25                  30 gtt ggt gga att gga aga ttc tac ata cag atg tgc act aaa ctc aaa      144
Val Gly Gly Ile Gly Arg Phe Tyr Ile Gln Met Cys Thr Lys Leu Lys
        35                  40                  45 ctc agt gac tat gaa ggg agg ctg atc cag aac agc ata aca ata gag      192
Leu Ser Asp Tyr Glu Gly Arg Leu Ile Gln Asn Ser Ile Thr Ile Glu
    50                  55                  60 aga atg gtt ctc tct gca ttt gat gag agg agg aac aaa tac ctg gaa      240
Arg Met Val Leu Ser Ala Phe Asp Glu Arg Arg Asn Lys Tyr Leu Glu
65                  70                  75                  80 gaa cat ccc agt gcg ggg aag gac cca aag aaa act gga ggt cca ata      288
Glu His Pro Ser Ala Gly Lys Asp Pro Lys Lys Thr Gly Gly Pro Ile
                85                  90                  95 tac aga aag aga gac gga aaa tgg atg aga gag ctg att atg tat gac      336
Tyr Arg Lys Arg Asp Gly Lys Trp Met Arg Glu Leu Ile Met Tyr Asp
            100                 105                 110 aaa gag gag atc agg agg att tgg cgt caa gca aac aat ggt gaa gat      384
Lys Glu Glu Ile Arg Arg Ile Trp Arg Gln Ala Asn Asn Gly Glu Asp
        115                 120                 125 gct act gct ggt ctc act cat ctg atg att tgg cat tcc aac ctg aat      432
Ala Thr Ala Gly Leu Thr His Leu Met Ile Trp His Ser Asn Leu Asn
    130                 135                 140 gat gcc aca tat cag aga aca aga gct ctc gtg cgt act ggg atg gac      480
Asp Ala Thr Tyr Gln Arg Thr Arg Ala Leu Val Arg Thr Gly Met Asp
145                 150                 155                 160 ccc aga atg tgc tct ctg atg caa gga tca act ctc ccg agg aga tct      528
Pro Arg Met Cys Ser Leu Met Gln Gly Ser Thr Leu Pro Arg Arg Ser
                165                 170                 175 gga gct gct ggt gca gca gta aag gga gtt ggg acg atg gta atg gaa      576
Gly Ala Ala Gly Ala Ala Val Lys Gly Val Gly Thr Met Val Met Glu
```

|     |     |     |     |     |     |     |     |     |     |     |     |     |     |     |     |
|---|---|---|---|---|---|---|---|---|---|---|---|---|---|---|---|
|     |     |     |     | 180 |     |     |     |     | 185 |     |     |     |     | 190 |     |
| ctg | att | cgg | atg | ata | aag | cgg | ggg | atc | aat | gat | cgg | aac | ttc | tgg | aga | 624 |
| Leu | Ile | Arg | Met | Ile | Lys | Arg | Gly | Ile | Asn | Asp | Arg | Asn | Phe | Trp | Arg |     |
|     |     |     | 195 |     |     |     | 200 |     |     |     | 205 |     |     |     |     |     |
| ggc | gaa | aat | gga | cga | aga | aca | aga | att | gca | tat | gag | aga | atg | tgc | aac | 672 |
| Gly | Glu | Asn | Gly | Arg | Arg | Thr | Arg | Ile | Ala | Tyr | Glu | Arg | Met | Cys | Asn |     |
|     | 210 |     |     |     |     | 215 |     |     |     |     | 220 |     |     |     |     |     |
| atc | ctc | aaa | ggg | aaa | ttt | cag | aca | gca | gcg | caa | cga | gca | acg | atg | gac | 720 |
| Ile | Leu | Lys | Gly | Lys | Phe | Gln | Thr | Ala | Ala | Gln | Arg | Ala | Thr | Met | Asp |     |
| 225 |     |     |     |     | 230 |     |     |     |     | 235 |     |     |     |     | 240 |     |
| cag | gtg | cga | gaa | agc | aga | aat | cct | ggg | aat | gct | gag | att | gaa | gac | ctt | 768 |
| Gln | Val | Arg | Glu | Ser | Arg | Asn | Pro | Gly | Asn | Ala | Glu | Ile | Glu | Asp | Leu |     |
|     |     |     |     | 245 |     |     |     |     | 250 |     |     |     |     | 255 |     |     |
| atc | ttt | cta | gca | cga | tct | gca | ctc | att | ctg | aga | gga | tca | gtg | gct | cat | 816 |
| Ile | Phe | Leu | Ala | Arg | Ser | Ala | Leu | Ile | Leu | Arg | Gly | Ser | Val | Ala | His |     |
|     |     |     |     | 260 |     |     |     |     | 265 |     |     |     |     | 270 |     |     |
| aaa | tcc | tgt | ctg | cct | gct | tgt | gta | tat | gga | ctt | gtt | gtg | gca | agt | gga | 864 |
| Lys | Ser | Cys | Leu | Pro | Ala | Cys | Val | Tyr | Gly | Leu | Val | Val | Ala | Ser | Gly |     |
|     |     | 275 |     |     |     |     | 280 |     |     |     |     | 285 |     |     |     |     |
| tat | gac | ttt | gaa | aga | gaa | ggg | tac | tct | cta | gtc | gga | ata | gat | cct | ttc | 912 |
| Tyr | Asp | Phe | Glu | Arg | Glu | Gly | Tyr | Ser | Leu | Val | Gly | Ile | Asp | Pro | Phe |     |
|     | 290 |     |     |     |     | 295 |     |     |     |     | 300 |     |     |     |     |     |
| cgt | ctg | ctc | cag | aac | agc | cag | gtg | ttc | agc | ctc | att | aga | cca | aat | gag | 960 |
| Arg | Leu | Leu | Gln | Asn | Ser | Gln | Val | Phe | Ser | Leu | Ile | Arg | Pro | Asn | Glu |     |
| 305 |     |     |     |     | 310 |     |     |     |     | 315 |     |     |     |     | 320 |     |
| aat | cca | gca | cat | aag | agt | cag | ttg | gta | tgg | atg | gca | tgc | cat | tct | gca | 1008 |
| Asn | Pro | Ala | His | Lys | Ser | Gln | Leu | Val | Trp | Met | Ala | Cys | His | Ser | Ala |     |
|     |     |     |     | 325 |     |     |     |     | 330 |     |     |     |     | 335 |     |     |
| gca | ttt | gaa | gat | ctg | aga | gtg | tca | agt | ttc | atc | aga | ggg | aca | aaa | gtg | 1056 |
| Ala | Phe | Glu | Asp | Leu | Arg | Val | Ser | Ser | Phe | Ile | Arg | Gly | Thr | Lys | Val |     |
|     |     |     | 340 |     |     |     |     | 345 |     |     |     |     | 350 |     |     |     |
| gtc | cca | aga | gga | caa | ctg | tcc | act | aga | gga | gtt | caa | att | gct | tca | aat | 1104 |
| Val | Pro | Arg | Gly | Gln | Leu | Ser | Thr | Arg | Gly | Val | Gln | Ile | Ala | Ser | Asn |     |
|     |     | 355 |     |     |     |     | 360 |     |     |     |     | 365 |     |     |     |     |
| gaa | aac | atg | gaa | aca | atg | gac | tcc | att | act | ctt | gaa | ctg | aga | agc | aaa | 1152 |
| Glu | Asn | Met | Glu | Thr | Met | Asp | Ser | Ile | Thr | Leu | Glu | Leu | Arg | Ser | Lys |     |
|     | 370 |     |     |     |     | 375 |     |     |     |     | 380 |     |     |     |     |     |
| tac | tgg | gct | ata | aga | acc | agg | agc | gga | gga | aac | acc | aac | caa | cag | agg | 1200 |
| Tyr | Trp | Ala | Ile | Arg | Thr | Arg | Ser | Gly | Gly | Asn | Thr | Asn | Gln | Gln | Arg |     |
| 385 |     |     |     |     | 390 |     |     |     |     | 395 |     |     |     |     | 400 |     |
| gca | tct | gca | ggg | caa | atc | agt | gta | caa | cct | act | ttc | tcg | gta | cag | aga | 1248 |
| Ala | Ser | Ala | Gly | Gln | Ile | Ser | Val | Gln | Pro | Thr | Phe | Ser | Val | Gln | Arg |     |
|     |     |     |     | 405 |     |     |     |     | 410 |     |     |     |     | 415 |     |     |
| aat | ctt | cct | ttc | gag | aga | gcg | acc | atc | atg | gca | gca | ttt | aca | ggg | aac | 1296 |
| Asn | Leu | Pro | Phe | Glu | Arg | Ala | Thr | Ile | Met | Ala | Ala | Phe | Thr | Gly | Asn |     |
|     |     |     | 420 |     |     |     |     | 425 |     |     |     |     | 430 |     |     |     |
| act | gaa | ggc | aga | aca | tct | gac | atg | agg | act | gaa | att | ata | aga | atg | atg | 1344 |
| Thr | Glu | Gly | Arg | Thr | Ser | Asp | Met | Arg | Thr | Glu | Ile | Ile | Arg | Met | Met |     |
|     |     | 435 |     |     |     |     | 440 |     |     |     |     | 445 |     |     |     |     |
| gaa | agt | gcc | aga | cca | gaa | gat | gtg | tcc | ttc | cag | ggg | cgg | gga | gtc | ttc | 1392 |
| Glu | Ser | Ala | Arg | Pro | Glu | Asp | Val | Ser | Phe | Gln | Gly | Arg | Gly | Val | Phe |     |
|     | 450 |     |     |     |     | 455 |     |     |     |     | 460 |     |     |     |     |     |
| gag | ctc | tcg | gac | gaa | aaa | gca | acg | aac | ccg | atc | gtg | cct | tcc | ttt | gac | 1440 |
| Glu | Leu | Ser | Asp | Glu | Lys | Ala | Thr | Asn | Pro | Ile | Val | Pro | Ser | Phe | Asp |     |
| 465 |     |     |     |     | 470 |     |     |     |     | 475 |     |     |     |     | 480 |     |
| gtg | agt | aat | gag | gga | tct | tat | ttc | ttc | gga | gac | aat | gca | gag | gag | tat | 1488 |
| Val | Ser | Asn | Glu | Gly | Ser | Tyr | Phe | Phe | Gly | Asp | Asn | Ala | Glu | Glu | Tyr |     |
|     |     |     |     | 485 |     |     |     |     | 490 |     |     |     |     | 495 |     |     |
| aac | aat | taa |     |     |     |     |     |     |     |     |     |     |     |     |     | 1497 |

Asn Asn

```
<210> SEQ ID NO 19
<211> LENGTH: 34
<212> TYPE: DNA
<213> ORGANISM: PRRSV Virus (Lelystad Strain)

<400> SEQUENCE: 19
acgcgtcgac aatatgagat gttctcacaa attg                              34

<210> SEQ ID NO 20
<211> LENGTH: 33
<212> TYPE: DNA
<213> ORGANISM: PRRSV Virus (Lelystad Strain)

<400> SEQUENCE: 20
cgcggatccc gtctaggcct cccattgctc agc                               33

<210> SEQ ID NO 21
<211> LENGTH: 30
<212> TYPE: DNA
<213> ORGANISM: PRRSV Virus (ATCCVR2332 Strain)

<400> SEQUENCE: 21
aactgcagat gttggagaaa tgcttgaccg                                   30

<210> SEQ ID NO 22
<211> LENGTH: 30
<212> TYPE: DNA
<213> ORGANISM: PRRSV Virus (ATCCVR2332 Strain)

<400> SEQUENCE: 22
cgggatccct aaggacgacc ccattgttcc                                   30

<210> SEQ ID NO 23
<211> LENGTH: 32
<212> TYPE: DNA
<213> ORGANISM: PRRSV Virus (Lelystad Strain)

<400> SEQUENCE: 23
aaactgcagc aatggctcat cagtgtgcac gc                                32

<210> SEQ ID NO 24
<211> LENGTH: 30
<212> TYPE: DNA
<213> ORGANISM: PRRSV Virus (Lelystad Strain)

<400> SEQUENCE: 24
cgcggatcct tatcgtgatg tactggggag                                   30

<210> SEQ ID NO 25
<211> LENGTH: 32
<212> TYPE: DNA
<213> ORGANISM: PRRSV Virus (ATCCVR2332 Strain)

<400> SEQUENCE: 25
aaactgcagc aatggttaat agctgtacat tc                                32

<210> SEQ ID NO 26
<211> LENGTH: 32
<212> TYPE: DNA
<213> ORGANISM: PRRSV Virus (ATCCVR2332 Strain)

<400> SEQUENCE: 26
```

-continued

```
cgcggatccc tatcgccgta cggcactgag gg                    32

<210> SEQ ID NO 27
<211> LENGTH: 33
<212> TYPE: DNA
<213> ORGANISM: Porcine Parvovirus (NADL2 Strain)

<400> SEQUENCE: 27
aaaactgcag aatgagtgaa aatgtggaac aac                   33

<210> SEQ ID NO 28
<211> LENGTH: 33
<212> TYPE: DNA
<213> ORGANISM: Porcine Parvovirus (NADL2 Strain)

<400> SEQUENCE: 28
cgcggatccc tagtataatt ttcttggtat aag                   33

<210> SEQ ID NO 29
<211> LENGTH: 36
<212> TYPE: DNA
<213> ORGANISM: Hog Cholera Virus (Alfort Strain)

<400> SEQUENCE: 29
acgcgtcgac atgaaactag aaaaagccct gttggc                36

<210> SEQ ID NO 30
<211> LENGTH: 34
<212> TYPE: DNA
<213> ORGANISM: Hog Cholera Virus (Alfort Strain)

<400> SEQUENCE: 30
cgcggatcct catagccgcc cttgtgcccc ggtc                  34

<210> SEQ ID NO 31
<211> LENGTH: 36
<212> TYPE: DNA
<213> ORGANISM: Hog Cholera Virus (Alfort Strain)

<400> SEQUENCE: 31
acgcgtcgac atgtcaacta ctgcgtttct catttg                36

<210> SEQ ID NO 32
<211> LENGTH: 33
<212> TYPE: DNA
<213> ORGANISM: Hog Cholera Virus (Alfort Strain)

<400> SEQUENCE: 32
cgcggatcct cactgtagac cagcagcgag ctg                   33

<210> SEQ ID NO 33
<211> LENGTH: 32
<212> TYPE: DNA
<213> ORGANISM: Actinobaccillus Pleuropneumoniae (Serotype 1)

<400> SEQUENCE: 33
ttgtcgacgt aaatagctaa ggagacaaca tg                    32

<210> SEQ ID NO 34
<211> LENGTH: 29
<212> TYPE: DNA
<213> ORGANISM: Actinobaccillus Pleuropneumoniae (Serotype 1)
```

-continued

```
<400> SEQUENCE: 34
ttgaattctt cttcaacaga atgtaattc 29

<210> SEQ ID NO 35
<211> LENGTH: 31
<212> TYPE: DNA
<213> ORGANISM: Actinobaccillus Pleuropneumoniae (Serotype 1)

<400> SEQUENCE: 35
ttgaattcta tcgctacagt aaggagtacg g 31

<210> SEQ ID NO 36
<211> LENGTH: 31
<212> TYPE: DNA
<213> ORGANISM: Actinobacillus Pleuropneumoniae (Serotype 9)

<400> SEQUENCE: 36
ttggatccgc tatttatcat ctaaaaataa c 31

<210> SEQ ID NO 37
<211> LENGTH: 31
<212> TYPE: DNA
<213> ORGANISM: Actinobacillus Pleuropneumoniae (Serotype 9)

<400> SEQUENCE: 37
ttgtcgacga tcaattatat aaaggagact c 31

<210> SEQ ID NO 38
<211> LENGTH: 30
<212> TYPE: DNA
<213> ORGANISM: Actinobacillus Pleuropneumoniae (Serotype 9)

<400> SEQUENCE: 38
ttgaattcct cttcaactga tttgagtgag 30

<210> SEQ ID NO 39
<211> LENGTH: 29
<212> TYPE: DNA
<213> ORGANISM: Actinobacillus Pleuropneumoniae (Serotype 9)

<400> SEQUENCE: 39
ttgaattcgt aaatcttaaa gacctcacc 29

<210> SEQ ID NO 40
<211> LENGTH: 30
<212> TYPE: DNA
<213> ORGANISM: Actinobacillus Pleuropneumoniae (Serotype 9)

<400> SEQUENCE: 40
ttggatccac cataggattg ctatgatttg 30

<210> SEQ ID NO 41
<211> LENGTH: 30
<212> TYPE: DNA
<213> ORGANISM: Actinobacillus Pleuropneumoniae (Serotype 8)

<400> SEQUENCE: 41
tttgtcgaca tgagtacttg gtcaagcatg 30

<210> SEQ ID NO 42
<211> LENGTH: 29
<212> TYPE: DNA
<213> ORGANISM: Actinobacillus Pleuropneumoniae (Serotype 8)

-continued

<400> SEQUENCE: 42
tttatcgatt cttctactga atgtaattc 29

<210> SEQ ID NO 43
<211> LENGTH: 33
<212> TYPE: DNA
<213> ORGANISM: Actinobacillus Pleuropneumoniae (Serotype 8)

<400> SEQUENCE: 43
tttatcgatt tatgtttatc gttccacttc agg 33

<210> SEQ ID NO 44
<211> LENGTH: 32
<212> TYPE: DNA
<213> ORGANISM: Actinobacillus Pleuropneumoniae (Serotype 8)

<400> SEQUENCE: 44
ttggatcctt aagctgctct agctaggtta cc 32

<210> SEQ ID NO 45
<211> LENGTH: 32
<212> TYPE: DNA
<213> ORGANISM: Actinobacillus Pleuropneumoniae (Serotype 8)

<400> SEQUENCE: 45
tttatcgatt tcttcacgtt taccaacagc ag 32

<210> SEQ ID NO 46
<211> LENGTH: 31
<212> TYPE: DNA
<213> ORGANISM: Actinobacillus Pleuropneumoniae (Serotype 8)

<400> SEQUENCE: 46
tttatcgatt ctgatttttc cttcgatcgt c 31

<210> SEQ ID NO 47
<211> LENGTH: 33
<212> TYPE: DNA
<213> ORGANISM: Actinobacillus Pleuropneumoniae (Serotype 8)

<400> SEQUENCE: 47
tttatcgata cctgattgcg ttaattcata atc 33

<210> SEQ ID NO 48
<211> LENGTH: 31
<212> TYPE: DNA
<213> ORGANISM: Actinobacillus Pleuropneumoniae (Serotype 8)

<400> SEQUENCE: 48
tttatcgata aatctagtga tttagataaa c 31

<210> SEQ ID NO 49
<211> LENGTH: 913
<212> TYPE: PRT
<213> ORGANISM: Pseudorabies virus

<400> SEQUENCE: 49

```
Met Pro Ala Gly Gly Gly Leu Trp Arg Gly Pro Arg Gly His Arg Pro
1               5                   10                  15

Gly His His Gly Gly Ala Gly Leu Gly Arg Leu Trp Pro Ala Pro His
            20                  25                  30
```

```
His Ala Ala Ala Arg Gly Ala Val Ala Leu Ala Leu Leu Leu Leu
    35              40              45
Ala Leu Ala Ala Pro Pro Cys Gly Ala Ala Val Thr Arg Ala
 50              55              60
Ala Ser Ala Ser Pro Thr Pro Gly Thr Gly Ala Thr Pro Asn Asp Val
 65              70              75              80
Ser Ala Glu Ala Ser Leu Glu Glu Ile Glu Ala Phe Ser Pro Gly Pro
                85              90              95
Ser Glu Ala Pro Asp Gly Glu Tyr Gly Asp Leu Asp Ala Arg Thr Ala
            100             105             110
Val Arg Ala Ala Thr Glu Arg Asp Arg Phe Tyr Val Cys Pro Pro
        115             120             125
Pro Ser Gly Ser Thr Val Val Arg Leu Glu Pro Glu Gln Ala Cys Pro
    130             135             140
Glu Tyr Ser Gln Gly Arg Asn Phe Thr Glu Gly Ile Ala Leu Leu Phe
145             150             155             160
Lys Glu Asn Ile Ala Pro His Lys Phe Lys Ala His Ile Tyr Tyr Lys
                165             170             175
Asn Val Ile Val Thr Thr Val Trp Ser Gly Ser Thr Tyr Ala Ala Ile
            180             185             190
Thr Asn Arg Phe Thr Asp Arg Val Pro Val Pro Val Gln Glu Ile Thr
        195             200             205
Asp Val Ile Asp Arg Arg Gly Lys Cys Val Ser Lys Ala Glu Tyr Val
    210             215             220
Arg Asn Asn His Lys Val Thr Ala Phe Asp Arg Asp Glu Asn Pro Val
225             230             235             240
Glu Val Asp Leu Arg Pro Ser Arg Leu Asn Ala Leu Gly Thr Arg Ala
                245             250             255
Trp His Thr Thr Asn Asp Thr Tyr Thr Lys Ile Gly Ala Ala Gly Phe
            260             265             270
Tyr Gln Thr Gly Thr Ser Val Asn Cys Ile Val Glu Glu Val Glu Ala
        275             280             285
Arg Ser Val Tyr Pro Tyr Asp Ser Phe Ala Leu Ser Thr Gly Asp Ile
    290             295             300
Val Tyr Met Ser Pro Phe Tyr Gly Leu Arg Glu Gly Ala His Gly Glu
305             310             315             320
Gln Ile Gly Tyr Ala Pro Gly Arg Phe Gln Gln Val Glu His Tyr Tyr
                325             330             335
Pro Ile Asp Leu Asp Ser Arg Leu Arg Ala Ser Glu Ser Val Thr Arg
            340             345             350
Asn Phe Leu Arg Thr Pro His Phe Thr Val Ala Trp Asp Trp Ala Pro
        355             360             365
Lys Thr Arg Arg Val Cys Ser Leu Ala Lys Trp Arg Glu Ala Glu Glu
    370             375             380
Met Thr Arg Asp Glu Thr Arg Asp Gly Ser Phe Arg Phe Thr Ser Arg
385             390             395             400
Ala Leu Gly Ala Ser Phe Val Ser Asp Val Thr Gln Leu Asp Leu Gln
                405             410             415
Arg Val His Leu Gly Asp Cys Val Leu Arg Glu Ala Ser Glu Ala Ile
            420             425             430
Asp Ala Ile Tyr Arg Arg Tyr Asn Ser Thr His Val Leu Ala Gly
        435             440             445
Asp Arg Pro Glu Val Tyr Leu Ala Arg Gly Gly Phe Val Val Ala Phe
```

-continued

```
            450                 455                 460
Arg Pro Leu Ile Ser Asn Glu Leu Ala Gln Leu Tyr Ala Arg Glu Leu
465                 470                 475                 480

Glu Arg Leu Gly Leu Ala Gly Val Val Gly Pro Ala Ala Pro Ala Ala
                    485                 490                 495

Ala Arg Arg Ala Arg Arg Ser Pro Gly Pro Ala Gly Thr Pro Glu Pro
                500                 505                 510

Pro Ala Val Asn Gly Thr Gly His Leu Arg Ile Thr Thr Gly Ser Ala
                515                 520                 525

Glu Phe Ala Arg Leu Gln Phe Thr Tyr Asp His Ile Gln Ala His Val
            530                 535                 540

Asn Asp Met Leu Gly Arg Ile Ala Ala Trp Cys Glu Leu Gln Asn
545                 550                 555                 560

Lys Asp Arg Thr Leu Trp Ser Glu Met Ser Arg Leu Asn Pro Ser Ala
                565                 570                 575

Val Ala Thr Ala Ala Leu Gly Gln Arg Val Cys Ala Arg Met Leu Gly
                580                 585                 590

Asp Val Met Ala Ile Ser Arg Cys Val Glu Val Arg Gly Gly Val Tyr
            595                 600                 605

Val Gln Asn Ser Met Arg Val Pro Gly Glu Arg Gly Thr Cys Tyr Ser
610                 615                 620

Arg Pro Leu Val Thr Phe Glu His Asn Gly Thr Gly Val Ile Glu Gly
625                 630                 635                 640

Gln Leu Gly Asp Asp Asn Glu Leu Leu Ile Ser Arg Asp Leu Ile Glu
                645                 650                 655

Pro Cys Thr Gly Asn His Arg Arg Tyr Phe Lys Leu Gly Ser Gly Tyr
                660                 665                 670

Val Tyr Tyr Glu Asp Tyr Asn Tyr Val Arg Met Val Glu Val Pro Glu
            675                 680                 685

Thr Ile Ser Thr Arg Val Thr Leu Asn Leu Thr Leu Leu Glu Asp Arg
            690                 695                 700

Glu Phe Leu Pro Leu Glu Val Tyr Thr Arg Glu Leu Ala Asp Thr
705                 710                 715                 720

Gly Leu Leu Asp Tyr Ser Glu Ile Gln Arg Arg Asn Gln Leu His Ala
                725                 730                 735

Leu Lys Phe Tyr Asp Ile Asp Arg Val Val Lys Val Asp His Asn Val
                740                 745                 750

Val Leu Leu Arg Gly Ile Ala Asn Phe Phe Gln Gly Leu Gly Asp Val
                755                 760                 765

Gly Ala Ala Val Gly Lys Val Val Leu Gly Ala Thr Gly Ala Val Ile
                770                 775                 780

Ser Ala Val Gly Gly Met Val Ser Phe Leu Ser Asn Pro Phe Gly Ala
785                 790                 795                 800

Leu Ala Ile Gly Leu Leu Val Leu Ala Gly Leu Val Ala Ala Phe Leu
                805                 810                 815

Ala Tyr Arg His Ile Ser Arg Leu Arg Arg Asn Pro Met Lys Ala Leu
                820                 825                 830

Tyr Pro Val Thr Thr Lys Thr Leu Lys Glu Asp Gly Val Asp Glu Gly
                835                 840                 845

Asp Val Asp Glu Ala Lys Leu Asp Gln Ala Arg Asp Met Ile Arg Tyr
            850                 855                 860

Met Ser Ile Val Ser Ala Leu Glu Gln Gln Glu His Lys Ala Arg Lys
865                 870                 875                 880
```

-continued

Lys Asn Ser Gly Pro Ala Leu Leu Ala Ser Arg Val Gly Ala Met Ala
            885                 890                 895

Thr Arg Arg Arg His Tyr Gln Arg Leu Glu Ser Glu Asp Pro Asp Ala
            900                 905                 910

Leu

<210> SEQ ID NO 50
<211> LENGTH: 404
<212> TYPE: PRT
<213> ORGANISM: Aujesky's Disease Virus (NIA3 Strain)

<400> SEQUENCE: 50

Met Leu Leu Ala Ala Leu Leu Ala Ala Leu Val Ala Arg Thr Thr Leu
1               5                   10                  15

Gly Ala Asp Val Asp Ala Val Pro Ala Pro Thr Phe Pro Pro Pro Ala
                20                  25                  30

Tyr Pro Tyr Thr Glu Ser Trp Gln Leu Thr Leu Thr Thr Val Pro Ser
            35                  40                  45

Pro Phe Val Gly Pro Ala Asp Val Tyr His Thr Arg Pro Leu Glu Asp
    50                  55                  60

Pro Cys Gly Val Val Ala Leu Ile Ser Asp Pro Gln Val Asp Arg Leu
65                  70                  75                  80

Leu Asn Glu Ala Val Ala His Arg Arg Pro Thr Tyr Arg Ala His Val
                85                  90                  95

Ala Trp Tyr Arg Ile Ala Asp Gly Cys Ala His Leu Leu Tyr Phe Ile
            100                 105                 110

Glu Tyr Ala Asp Cys Asp Pro Arg Gln Ala Asp Leu Trp Ala Leu Pro
            115                 120                 125

Ala Pro His His Ala Asp Val Val Asp Pro Val Arg Gly Leu His Val
    130                 135                 140

Pro His Gly Gly Arg Ala Gly Ala Ala His Gly Gly Pro Arg Ala Val
145                 150                 155                 160

Gln Arg Gly Pro Val Pro Ala Pro Gly Val Arg Arg Arg Glu His
            165                 170                 175

Pro His Arg Leu His Gly Gly Ala Pro Arg Gly Ala Arg Val Pro Val
            180                 185                 190

Arg Pro Arg Gly Pro Ala Pro His Val Gln Val Arg Arg Val Leu Glu
            195                 200                 205

Arg Arg Gln Leu Gln Ala Gly Arg Gly Arg Asp Ala Ile Pro Asp Ala
            210                 215                 220

Val Leu Pro Ala Ala Pro Ala Pro Gly Gly Gly Glu Leu Leu Val Pro
225                 230                 235                 240

Gln Glu Arg Pro Asp Ala Pro Ala Gly Pro Arg Arg Arg His Ala Val
            245                 250                 255

Arg His Arg Pro Arg Ala Ala Leu Gly Gly Leu Ala Glu Ala Pro Ala
            260                 265                 270

Pro Ala Pro Ala Pro Ala Pro Glu Ala Arg Ala Arg Pro Gly Asp
            275                 280                 285

Ala Arg Ala Pro Arg Pro Pro Ala Arg Ala Gly Asp Ala Gly Pro Arg
            290                 295                 300

Arg Arg Gly Pro Pro His Ala Ala Thr Pro Glu Ala Arg Asp Ala Ala
305                 310                 315                 320

Pro Pro Leu Arg Pro Ala Gly Arg Arg Ala Gln Arg Val Ala Ala Ala
            325                 330                 335

```
Arg Gly Ala Val Pro Ala Ala Asp Pro Arg Arg Ala Gly Arg Leu Ala
                340                 345                 350

Pro Pro Leu Gly Asp Arg Arg His Gly His Arg Asp Gly Arg Ala Pro
                355                 360                 365

Gly Gly Arg Val Arg Leu His Leu Leu Pro Pro Glu Gly Gly Glu Gly
                370                 375                 380

Val Ser Pro Pro Gly Arg Ser Arg Gly Arg Arg Arg Ala Lys Ser Ala
385                 390                 395                 400

Ala Arg Ser Val

<210> SEQ ID NO 51
<211> LENGTH: 566
<212> TYPE: PRT
<213> ORGANISM: Porcine Flu Virus (SIV, H1N1 "SW" Strain

<400> SEQUENCE: 51

Met Glu Ala Lys Leu Phe Val Leu Phe Cys Thr Phe Thr Ala Leu Lys
1               5                   10                  15

Ala Asp Thr Ile Cys Val Gly Tyr His Ala Asn Asn Ser Thr Asp Thr
                20                  25                  30

Val Asp Thr Ile Leu Glu Lys Asn Val Thr Val Thr His Ser Val Asn
                35                  40                  45

Leu Leu Glu Asn Ser His Asn Gly Lys Leu Cys Ser Leu Asn Gly Val
            50                  55                  60

Ala Pro Leu Gln Leu Gly Lys Cys Asn Val Ala Gly Trp Ile Leu Gly
65                  70                  75                  80

Asn Pro Glu Cys Asp Leu Leu Leu Thr Ala Asn Ser Trp Ser Tyr Ile
                85                  90                  95

Ile Glu Thr Ser Asn Ser Glu Asn Gly Thr Cys Tyr Pro Gly Glu Phe
                100                 105                 110

Ile Asp Tyr Glu Glu Leu Arg Glu Gln Leu Ser Ser Val Ser Ser Phe
                115                 120                 125

Glu Arg Phe Glu Ile Phe Pro Lys Ala Asn Ser Trp Pro Asn His Glu
            130                 135                 140

Thr Thr Lys Gly Ile Thr Ala Ala Cys Ser Tyr Ser Gly Thr Pro Ser
145                 150                 155                 160

Phe Tyr Arg Asn Leu Leu Trp Ile Val Glu Arg Glu Asn Ser Tyr Pro
                165                 170                 175

Lys Leu Ser Lys Ser Tyr Thr Asn Asn Lys Gly Lys Glu Val Leu Ile
                180                 185                 190

Ile Trp Gly Val His His Pro Pro Thr Thr Asn Asp Gln Gln Ser Leu
            195                 200                 205

Tyr Gln Asn Ala Asp Ala Tyr Val Ser Val Gly Ser Ser Lys Tyr Asn
210                 215                 220

Arg Arg Phe Thr Pro Glu Ile Ala Ala Arg Pro Lys Val Lys Gly Gln
225                 230                 235                 240

Ala Gly Arg Met Asn Tyr Tyr Trp Thr Leu Leu Asp Gln Gly Asp Thr
                245                 250                 255

Ile Thr Phe Glu Ala Thr Gly Asn Leu Ile Ala Pro Trp Tyr Ala Phe
                260                 265                 270

Ala Leu Asn Lys Gly Ser Gly Ser Gly Ile Ile Thr Ser Asp Thr Pro
            275                 280                 285

Val His Asn Cys Asp Thr Lys Cys Gln Thr Pro His Gly Ala Leu Asn
290                 295                 300
```

-continued

```
Ser Ser Leu Pro Phe Gln Asn Val His Pro Ile Thr Ile Gly Glu Cys
305                 310                 315                 320

Pro Lys Tyr Val Lys Ser Thr Lys Leu Arg Met Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Ile Ala Ile Asp Gly Ile Ser Asn Lys Val Asn Ser Val Ile
385                 390                 395                 400

Glu Lys Met Asn Thr Gln Phe Thr Ala Val Gly Lys Glu Phe Asn Asp
                405                 410                 415

Leu Glu Lys Arg Ile Glu Asn Leu Asn Lys Lys Val Asp Asp Gly Phe
            420                 425                 430

Leu Asp Val Trp Thr Tyr Asn Ala Glu Leu Leu Val Leu Leu Glu Asn
        435                 440                 445

Glu Arg Thr Leu Asp Phe His Asp Phe Asn Val Arg Asn Leu Tyr Glu
    450                 455                 460

Lys Val Lys Ser Gln Leu Arg Asn Asn Ala Lys Glu Ile Gly Asn Gly
465                 470                 475                 480

Cys Phe Glu Phe Tyr His Lys Cys Asp Asp Glu Cys Met Lys Ser Val
                485                 490                 495

Lys Asn Gly Thr Tyr Asn Tyr Pro Lys Tyr Ser Glu Glu Ser Lys Leu
            500                 505                 510

Asn Arg Glu Glu Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 52
<211> LENGTH: 498
<212> TYPE: PRT
<213> ORGANISM: Swine Influenza Virus

<400> SEQUENCE: 52

Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Gly Met
            20                  25                  30

Val Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Lys Arg Asp Gly Lys Trp Met Arg Glu Leu Ile Leu Tyr Asp
```

```
                  100                 105                 110
Lys Glu Glu Ile Arg Arg Ile Trp Arg Gln Ala Asn Asn Gly Glu Asp
            115                 120                 125

Ala Thr Ala Gly Leu Thr His Leu Met Ile Trp His Ser Asn Leu Asn
130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Ala Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Ala Met Met Asp
225                 230                 235                 240

Gln Val Arg Glu Met Thr Asn Pro Gly Asn Ala Glu Thr Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Val Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Gln Leu Ser Thr Arg Gly Val Gln Ile Ala Ser Asn
        355                 360                 365

Glu Asn Met Glu Thr Met Glu Ser Ser Thr Leu Glu Leu Arg Ser Lys
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Leu Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 53
<211> LENGTH: 566
```

```
<212> TYPE: PRT
<213> ORGANISM: Swine Influenza Virus

<400> SEQUENCE: 53

Met Lys Thr Val Ile Ala Leu Ser Tyr Ile Phe Cys Leu Val Leu Gly
1               5                   10                  15

Gln Asp Leu Pro Glu Asn Gly Ser Ser Thr Ala Lys Pro Gly Leu Gly
                20                  25                  30

His His Ala Val Pro Asn Gly Thr Leu Val Lys Thr Ile Thr Asn Asp
            35                  40                  45

Gln Ile Glu Val Thr Asn Ala Thr Glu Leu Val Gln Ser Phe Ser Met
        50                  55                  60

Gly Lys Ile Cys Asn Asn Pro His Arg Val Leu Asp Gly Ala Asn Cys
65                  70                  75                  80

Thr Leu Ile Asp Ala Leu Leu Gly Asp Pro His Cys Asp Gly Phe Gln
                85                  90                  95

Asn Glu Lys Trp Asp Leu Phe Val Glu Arg Ser Lys Cys Phe Ser Asn
            100                 105                 110

Cys Tyr Pro Tyr Asp Val Pro Asp Tyr Ala Ser Leu Arg Ser Leu Ile
        115                 120                 125

Ala Ser Ser Gly Thr Leu Glu Phe Ile Asn Glu Gly Phe Asn Trp Thr
130                 135                 140

Gly Val Thr Gln Asn Gly Gly Ser Asn Ala Cys Lys Arg Gly Pro Asp
145                 150                 155                 160

Ser Gly Phe Phe Ser Arg Leu Asn Trp Leu Tyr Lys Ser Gly Asn Thr
                165                 170                 175

Tyr Pro Met Leu Asn Val Thr Met Pro Asn Ser Asp Asn Phe Asp Lys
            180                 185                 190

Leu Tyr Ile Trp Gly Val His His Pro Ser Thr Asp Arg Glu Gln Thr
        195                 200                 205

Asn Leu Tyr Val Gln Val Ser Gly Lys Ala Thr Val Phe Thr Lys Arg
210                 215                 220

Ser Gln Gln Thr Ile Ile Pro Asn Ser Arg Ser Arg Pro Trp Val Arg
225                 230                 235                 240

Gly Leu Ser Ser Arg Ile Ser Ile His Trp Thr Ile Val Lys Pro Gly
                245                 250                 255

Asp Ile Leu Ile Ile Asn Ser Asn Gly Asn Leu Ile Ala Pro Arg Gly
            260                 265                 270

Tyr Phe Lys Met His Asn Gly Arg Ser Ser Ile Met Arg Ser Asp Ala
        275                 280                 285

Pro Ile Gly Thr Cys Ser Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Ile Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400
```

```
Ile Glu Lys Thr Asn Gly Lys Phe His Gln Ile Glu Lys Glu Phe Ser
                405                 410                 415
Ile Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
        435                 440                 445
Asn Gln His Thr Ile Asp Leu Thr Asp Ser Glu Met Ser Lys Leu Phe
    450                 455                 460
Glu Lys Thr Arg Arg Gln Leu Arg Glu Asn Ala Glu Asp Met Gly Asn
465                 470                 475                 480
Gly Cys Leu Gln Ile Tyr His Lys Cys Asp Asn Ala Cys Ile Glu Ser
            485                 490                 495
Ile Arg Asn Gly Thr Tyr Asp His Asn Glu Tyr Arg Asp Glu Ala Leu
        500                 505                 510
Asn Asn Arg Phe Gln Ile Lys Gly Val Glu Leu Lys Ser Gly Tyr Lys
    515                 520                 525
Asp Trp Ile Leu Trp Ile Ser Ser Ala Ile Ser Cys Phe Leu Leu Cys
530                 535                 540
Val Val Leu Leu Gly Phe Ile Met Trp Ala Cys Gln Lys Gly Asn Ile
545                 550                 555                 560
Arg Cys Asn Ile Cys Ile
                565

<210> SEQ ID NO 54
<211> LENGTH: 498
<212> TYPE: PRT
<213> ORGANISM: Swine Influenza Virus

<400> SEQUENCE: 54

Met Ala Ser Gln Gly Thr Lys Arg Ser Tyr Glu Gln Met Glu Thr Gly
1               5                   10                  15
Gly Glu Arg Arg Asn Ala Thr Glu Ile Arg Ala Ser Val Gly Gly Met
            20                  25                  30
Val Gly Gly Ile Gly Arg Phe Tyr Ile Gln Met Cys Thr Lys Leu Lys
        35                  40                  45
Leu Ser Asp Tyr Glu Gly Arg Leu Ile Gln Asn Ser Ile Thr Ile Glu
    50                  55                  60
Arg Met Val Leu Ser Ala Phe Asp Glu Arg Arg Asn Lys Tyr Leu Glu
65                  70                  75                  80
Glu His Pro Ser Ala Gly Lys Asp Pro Lys Lys Thr Gly Gly Pro Ile
                85                  90                  95
Tyr Arg Lys Arg Asp Gly Lys Trp Met Arg Glu Leu Ile Met Tyr Asp
            100                 105                 110
Lys Glu Glu Ile Arg Arg Ile Trp Arg Gln Ala Asn Asn Gly Glu Asp
        115                 120                 125
Ala Thr Ala Gly Leu Thr His Leu Met Ile Trp His Ser Asn Leu Asn
    130                 135                 140
Asp Ala Thr Tyr Gln Arg Thr Arg Ala Leu Val Arg Thr Gly Met Asp
145                 150                 155                 160
Pro Arg Met Cys Ser Leu Met Gln Gly Ser Thr Leu Pro Arg Arg Ser
                165                 170                 175
Gly Ala Ala Gly Ala Ala Val Lys Gly Val Gly Thr Met Val Met Glu
            180                 185                 190
Leu Ile Arg Met Ile Lys Arg Gly Ile Asn Asp Arg Asn Phe Trp Arg
```

-continued

```
            195                 200                 205
Gly Glu Asn Gly Arg Arg Thr Arg Ile Ala Tyr Glu Arg Met Cys Asn
    210                 215                 220
Ile Leu Lys Gly Lys Phe Gln Thr Ala Ala Gln Arg Ala Thr Met Asp
225                 230                 235                 240
Gln Val Arg Glu Ser Arg Asn Pro Gly Asn Ala Glu Ile Glu Asp Leu
                245                 250                 255
Ile Phe Leu Ala Arg Ser Ala Leu Ile Leu Arg Gly Ser Val Ala His
                260                 265                 270
Lys Ser Cys Leu Pro Ala Cys Val Tyr Gly Leu Val Val Ala Ser Gly
                275                 280                 285
Tyr Asp Phe Glu Arg Glu Gly Tyr Ser Leu Val Gly Ile Asp Pro Phe
        290                 295                 300
Arg Leu Leu Gln Asn Ser Gln Val Phe Ser Leu Ile Arg Pro Asn Glu
305                 310                 315                 320
Asn Pro Ala His Lys Ser Gln Leu Val Trp Met Ala Cys His Ser Ala
                325                 330                 335
Ala Phe Glu Asp Leu Arg Val Ser Ser Phe Ile Arg Gly Thr Lys Val
                340                 345                 350
Val Pro Arg Gly Gln Leu Ser Thr Arg Gly Val Gln Ile Ala Ser Asn
                355                 360                 365
Glu Asn Met Glu Thr Met Asp Ser Ile Thr Leu Glu Leu Arg Ser Lys
    370                 375                 380
Tyr Trp Ala Ile Arg Thr Arg Ser Gly Gly Asn Thr Asn Gln Gln Arg
385                 390                 395                 400
Ala Ser Ala Gly Gln Ile Ser Val Gln Pro Thr Phe Ser Val Gln Arg
                405                 410                 415
Asn Leu Pro Phe Glu Arg Ala Thr Ile Met Ala Ala Phe Thr Gly Asn
                420                 425                 430
Thr Glu Gly Arg Thr Ser Asp Met Arg Thr Glu Ile Ile Arg Met Met
            435                 440                 445
Glu Ser Ala Arg Pro Glu Asp Val Ser Phe Gln Gly Arg Gly Val Phe
    450                 455                 460
Glu Leu Ser Asp Glu Lys Ala Thr Asn Pro Ile Val Pro Ser Phe Asp
465                 470                 475                 480
Val Ser Asn Glu Gly Ser Tyr Phe Phe Gly Asp Asn Ala Glu Glu Tyr
                485                 490                 495
Asn Asn
```